US012642493B2

(12) United States Patent
Chaudhary et al.

(10) Patent No.: US 12,642,493 B2
(45) Date of Patent: Jun. 2, 2026

(54) CONTEXT-AWARE VOLUMETRIC STYLE TRANSFER FOR ESTIMATING SINGLE VOLUME SURROGATES OF LUNG FUNCTION

(71) Applicant: University of Iowa Research Foundation, Iowa City, IA (US)

(72) Inventors: Muhammad F. A. Chaudhary, Iowa City, IA (US); Joseph M. Reinhardt, Iowa City, IA (US); Sarah E. Gerard, Iowa City, IA (US); Eric A. Hoffman, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 402 days.

(21) Appl. No.: 17/891,222

(22) Filed: Aug. 19, 2022

(65) Prior Publication Data

US 2023/0076809 A1 Mar. 9, 2023

Related U.S. Application Data

(60) Provisional application No. 63/235,510, filed on Aug. 20, 2021.

(51) Int. Cl.
*A61B 6/03* (2006.01)
*A61B 5/055* (2006.01)
*G06T 7/00* (2017.01)
(52) U.S. Cl.
CPC ............. *A61B 6/032* (2013.01); *A61B 5/055* (2013.01); *G06T 7/0014* (2013.01); *G06T 2207/30061* (2013.01)

(58) Field of Classification Search
USPC ......................................................... 382/131
See application file for complete search history.

(56) References Cited

U.S. PATENT DOCUMENTS 9,076,201 B1 * 7/2015 Negahdar ................. G06T 7/38
2005/0016530 A1 * 1/2005 McCutcheon ... A61B 17/12022
128/200.24

(Continued)

OTHER PUBLICATIONS

Chang et al. (Yushi Chang et al. A generative adversarial network (GAN)-based technique for synthesizing realistic respiratory motion in the extended cardiac-torso (XCAT) phantoms. May 2021, Phys. Med. Biol. 66 (Year: 2021).*

(Continued)

*Primary Examiner* — Chineyere Wills-Burns
*Assistant Examiner* — Aaron Timothy Bonansinga
(74) *Attorney, Agent, or Firm* — Goodhue, Coleman & Owens, P.C.

(57) ABSTRACT

A machine implemented method includes acquiring at a processor a first image of a patent by performing a computed tomography (CT) scan of a patient and applying at the processor a generative neural network model to the first image of the patient to generate a second image of the patient. The method may further include performing, at the processor, an analysis using the first image and the second image. The first image may be a first pulmonary image and the second image may be a second pulmonary image. The first pulmonary image may show lungs at a first volume and the second pulmonary image may show the lungs at a second volume, the first volume different from the second volume. The first pulmonary image may be a scan of the lungs at expiration and the second pulmonary image may be an inspiratory image of the lungs.

17 Claims, 22 Drawing Sheets

(56) References Cited

U.S. PATENT DOCUMENTS

| | | | | |
|---|---|---|---|---|
| 2018/0070905 A1* | 3/2018 | El-Baz | | G06T 7/149 |
| 2019/0220701 A1* | 7/2019 | Novak | | G06F 18/2113 |
| 2019/0325572 A1* | 10/2019 | Mansi | | A61B 5/103 |
| 2020/0034048 A1* | 1/2020 | Park | | G06N 3/088 |
| 2020/0085382 A1* | 3/2020 | Taerum | | A61B 5/7264 |
| 2020/0111194 A1* | 4/2020 | Wang | | G06N 3/047 |
| 2020/0184660 A1* | 6/2020 | Shi | | G06T 7/30 |
| 2020/0211160 A1* | 7/2020 | Zhang | | G06N 3/084 |
| 2020/0265276 A1* | 8/2020 | Xu | | G06T 7/0012 |
| 2020/0311940 A1* | 10/2020 | Krebs | | G06T 7/246 |
| 2020/0364908 A1* | 11/2020 | Li | | G01R 33/5618 |
| 2020/0402215 A1* | 12/2020 | Yang | | A61B 6/12 |
| 2021/0287799 A1* | 9/2021 | Guendel | | G16H 30/40 |
| 2021/0327054 A1* | 10/2021 | Liu | | G06T 7/11 |
| 2022/0036136 A1* | 2/2022 | Muehlberg | | G16H 30/40 |
| 2022/0039770 A1* | 2/2022 | Sharifi | | G16H 40/67 |
| 2022/0405948 A1* | 12/2022 | Spottiswoode | | G06T 5/00 |
| 2023/0022425 A1* | 1/2023 | Prevrhal | | A61B 6/527 |
| 2023/0157571 A1* | 5/2023 | Zeller | | A61B 5/743 |
| | | | | 600/408 |

OTHER PUBLICATIONS

Dong Nie. Medical Image Synthesis with Context-Aware Generative Adversarial Networks. Dec. 2016; arXiv:1612.05362v1 (Year: 2016).*

Jahani N, Choi et al. Assessment of regional ventilation and deformation using 4D-CT imaging for healthy human lungs during tidal breathing. J Appl Physiol (1985). Nov. 15, 2015;119(10):1064-74. doi: 10.1152/japplphysiol.00339.2015. Epub Aug. 27, 2015. PMID: 26316512; PMCID: (Year: 2015).*

Jiaxing Tan, "LGAN: Lung Segmentation in CT scans using Generative Adversarial Network", Jan. 2021,https://doi.org/10.1016/j. compmedimag.2020.101817 (Year: 2021).*

Loo, N.L. et al. "Generative Adversarial Network in Reconstructing Asynchronous Breathing Cycle", Jan. 2021. 3rd International Conference for Innovation in Biomedical Engineering and Life Sciences. ICIBEL 2019. IFMBE Proceedings, vol. 81. (Year: 2021).*

Chang et al. A generative adversarial network (GAN)-based technique for synthesizing realistic respiratory motion in the extended cardiac-torso (XCAT) phantoms, May 2021 Phys. Med. Biol. 66 115018, DOI 10.1088/1361-6560/ac01b4 (Year: 2021).*

Loo, N.L., Chiew, Y.S., Tan, C.P., Arunachalam, G., Ralib, A.M., Mat-Nor, M.B. "Generative Adversarial Network in Reconstructing Asynchronous Breathing Cycle", Jan. 2021. 3rd International Conference for Innovation in Biomedical Engineering and Life Sciences, vol. 81. (Year: 2021).*

Ho, T.T., Kim, T., Kim, W.J. et al. "A 3D-CNN model with CT-based parametric response mapping for classifying COPD subjects". Jan. 2021. Sci Rep 11, 34. https://doi.org/10.1038/s41598-020-79336-5 (Year: 2021).*

Tan et al. (Jiaxing Tan, "LGAN: Lung Segmentation in CT scans using Generative Adversarial Network", Jan. 2021, https://doi.org/10.1016/j.compmedimag.2020.101817) (Year: 2021).*

Sieren, J.P., Newell Jr, J.D., Barr, R.G., Bleecker, E.R., Burnette, N., Carretta, E.E., Couper, D., Goldin, J., Guo, J., Han, M.K., et al., 2016. Spiromics protocol for multicenter quantitative computed tomography to phenotype the lungs. American journal of respiratory and critical care medicine 194, 794-806.

Smith, B.M., Austin, J.H., Newell Jr, J.D., D'Souza, B.M., Rozenshtein, A., Hoffman, E.A., Ahmed, F., Barr, R.G., 2014. Pulmonary emphysema subtypes on computed tomography: the Mesa COPD study. The American Journal of Medicine 127, 23 pages.

Smith-Bindman, R., Lipson, J., Marcus, R., Kim, K.P., Mahesh, M., Gould, R., De Gonzalez, A.B., Miglioretti, D.L., 2009. Radiation dose associated with common computed tomography examinations and the associated lifetime attributable risk of cancer. Archives of internal medicine 169, 2078-2086.

T. Zhou, H. Fu, G. Chen, J. Shen, and L. Shao, "Hi-Net: Hybrid-fusion network for multi-modal MR image synthesis," IEEE Transactions on Medical Imaging, vol. 39, No. 9, pp. 2772-2781, 2020.

Tanner, C., Ozdemir, F., Profanter, R., Vishnevsky, V., Konukoglu, E., Goksel, O., 2018. Generative adversarial networks for MR-CT deformable image registration. arXiv preprint arXiv:1807.07349 (abstract).

Tolstikhin, I., Gelly, S., Bousquet, O., Simon-Gabriel, C.J., Schöolkopf, B., 2017. Adagan: Boosting generative models. arXiv preprint arXiv:1701.02386 (abstract).

Ulyanov, D., Vedaldi, A., Lempitsky, V., 2016. Instance normalization: The missing ingredient for fast stylization. arXiv preprint arXiv:1607.08022.

Vestbo, J., Hurd, S.S., Agustí, A.G., Jones, P.W., Vogelmeier, C., Anzueto, A., Barnes, P.J., Fabbri, L.M., Martinez, F. J., Nishimura, M., et al., 2013. Global strategy for the diagnosis, management, and prevention of chronic obstructive pulmonary disease: Gold executive summary. American Journal of Respiratory and Critical Care Medicine 187, 347-365.

Vincent, P., Larochelle, H., Lajoie, I., Bengio, Y., Manzagol, P.A., Bottou, L., 2010. Stacked denoising autoencoders: Learning useful representations in a deep network with a local denoising criterion. Journal of Machine Learning Research 11 (Abstract).

Wang, Z., Bovik, A.C., Sheikh, H.R., Simoncelli, E.P., 2004. Image quality assessment: from error visibility to structural similarity. IEEE Transactions on Image Processing 13, 600-612.

Wolterink, J.M., Dinkla, A.M., Savenije, M.H., Seevinck, P.R., van den Berg, C.A., Išgum, I., 2017. Deep MR to CT synthesis using unpaired data, in: International Workshop on Simulation and Synthesis in Medical Imaging, Springer. pp. 14-23.

Xia, Y., Ravikumar, N., Greenwood, J.P., Neubauer, S., Petersen, S.E., Frangi, A.F., 2021. Super-resolution of cardiac mr cine imaging using conditional gans and unsupervised transfer learning. Medical Image Analysis 71, 102037, Abstract.

Xu, B., Wang, N., Chen, T., Li, M., 2015. Empirical evaluation of rectified activations in convolutional network. arXiv preprint arXiv:1505.00853 (Abstract).

Yang, Q., Yan, P., Zhang, Y., Yu, H., Shi, Y., Mou, X., Kalra, M.K., Zhang, Y., Sun, L., Wang, G., 2018. Low-dose CT image denoising using a generative adversarial network with Wasserstein distance and perceptual loss. IEEE Transactions on Medical Imaging 37, 1348-1357.

Yi, X., Babyn, P., 2018. Sharpness-aware low-dose CT denoising using conditional generative adversarial network. Journal of Digital Imaging 31, 655-669.

Yin, Y., Hoffman, E.A., Lin, C.L., 2009. Mass preserving nonrigid registration of ct lung images using cubic b-spline. Medical physics 36, 4213-4222.

You, C., Li, G., Zhang, Y., Zhang, X., Shan, H., Li, M., Ju, S., Zhao, Z., Zhang, Z., Cong, W., et al., 2018. CT super-resolution gan constrained by the identical, residual, and cycle learning ensemble (GAN-Circle). IEEE Trans-actions on Medical Imaging 39, 188-203.

Zhang, H., Goodfellow, I., Metaxas, D., Odena, A., 2019. Self-attention generative adversarial networks, in: International conference on machine learning, PMLR. 10 pages.

Zhu, J.Y., Park, T., Isola, P., Efros, A.A., 2017. Unpaired image-to-image translation using cycle-consistent adversarial networks, in: Proceedings of the IEEE International Conference on Computer Vision, pp. 2223-2232.

B. Yu, L. Zhou, L. Wang, Y. Shi, J. Fripp, and P. Bourgeat, "Ea-GANs: Edge-aware generative adversarial networks for cross-modality MR image synthesis," IEEE Transactions on Medical Imaging, vol. 38, No. 7, pp. 1750-1762, 2019.

Bach, P.B., Mirkin, J.N., Oliver, T.K., Azzoli, C.G., Berry, D.A., Brawley, O.W., Byers, T., Colditz, G.A., Gould, M.K., Jett, J.R., et al., 2012. Benefits and harms of ct screening for lung cancer: a systematic review. Jama 307, 2418-2429.

Belloli, E.A., Degtiar, I., Wang, X., Yanik, G.A., Stuckey, L.J., Verleden, S.E., Kazerooni, E.A., Ross, B.D., Murray, S., Galbán, C.J., et al., 2017. Parametric response mapping as an imaging biomarker in lung transplant recipients. American journal of respiratory and critical care medicine 195, 942-952.

(56)　　　　　References Cited

OTHER PUBLICATIONS

Bhatt, S.P., Bodduluri, S., Newell, J.D., Hoffman, E.A., Sieren, J.C., Han, M.K., Dransfield, M.T., Reinhardt, J.M., Investigators, C., et al., 2016. CT-derived biomechanical metrics improve agreement between spirometry and emphy sema. Academic Radiology 23, 1255-1263.

Bodduluri, S., Bhatt, S.P., Hoffman, E.A., Newell, J.D., Martinez, C.H., Dransfield, M.T., Han, M.K., Reinhardt, J.M., 2017. Biomechanical CT metrics are associated with patient outcomes in COPD. Thorax 72, 409-414.

Bodduluri, S., Newell Jr, J.D., Hoffman, E.A., Reinhardt, J.M., 2013. Registration-based lung mechanical analysis of chronic obstructive pulmonary disease (COPD) using a supervised machine learning framework. Academic Radiology 20, 527-536.

Boes, J.L., Hoff, B.A., Bule, M., Johnson, T.D., Rehemtulla, A., Chamberlain, R., Hoffman, E.A., Kazerooni, E.A., Martinez, F.J., Han, M.K., et al., 2015. Parametric response mapping monitors temporal changes on lung ct scans in the subpopulations and intermediate outcome measures in copd study (spiromics). Academic radiology 22, 186-194.

Boudewijn, I.M., Postma, D.S., Telenga, E.D., Ten Hacken, N.H., Timens, W., Oudkerk, M., Ross, B.D., Galbán, C.J., van den Berge, M., 2015. Effects of ageing and smoking on pulmonary computed tomography scans using para-metric response mapping. European Respiratory Journal 46, 1193-1196.

Cao, K., Du, K., Ding, K., Reinhardt, J.M., Christensen, G.E., 2010b. Regularized nonrigid registration of lung CT images by preserving tissue vol. and vesselness measure. Grand Challenges in Medical Image Analysis , 43-54.

Celli, B.R., Wedzicha, J.A., 2019. Update on clinical aspects of chronic obstructive pulmonary disease. New England Journal of Medicine 381, 1257-1266.

Chen, Q., Koltun, V., 2014. Fast mrf optimization with application to depth reconstruction, in: Proceedings of the IEEE conference on computer vision and pattern recognition, pp. 3914-3921.

Chen, Y., Shi, F., Christodoulou, A.G., Xie, Y., Zhou, Z., Li, D., 2018. Effi- cient and accurate MRI super-resolution using a generative adversarial net-work and 3D multi-level densely connected network, in: International Conference on Medical Image Computing and Computer-Assisted Intervention, Springer. pp. 91-99.

Couper, D., LaVange, L.M., Han, M., Barr, R.G., Bleecker, E., Hoffman, E.A., Kanner, R., Kleerup, E., Martinez, F.J., Woodruff, P.G., et al., 2014. De-sign of the SubPopulations and Intermediate Outcomes in COPD Study (SPIROMICS). Thorax 69, 491-494.

D. A. Lynch, J. H. Austin, J. C. Hogg, P. A. Grenier, H.-U. Kauczor, A. A. Bankier, R. G. Barr, T. V. Colby, J. R. Galvin, P.A. Gevenois, et al., "CT-definable subtypes of chronic obstructive pulmonary disease: a statement of the Fleischner Society," Radiology, vol. 277, No. 1, pp. 192-205, 2015.

D. Giavarina, "Understanding Bland Altman analysis," Biochemia Med-ica, vol. 25, No. 2, pp. 141-151, 2015.

D. Lardinois, W. Weder, T. F. Hany, E. M. Kamel, S. Korom, B. Seifert, G. K. von Schulthess, and H. C. Steinert, "Staging of non-small-cell lung cancer with integrated positron-emission tomography and computed tomography," New England Journal of Medicine, vol. 348, No. 25, pp. 2500-2507, 2003.

D. Nie, R. Trullo, J. Lian, L. Wang, C. Petitjean, S. Ruan, Q. Wang, and D. Shen, "Medical image synthesis with deep convolutional adversarial networks," IEEE Transactions on Biomedical Engineering, vol. 65, No. 12, pp. 2720-2730, 2018.

Ding, K., Cao, K., Fuld, M.K., Du, K., Christensen, G.E., Hoffman, E.A., Rein hardt, J.M., 2012. Comparison of image registration based measures of regional lung ventilation from dynamic spiral ct with xe-ct. Medical physics 39, 5084-5098.

Emami, H., Dong, M., Nejad-Davarani, S.P., Glide-Hurst, C.K., 2018. Generating synthetic CTs from magnetic resonance images using generative adversarial networks. Medical Physics 45, 3627-3636 (manuscript).

Galbán, C.J., Han, M.K., Boes, J.L., Chughtai, K.A., Meyer, C.R., John-son, T.D., Galbán, S., Rehemtulla, A., Kazerooni, E.A., Martinez, F.J., et al., 2012. Computed tomography-based biomarker provides unique sig-nature for diagnosis of COPD phenotypes and disease progression. Nature Medicine 18, 1711.

Galbán , C.J., Chenevert, T.L., Meyer, C.R., Tsien, C., Lawrence, T.S., Hamstra, D.A., Junck, L., Sundgren, P.C., Johnson, T.D., Ross, D.J., et al., 2009. The parametric response map is an imaging biomarker for early cancer treatment outcome. Nature medicine 15, 572-576.

Gerard, S.E., Herrmann, J., Kaczka, D.W., Musch, G., Fernandez-Bustamante, A., Reinhardt, J.M., 2020. Multi-resolution convolutional neural net-works for fully automated segmentation of acutely injured lungs in multiple species. Medical Image Analysis 60, 101592. (Submitting abstract).

Gorbunova, V., Sporring, J., Lo, P., Loeve, M., Tiddens, H.A., Nielsen, M., Dirksen, A., de Bruijne, M., 2012. Mass preserving image registration for lung ct. Medical image analysis 16, 786-795.

Ho, T.T., Kim, T., Kim, W.J., Lee, C.H., Chae, K.J., Bak, S.H., Kwon, S.O., Jin, G.Y., Park, E.K., Choi, S., 2021. A 3d-cnn model with ct-based parametric response mapping for classifying copd subjects. Scientific Reports 11, 1-12.

Ioffe, S., Szegedy, C., 2015. Batch normalization: Accelerating deep network training by reducing internal covariate shift. arXiv preprint arXiv:1502.03167. Abstract.

Isola, P., Zhu, J.Y., Zhou, T., Efros, A.A., 2017. Image-to-image translation with conditional adversarial networks, in: Proceedings of the IEEE Conference on Computer Vision and Pattern Recognition, pp. 1125-1134.

J. Johnson, A. Alahi, and L. Fei-Fei, "Perceptual losses for real-time style transfer and super-resolution," in European Conference on Computer Vision, pp. 694-711, Springer, 2016.

Jin, D., Xu, Z., Tang, Y., Harrison, A.P., Mollura, D.J., 2018. CT-realistic lung nodule simulation from 3D conditional generative adversarial networks for robust lung segmentation, in: International Conference on Medical Image Computing and Computer-Assisted Intervention, Springer. pp. 732-740.

Jing, Y., Yang, Y., Feng, Z., Ye, J., Yu, Y., Song, M., 2019. Neural style transfer: A review. IEEE Transactions on Visualization and Computer Graphics.

K. B. Newman, D. A. Lynch, L. S. Newman, D. Ellegood, and J. D. Newell Jr, "Quantitative computed tomography detects air trapping due to asthma," Chest, vol. 106, No. 1, pp. 105-109, 1994.

L. A. Gatys, A. S. Ecker, and M. Bethge, "Image style transfer using convolutional neural networks," in Proceedings of the IEEE Conference on Computer Vision and Pattern Recognition, pp. 2414-2423, 2016.

Labaki, W.W., Gu, T., Murray, S., Hatt, C.R., Galbán, C.J., Ross, B.D., Martinez, C.H., Curtis, J.L., Hoffman, E.A., Pompe, E., et al., 2019. Voxel-wise longitudinal parametric response mapping analysis of chest computed tomography in smokers. Academic radiology 26, 217-223.

Ledig, C., Theis, L., Huszár, F., Caballero, J., Cunningham, A., Acosta, A., Aitken, A., Tejani, A., Totz, J., Wang, Z., et al., 2017. Photo-realistic single image super-resolution using a generative adversarial network, in: Proceedings of the IEEE Conference on Computer Vision and Pattern Recognition, pp. 4681-4690.

Lyu, Q., Shan, H., Wang, G., 2020. MRI super-resolution with ensemble learn-ing and complementary priors. IEEE Transactions on Computational Imaging 6, 615-624.

M. Frid-Adar, I. Diamant, E. Klang, M. Amitai, J. Goldberger, and H. Greenspan, "GAN-based synthetic medical image augmentation for increased CNN performance in liver lesion classification," Neurocom-puting, vol. 321, pp. 321-331, 2018.

Mao, X., Li, Q., Xie, H., Lau, R.Y., Wang, Z., Paul Smolley, S., 2017. Least squares generative adversarial networks, in: Proceedings of the IEEE inter-national conference on computer vision, pp. 2794-2802.

Maselli, D.J., Yen, A., Wang, W., Okajima, Y., Dolliver, W.R., Mercugliano, C., Anzueto, A., Restrepo, M.I., Aksamit, T. R., Basavaraj, A., et al., 2021. Small airway disease and emphysema are associated with future exacerbations in smokers with ct-derived bronchiectasis and copd: Results from the copdgene cohort. Radiology, 204052.

(56) References Cited

OTHER PUBLICATIONS

Milz, S., Rudiger, T., Suss, S., 2018. Aerial GANeration: Towards realistic data augmentation using conditional GANs, in: Proceedings of the European Conference on Computer Vision (ECCV), pp. 1-14.

Nie, D., Shen, D., 2020. Adversarial confidence learning for medical image segmentation and synthesis. International Journal of Computer Vision 128.

Nie, D., Trullo, R., Lian, J., Petitjean, C., Ruan, S., Wang, Q., Shen, D., 2017. Medical image synthesis with context-aware generative adversarial networks, in: International Conference on Medical Image Computing and Computer-Assisted Intervention, Springer. pp. 417-425.

Pompe, E., van Rikxoort, E.M., Schmidt, M., Rühaak, J., Estrella, L.G., Vliegenthart, R., Oudkerk, M., de Koning, H.J., van Ginneken, B., de Jong, P.A., et al., 2015. Parametric response mapping adds value to current computed tomography biomarkers in diagnosing chronic obstructive pulmonary disease. American journal of respiratory and critical care medicine 191, 1084-1086.

R. Zhang, P. Isola, A. A. Efros, E. Shechtman, and O. Wang, "The unreasonable effectiveness of deep features as a perceptual metric," in Proceedings of the IEEE Conference on Computer Vision and Pattern Recognition, pp. 586-595, 2018.

Radford, A., Metz, L., Chintala, S., 2016. Unsupervised representation learning with deep convolutional generative adversarial networks. arXiv preprint arXiv:1511.06434. Abstract.

Regan, E.A., Hokanson, J.E., Murphy, J.R., Make, B., Lynch, D.A., Beaty, T.H., Curran-Everett, D., Silverman, E.K., Crapo, J.D., 2010. Genetic epidemiology of COPD (COPDGene) study design. COPD: Journal of Chronic Obstructive Pulmonary Disease 7, 32-43.

Reinhardt, J.M., Ding, K., Cao, K., Christensen, G.E., Hoffman, E.A., Bodas, S.V., 2008. Registration-based estimates of local lung tissue expansion com-pared to xenon CT measures of specific ventilation. Medical Image Analysis 12, 752-763.

Ronneberger, O., Fischer, P., Brox, T., 2015. U-Net: Convolutional networks for biomedical image segmentation, in: International Conference on Medical Image Computing and Computer-Assisted Intervention, Springer. pp. 234-241.

S. E. Gerard, T. J. Patton, G. E. Christensen, J. E. Bayouth, and J. M. Reinhardt, "FissureNet: A deep learning approach for pulmonary fissure detection in CT images," IEEE Transactions on Medical Imaging, vol. 38, No. 1, pp. 156-166, 2018.

Shan, H., Zhang, Y., Yang, Q., Kruger, U., Kalra, M.K., Sun, L., Cong, W., Wang, G., 2018. 3-D convolutional encoder-decoder network for low-dose CT via transfer learning from a 2-D trained network. IEEE Transactions on Medical Imaging 37, 1522-1534.

Shin, H.C., Tenenholtz, N.A., Rogers, J.K., Schwarz, C.G., Senjem, M.L., Gunter, J.L., Andriole, K.P., Michalski, M., 2018. Medical image synthesis for data augmentation and anonymization using generative adversarial net-works, in: International Workshop on Simulation and Synthesis in Medical Imaging, Springer. pp. 1-11.

Siddiquee, M.M.R., Zhou, Z., Tajbakhsh, N., Feng, R., Gotway, M.B., Bengio, Y., Liang, J., 2019. Learning fixed points in generative adversarial networks: From image-to-image translation to disease detection and localization, in: Proceedings of the IEEE International Conference on Computer Vision, pp. 191-200.

B. Yu, L. Zhou, L. Wang, Y. Shi, J. Fripp, and P. Bourgeat, "Sample-adaptive GANs: linking global and local mappings for cross-modality MR image synthesis," IEEE Transactions on Medical Imaging, vol. 39, No. 7, pp. 2339-2350, 2020.

Cao, K., Ding, K., Christensen, G.E., Reinhardt, J.M., 2010a. Tissue vol. and vesselness measure preserving nonrigid registration of lung ct images, in: Medical Imaging 2010: Image Processing, International Society for Op-tics and Photonics. p. 762309.

Goodfellow, I., Pouget-Abadie, J., Mirza, M., Xu, B., Warde-Farley, D., Ozair, S., Courville, A., Bengio, Y., 2014. Generative adversarial networks, in: Advances in Neural Information Processing Systems, pp. 2672-2680.

H. Uzunova, J. Ehrhardt, and H. Handels, "Memory-efficient GAN-based domain translation of high resolution 3D medical images," Com-puterized Medical Imaging and Graphics, vol. 86, p. 101801, 2020.

H. Yang, J. Sun, A. Carass, C. Zhao, J. Lee, J. L. Prince, and Z. Xu, "Unsupervised MR-to-CT synthesis using structure-constrained CycleGAN," IEEE Transactions on Medical Imaging, vol. 39, No. 12, pp. 4249-4261, 2020.

Kingma, D.P., Mohamed, S., Rezende, D.J., Welling, M., 2014. Semi-supervised learning with deep generative models, in: Advances in Neural Information Processing Systems, 9 pages.

Mahapatra, D., Antony, B., Sedai, S., Garnavi, R., 2018. Deformable medical image registration using generative adversarial networks, in: 2018 IEEE 15th International Symposium on Biomedical Imaging (ISBI 2018), IEEE. pp. 1449-1453.

Ran, M., Hu, J., Chen, Y., Chen, H., Sun, H., Zhou, J., Zhang, Y., 2019. De-noising of 3D magnetic resonance images using a residual encoder-decoder wasserstein generative adversarial network. Medical Image Analysis 55, 165-180.

Reinhardt, J.M., Christensen, G.E., Hoffman, E.A., Ding, K., Cao, K., 2007. Registration-derived estimates of local lung expansion as surrogates for regional ventilation, in: Biennial International Conference on Information Processing in Medical Imaging, Springer. 12 pages.

S. Bera and P. K. Biswas, "Noise conscious training of non local neural network powered by self attentive spectral normalized markovian patch GAN for low dose CT denoising," IEEE Transactions on Medical Imaging, vol. 40, No. 12, pp. 3663-3673, 2021.

S. U. Dar, M. Yurt, L. Karacan, A. Erdem, E. Erdem, and T. Ç ukur, "Image synthesis in multi-contrast MRI with conditional generative adversarial networks," IEEE Transactions on Medical Imaging, vol. 38, No. 10, pp. 2375-2388, 2019.

S. You, B. Lei, S. Wang, C. K. Chui, A. C. Cheung, Y. Liu, M. Gan, G. Wu, and Y. Shen, "Fine perceptive GANs for brain MR image super-resolution in wavelet domain," IEEE Transactions on Neural Networks and Learning Systems, 2022.

Wallace, D.L., 1959. Simplified beta-approximations to the Kruskal-Wallis H test. Journal of the American Statistical Association 54, 225-230.

Yu, B., Zhou, L., Wang, L., Fripp, J., Bourgeat, P., 2018. 3D cGAN based cross-modality MR image synthesis for brain tumor segmentation, in: 2018 IEEE 15th International Symposium on Biomedical Imaging (ISBI 2018), IEEE. pp. 626-630.

Z. Tu and X. Bai, "Auto-context and its application to high-level vision tasks and 3D brain image segmentation," IEEE Transactions on Pattern Analysis and Machine Intelligence, vol. 32, No. 10, pp. 1744-1757, 2009.

Zhang, Y., Miao, S., Mansi, T., Liao, R., 2018. Task driven generative modeling for unsupervised domain adaptation: Application to X-ray image segmentation, in: International Conference on Medical Image Computing and Computer-Assisted Intervention, Springer. 9 pages.

Zhang, Y., Yang, L., Chen, J., Fredericksen, M., Hughes, D.P., Chen, D.Z., 2017. Deep adversarial networks for biomedical image segmentation utilizing unannotated images, in: International Conference on Medical Image Computing and Computer-Assisted Intervention, Springer. pp. 408-416.

* cited by examiner

| TABLE CONTROLLER 22 | | |
|---|---|---|
| X-RAY CONTROLLER 24 | COMPUTER W/ PROCESSOR(S) 20 | USER INTERFACE 28 |
| GANTRY MOTOR CONTROLLER 26 | | STORAGE MEDIA W/ INSTRUCTIONS 30 |

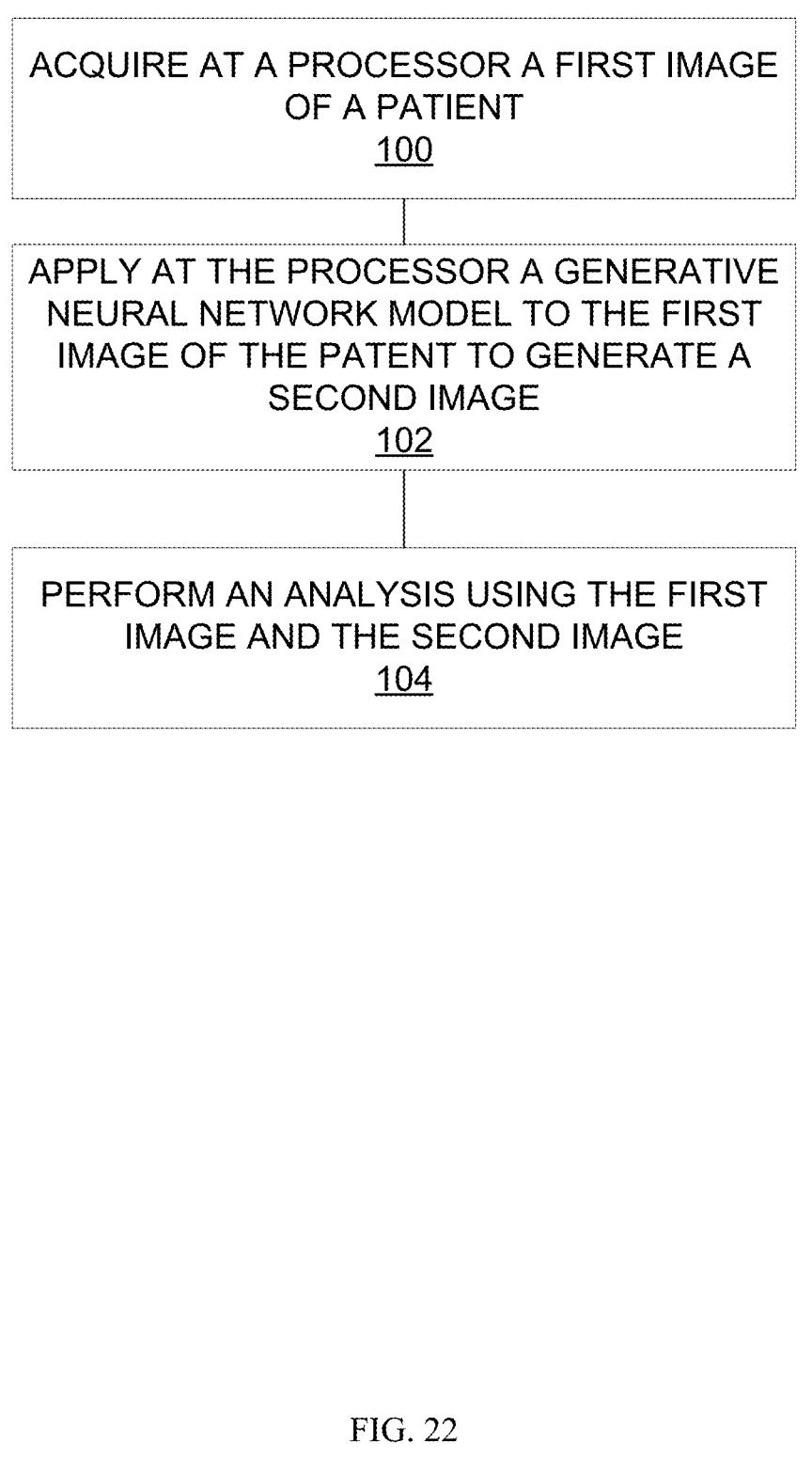

ACQUIRE AT A PROCESSOR A FIRST IMAGE
OF A PATIENT
<u>100</u>

APPLY AT THE PROCESSOR A GENERATIVE
NEURAL NETWORK MODEL TO THE FIRST
IMAGE OF THE PATENT TO GENERATE A
SECOND IMAGE
<u>102</u>

PERFORM AN ANALYSIS USING THE FIRST
IMAGE AND THE SECOND IMAGE
<u>104</u>

FIG. 22

CONTEXT-AWARE VOLUMETRIC STYLE TRANSFER FOR ESTIMATING SINGLE VOLUME SURROGATES OF LUNG FUNCTION

RELATED APPLICATIONS

This application claims priority to U.S. Provisional Patent Application 63/235,510, filed Aug. 20, 2021, entitled "Ensemble-driven adversarial confidence learning for estimating single volume surrogates of pulmonary function" hereby incorporated by reference in its entirety.

GRANT REFERENCE

This invention was made with government support under R01HL142625 awarded by the National Institute of Health. The government has certain rights in the invention.

FIELD OF THE INVENTION

The present invention relates to imaging. More particularly, but not exclusively, the present invention relates to biomedical imaging and especially imaging of lungs.

BACKGROUND

Although the background is discussed primarily with respect to biomedical imaging and especially imaging of lungs at different volumes, it is to be understood that the present disclosure has wider applicability and impact. Therefore, the present disclosure is not to be limited to or by the background discussion provided herein.

Computed tomography (CT) is a well-known imaging modality used to capture the anatomical details of internal organs under various pathological conditions. It is increasingly becoming a standard tool for diagnosing various cardio-thoracic diseases such as pulmonary fibrosis, chronic obstructive pulmonary disease (COPD), coronary artery disease, mediastinal tumors, and pulmonary embolisms, to name a few. CT imaging is particularly useful for detecting and characterizing COPD—a complex disorder that manifests as a heterogeneous mixture of airways disease and emphysema (Celli and Wedzicha (2019); Galbán et al. (2012)). Advancements in CT hardware have enabled high-resolution chest scans, used to capture the extent of airway obstruction and pulmonary tissue destruction across various stages of COPD. Several multi-center initiatives, targeted towards prevention and improved treatment of the disease, now rely on multiple-volume CT scans in addition to conventional pulmonary function tests (Regan et al. (2011); Couper et al. (2014); Smith et al. (2014)). CT imaging is increasingly being used for devising timely clinical interventions and treatment planning. Although, high-resolution CT imaging can effectively reveal anatomical structures of the lung parenchyma as well as the airways, it fails to capture the regional variation in lung function, critical for understanding the extent and progression patterns of COPD.

Image registration has been used to process CT scans at multiple volumes for estimating local abnormalities in lung function. Most commonly, inspiratory-expiratory volume pairs are matched to estimate regional tissue damage and airways disease. Galbán et al. (2012) used parametric response mapping (PRM) for quantifying total emphysema and functional small airways disease (fSAD) from co-registered, inspiratory-expiratory chest CT volumes. More importantly, they were able to derive a spatial distribution of parenchymal tissue damage and fSAD. PRM has gained widespread clinical attention (Pompe et al. (2015)), since it is able to provide regional insights into lung function. PRM has been used to detect and stage COPD (Ho et al. (2021); Boes et al. (2015)), predict COPD progression (Boes et al. (2015)), and was associated with future exacerbations (Maselli et al. (2021)). The spatial distribution of lung function derived from PRMs have also been demonstrated to be associated with hyperpolarized gas magnetic resonance imaging—a well-known functional imaging modality for the lung (Capaldi et al. (2016)). Apart from COPD, PRM has been used as an imaging biomarker for understanding the effects of smoking on lungs (Boudewijn et al. (2015); Labaki et al. (2019)), for predicting mortality in lung transplant patients with variable spirometric patterns (Belloli et al. (2017)), and for assessing survival in cancer treatment (Galbán et al. (2009)).

Another well-known approach for estimating regional lung function measures relies on registration deformation field for estimating local biomechanical properties of the lung. (Reinhardt et al. (2007, 2008)). Reinhardt et al. (2007, 2008) used deformable image registration (DIR) for estimating local lung expansion from respiratory-gated CT scans. Jacobian determinant (J) of the registration displacement field was used to quantify local volume change. The Jacobian maps were also validated against a well-known, non-invasive method for estimating regional lung ventilation—the Xenon-enhanced CT (Xe-CT). Registration-derived biomechanical measures have also gained widespread attention for understanding COPD and developing prognostic markers for its progression. Bodduluri et al. (2013) demonstrated that for a complex task such as COPD severity prediction, the biomechanical features, extracted from J, performed better than the conventional CT texture and density features. Bhatt et al. (2016) showed improved agreement between registration-based mechanics and spirometric measures of lung function, and concluded that dual volume (inspiration-expiration) biomechanical measures were better indicators of declining lung function and emphysema. Another important work by Bodduluri et al. (2017) identified the mean of J tobe significantly associated with several indices of lung function and patient health, including forced expiratory volume in one second ($FEV_1$), emphysema, and six minutes walk distance (6 MWD). All such studies point towards the effectiveness of registration-based mechanical features for assessing COPD development and progression.

Image registration frameworks require multiple (or at least dual-volume) CT scans for computing different measures of local lung function, thereby restricting its applicability to patients where multiple volume scans are not possible or available. Patients with advanced stage COPD, with reduced lung function, are unable to hold their breaths for acquiring scans at different volumes. Another disadvantage of acquiring high-resolution CT scans at different volumes is the exposure to higher radiation dosage, which is associated with risk of developing cancer (Smith-Bindman et al. (2009); Bach et al. (2012)). These problems strictly limit the use of higher-dose CT scans for patients with severe COPD at different breathing levels.

Several state-of-the-art lung image registration methods incur high computational cost required to match large 3D chest CT volumes. Iterative optimization, and subject-specific hyper-parameter tuning takes a lot of time, making it difficult to scale these approaches for increasingly large COPD cohort studies. The aforementioned limitations of acquiring image registration measures of lung function, however, do not undermine their significant clinical success. Rather, they call for robust, fast, and scalable methods for computing them.

A seemly unrelated subject to one not having the benefit of this disclosure is generative modeling. Recently, generative modeling (Kingma and Welling (2013); Goodfellow et al. (2014); Kingma et al. (2014)) has emerged as a very useful tool for various image-to-image translation tasks, a few of which include, image denoising (Vincent et al. (2010)), super-resolution (Ledig et al. (2017)), style transfer (Jing et al. (2019)), and data augmentation (Milz et al. (2018)). The most prominent in this paradigm, are the generative adversarial networks (GANs) (Goodfellow et al. (2014)), that have outperformed their non-adversarial counterparts like the vanilla and variational autoencoders. Their popularity is not limited to natural images, as GANs have been successfully used for various medical image analysis tasks including image denoising (Yang et al. (2018); Shan et al. (2018); Ran et al. (2019); Yi and Babyn (2018)), super-resolution (You et al. (2019); Lyu et al. (2020); Chen et al. (2018)), synthesis (Nie et al. (2017); Emami et al. (2018); Wolterink et al. (2017); Siddiquee et al. (2019)), segmentation (Zhang et al. (2017, 2018); Yu et al. (2018); Jin et al. (2018)), registration (Mahapatra et al. (2018); Tanner et al. (2018)), and data augmentation (Shin et al. (2018)). Yang et al. (2018) developed a GAN with joint perceptual and Wassersteinloss to denoise low-dose CT. Building on this work, You et al. (2019) developed a cycle-GAN (Zhu et al. (2017)) for converting low-dose CTs to high-resolution CT scans. Several GAN-based image synthesis methods also address the problem of converting magnetic resonance images (MRI) to CT for radiation treatment planning (Nie et al. (2017); Emami et al. (2018); Wolterink et al. (2017)). A prominent example is the context-aware GAN proposed by Nie et al. (2017) for estimating CT images from MRI. GANs have also been used for various segmentation tasks, including a CT-based method for simulating lung nodules using 3D GANs (Jin et al. (2018)).

Thus, despite the widespread use of imaging technologies such as CT imaging and despite the availability of various approaches to image analysis, problems and limitations remain.

SUMMARY

Therefore, it is a primary object, feature, and/or advantage of the present disclosure to improve on the state of the art and overcome the deficiencies within the art.

It is a further object, feature, or advantage of the present disclosure to leverage a biomedical image in new and surprising ways.

It is a still further object, feature, or advantage of the present disclosure to provide methods and system which minimize the number of images needed to evaluate a patient in order to provide more rapid results.

It is a further object, feature, or advantage of the present disclosure to provide methods and system which minimize the number of images needed to evaluate a patient in order to reduce the patient's exposure to radiation in a single imaging session or to increase the number frequency of imaging sessions.

It is a still further object, feature, or advantage of the present disclosure to provide methods and system which minimize the number of images needed to evaluate a patient in order to reduce expense.

It is another object, feature, or advantage of the present disclosure to provide methods and systems which reduce or simplify the requirements for patient compliance and/or reduce the effort required by a patient in obtaining imagery.

A further object, feature, or advantage is to provide methods and systems which eliminate the need for a patient to hold their breath at expiration in order to obtain a corresponding image of the patient's lungs at expiration.

A still further object, feature, or advantage is to provide methods and systems which allow for repeatability and consistence of lung imaging such as by not requiring a scan of a patient's lungs at expiration.

It is yet another object, feature, or advantage of the present disclosure to leverage existing data sets of biomedical images.

It is a further object, feature, or advantage of the present disclosure to provide for directly translating anatomical structures of the lung parenchyma to different measures of lung function.

It is a still further object, feature, or advantage of the present disclosure to provide for methods and systems which only require a single lung image at inspiration but are sufficient for providing the same insights as if both a lung image at inspiration and an expiratory lung image were acquired.

It is another object, feature, or advantage to allow for retrospective assessment of patient scans including from clinical databases.

A further object, feature, or advantage is to allow for better evaluation of lung transplant subjects.

It is yet another object, feature, or advantage to avoid registration methods which incur large computational cost and rely on multi-volume computed tomography scans.

It is a further object, feature, or advantage to provide a registration-independent, adversarial learning approach to estimate three different measures of regional lung deformation directly from the expiratory computed tomography scan.

It is a still further object, feature, or advantage to provide methods and systems which allow for generation of one or more images from a single scan.

Another object, feature, or advantage is to provide methods and systems to generate an image from a scan where the image and the scan are of lungs at different volumes.

Yet another object, feature, or advantage is to provide methods and systems which may be used with different types of imaging technologies including CT, MRI, and other imaging technologies.

A further object, feature, or advantage is to provide methods and systems which may be used with imagery of different types of organs or biological tissue.

A still further object, feature, or advantage is to use generative models for cross-volume computed tomography.

Another object, feature, or advantage is to us use a fully convolutional 3D GAN framework that addresses the slice-wise discontinuity presented by 2D GAN approaches.

Yet another object, feature, or advantage is to provide for better model texture synthesis and style transfer across volumes using a multi-view perceptual similarity module.

A further object, feature, or advantage is to extend auto-context (AC) originally developed for image segmentation, for dense regression task of cross-volume synthesis.

A still further object, feature, or advantage is to provide a comparison of performance between methods disclosed here and state-of-the-art 2D and 3D image-to-image translation methods.

Another object, feature, or advantage is to demonstrate effectiveness of one model using a large multi-center cohort of almost 1500 participants with a varying degree of disease severity.

Yet another object, feature, or advantage is to demonstrate that synthetic images derived using methods described herein can be used to reliably compute clinical end-points such as PRM and air-trapping.

One or more of these and or other objects, features, or advantages will become apparent from the specification and claims that follow. No single embodiment need provide each or every object, feature, or advantage as different embodiments may have different objects, features, and advantages. The present disclosure is not to be limited by or to these objects, features, or advantages.

According to one aspect, a machine implemented method includes acquiring at a processor a first image of a patient by performing a computed tomography (CT) scan of a patient and applying at the processor a generative neural network model to the first image of the patient to generate a second image of the patient. The method may further include performing, at the processor, an analysis using the first image and the second image. The first image may be a first pulmonary image and the second image may be a second pulmonary image. The first pulmonary image may show lungs at a first volume and the second pulmonary image may show the lungs at a second volume, the first volume different from the second volume. The first pulmonary image may be a scan of the lungs at expiration and the second pulmonary image may be an inspiratory image of the lungs. Alternatively, the first pulmonary image may be an inspiratory scan of lungs and the second pulmonary image may be of the lungs at expiration. Alternatively, the second pulmonary image may be a Jacobian image. The first image may be associated with a first point in time and the second image may be associated with a second point in time, the first point in time different from the second point in time. The generative neural network model may be constructed using a generative neural network framework comprising a first convolutional neural network (CNN) as an image generator and a second convolutional neural network (CNN) as an image evaluator. The generative neural network model may be constructed using generative adversarial networks (GANs).

According to another aspect, a system is provided. The system includes a processor, a non-transitory machine readable medium, a plurality of instructions stored on the non-transitory machine readable medium which upon execution by the processor cause the processor to evaluate a single CT scan image to directly estimate pulmonary function. The plurality of instructions may apply a generative neural network model to produce a generated image and the single CT scan image and the generated image are used to directly estimate the pulmonary function. The single CT scan image and the generated image may be of the lungs at different volumes. The generative neural network model may be a generative adversarial network (GANs) model. The GANs model may be trained using an ensemble of pre-trained weak generative learners. The pulmonary function may include regional lung deformation.

According to another aspect a system includes a processor, a non-transitory machine readable medium, and a plurality of instructions stored on the non-transitory machine readable medium which upon execution by the processor cause the processor to create a generated biomedical image of biological tissue based on a single scan of the biological tissue and perform an evaluation of the biological tissue based on the generated biomedical image and the single scan of the biological tissue. The plurality of instructions may apply a generative neural network model to create the generated image. The generative neural network model may be a generative adversarial network (GANs) model. The GANs model may be trained using an ensemble of pre-trained weak generative learners.

According to another aspect, knowing that pulmonary biomechanical markers have shown significant promise towards understanding the complex nature of COPD, but recognizing that he registration methods used to compute these parameters incur large computational cost and rely on multi-volume computed tomography scans, a registration-independent, adversarial learning approach to estimate three different measures of regional lung deformation directly from the expiratory computed tomography scan is provided.

According to another aspect of the present disclosure, regional measures of lung function used for assessing chronic obstructive pulmonary disease (COPD) are typically computed by registering chest computed tomography (CT) scans acquired at different volumes, typically end-inspiration and end-expiration volumes. Since this process inherently requires CT scans at different volumes, it is not possible to estimate the local measures of lung function for patients where multiple volume scans are unavailable or are impossible to acquire. Such patients include later stage COPD subjects with reduced lung function, subjects with cancer, and patients requiring a lung transplant. Another disadvantage of acquiring multiple CT scans is the exposure to radiation dosage which is a risk factor for cancer. The present disclosure provides a neural network-based generative modeling system that can directly convert a single CT scan (acquired at expiration or inspiration, for example) directly to local measures of lung function, some of the most prominent and clinically relevant of which include, the local tissue expansion measure (Jacobian) and parametric response mappings (PRM). This approach requires a single CT to compute these measures and can be scaled to larger cohorts where subjects have CT scans acquired at single volumes.

According to another aspect, a process-based system has been designed to compute local lung tissue expansion from a single CT scan, in contrast to traditional approaches that require multiple CT scans acquired at two or more different volumes. Our system can also be used to convert an end-expiratory CT scan to the corresponding end-inspiration CT scan. Our system would eliminate the need for multiple scans of the same patients to assess lung function and air trapping, thereby shortening diagnosis time, cost, and reducing exposure to radiation dosage. Our approach is an image registration independent alternative to traditional methods for estimating lung function from multiple CT scans. Instead, we propose a generative learning framework that can be used to directly convert a CT scan at expiration either directly to an inspiratory scan (so that parametric response maps could be generated from them) or to a Jacobian image (so that local tissue mechanics could be studied). The system architecture comprises two different generative neural network architectures that are used to generate these images using a single scan. Unlike the traditional registration-based approaches, our system relies on just one scan. The system architecture comprises of two convolutional neural networks (CNNs)—one is the image generator, while the other is image evaluator. Initially, the system is trained by ground truth Jacobians or TLCs to be generated by the generator. Once the system training is complete, the models can now be used to generate these local measures of lung function.

According to another aspect, a system is provided which includes a processor, a non-transitory machine readable medium, and a plurality of instructions stored on the non-transitory machine readable medium which upon execution by the processor cause the processor to: evaluate a single functional image to directly estimate pulmonary function, the single functional image acquired by one of computed tomography (CT), hyper-polarized gas magnetic resonance imaging (MRI), positron emission tomography (PET), and single photon emission computed tomography (SPECT).

BRIEF DESCRIPTION OF THE DRAWINGS

Illustrated embodiments of the disclosure are described in detail below with reference to the attached drawing figures, which are incorporated by reference herein, and where:

FIG. 1A illustrates the traditional method that required CT scans at two different volumes that are registered by a DIR framework for computing the displacement vector field $\phi(\bullet)$. FIG. 1B illustrates the proposed generative modeling framework for directly estimating pulmonary function from a single CT scan.

are then used to compute perceptual loss for the particular view. A similar approach is used for other two views and the overall multiview perceptual similarity is then aggregated.

Figure 13:
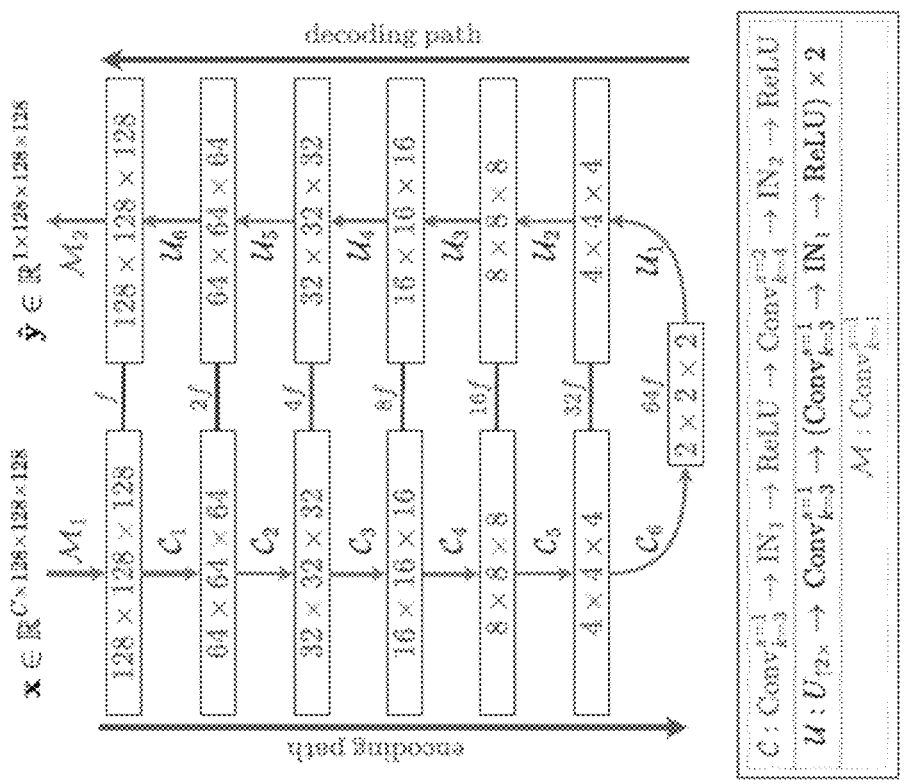

FIG. 13 shows a modified UNet-like architecture for the generator. The model begins by generating a feature map of size f which is then increased upto 64 f at the end of the bottleneck. Output of the model is a single channel patch with same spatial dimensions. Each downsampling block C was composed of 3D convolutions followed by instance normalization (IN) and rectified linear units as activations (ReLU). Similar blocks were used for discriminator model as well. Within the upsample block $\mathcal{U}$ the feature maps were first upsampled using trilinear interpolation operator $\mathcal{U}_{\uparrow 2\times}$ followed by 3D convolutions. For generator f=32 and discriminator f=8.

Figure 14:
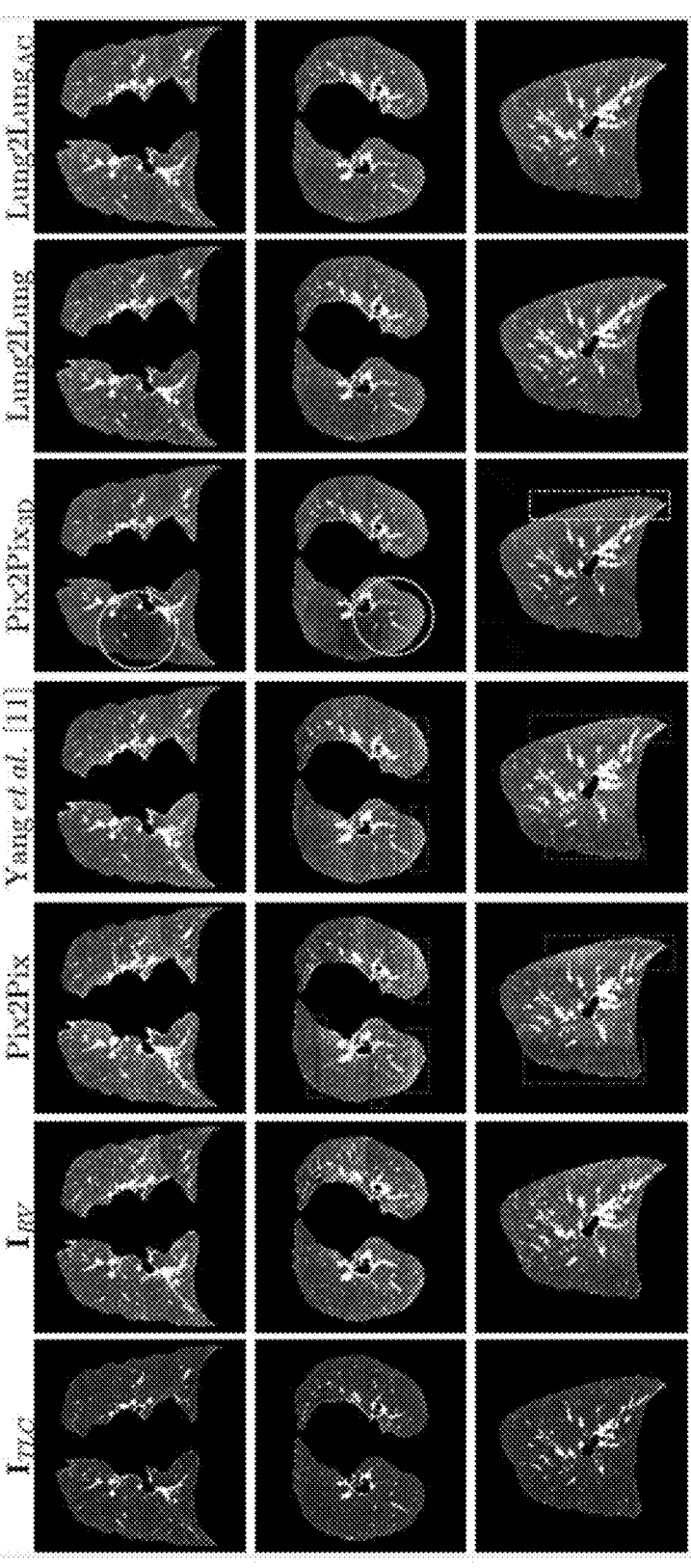

FIG. 14 shows Visual comparison of representative samples shown across coronal, axial, and sagittal views from the same subject. We compare results from Lung2Lung with two slice-based methods, Pix2Pix [34] and the work of Yang et al. [12], and a volumetric method Pix2Pix3D. Both 2D methods present with discontinuities across axial and sagittal view (red), since they were trained on mid-coronal slices, while Pix2Pix3D produced blurry results (yellow). We also show visual slices after AC-based refinement.

Figure 15:
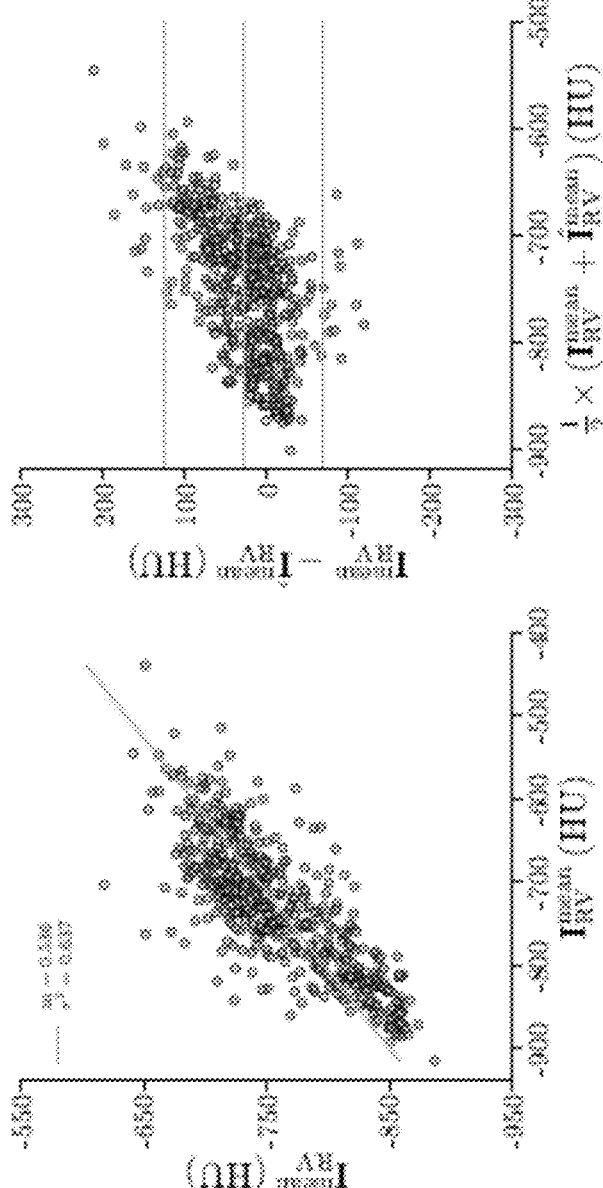

FIG. 15 shows regression analysis with corresponding Bland-Altman plot for comparison between means of real and synthetic RV scans.

Figure 16:
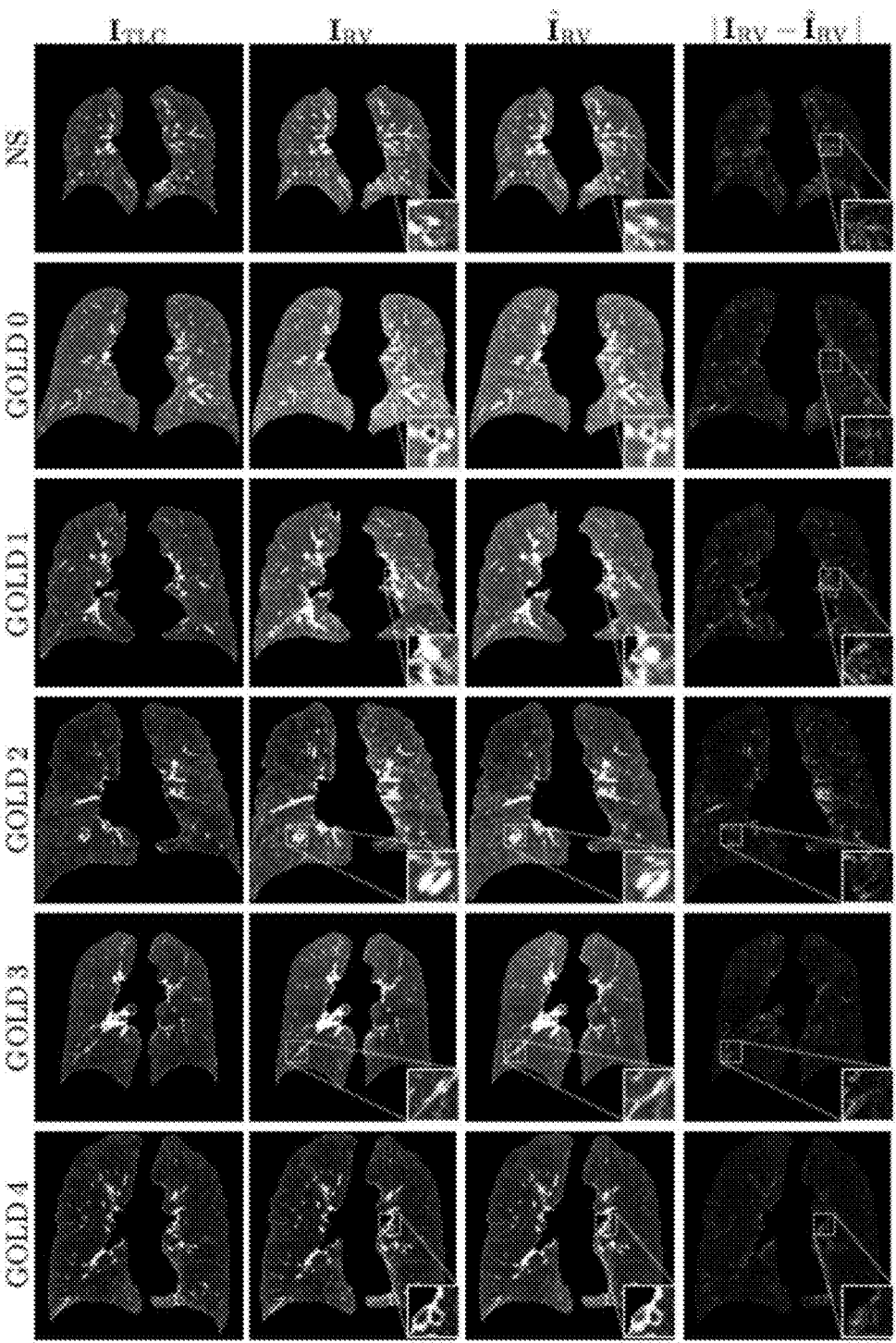

FIG. 16 shows qualitative performance analysis across varying COPD severity.

Figure 17:
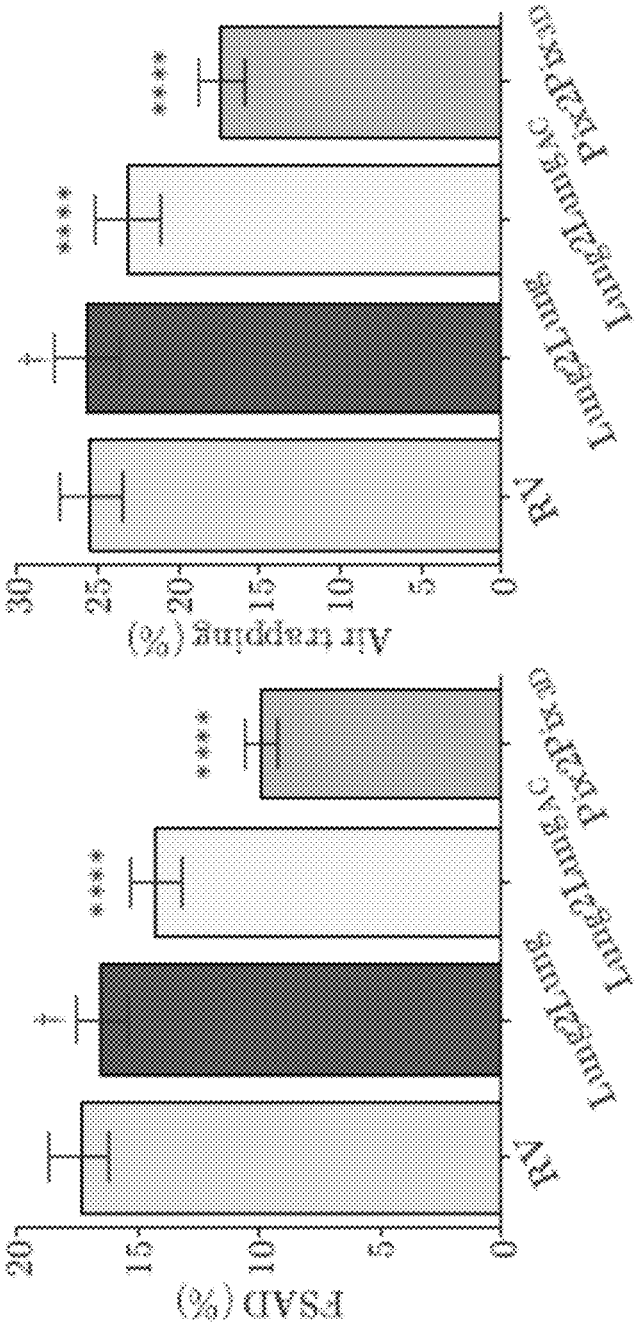

FIG. 17 shows quantitative comparison of fSAD and air-trapping extracted from both real and synthetic RV scans. We compared values from three different models. '†' indicated p>0.05 and '****' indicated p<0.0001.

Figure 18:
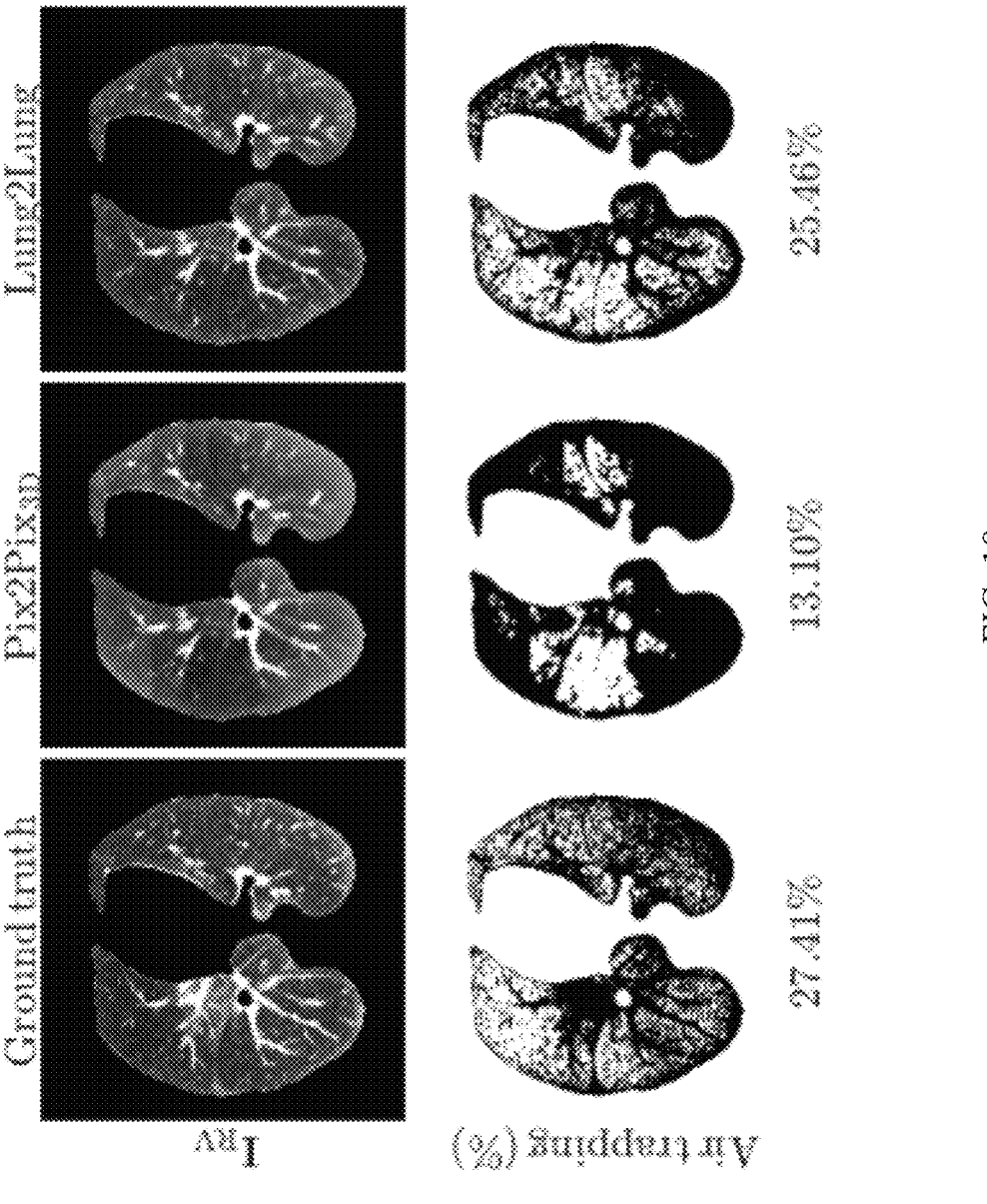

FIG. 18 shows impact of multiview perceptual similarity (MEAL) on visual distribution of air-trapping. Pix2Pix3D underestimated overall percent air-trapping, while Lung2Lung was better able to capture image texture/style which improved single-volume estimation of air-trapping.

Figure 19:
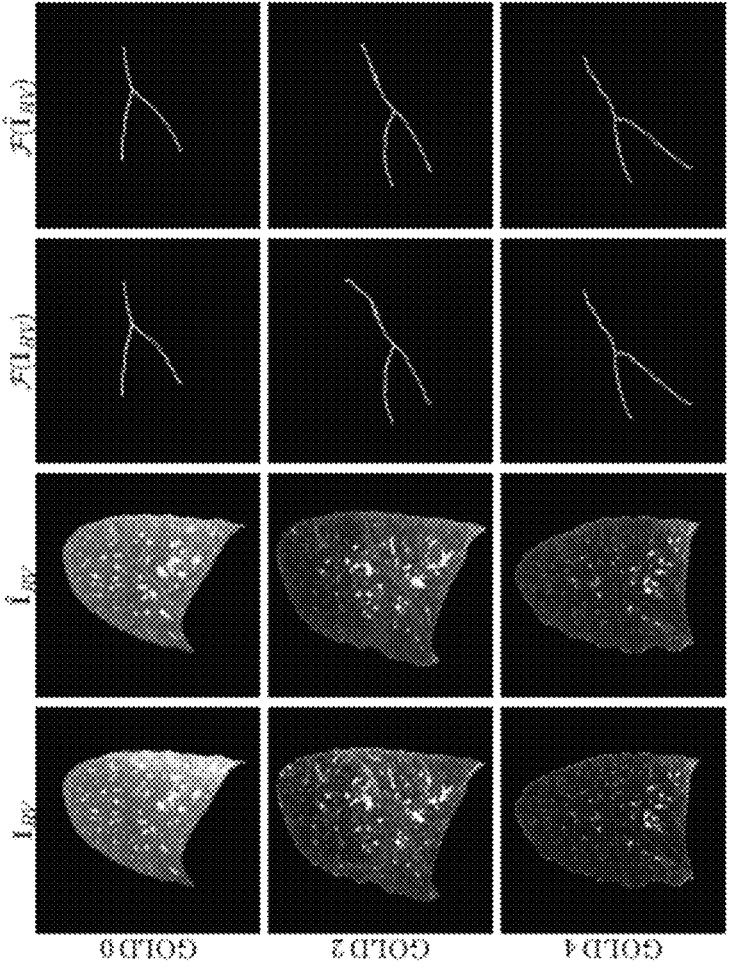

FIG. 19 shows fissure segmentations using a state-of-the-art fissure segmentation model, FissureNet [45] $\mathcal{F}$ ($\bullet$). on real $\mathbf{I}_{RV}$ and synthetic $\hat{\mathbf{I}}_{RV}$ samples, shown on sagittal slices.

Figures 20, 21:
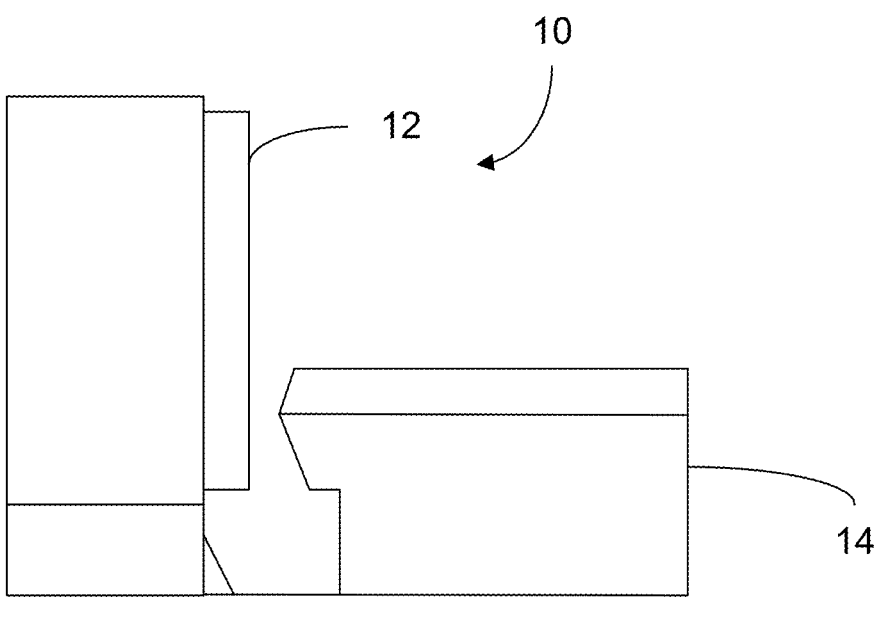

FIG. 20 illustrates one example of an imaging system.

FIG. 21 illustrates one example of a control system for an imaging system.

FIG. 22 illustrates one example of a methodology.

BRIEF DESCRIPTION OF TABLES

Table 1. Distribution of COPD severity, defined by GOLD (Vestbo et al. (2013)), across disjoint training and testing datasets. Asymptomatic smokers or GOLD0 subjects constitute the largest sub-group among different disease severities.

Table 2. Distribution of COPD severity, defined by GOLD, across disjoint training and testing datasets.

Table 3. Quantitative performance evaluation of Lung2Lung across 512 subjects from the SPIROMICS cohort, in contrast to various state-of-the-art 2D and 3D generative frameworks. The 3d volumetric frameworks performed better than 2d planar methods, indicated by PSNR, SSIM, MAE (HU), SPEARMAN'S correlation, and NMSE. WILCOXON signed rank test was used to assess differences between the means of all evaluation metrics, where Lung2Lung with auto-context was selected as reference. Before performing the WILCOXON test, we evaluated all metrics for normality using shapiro-wilk test. A p-value less than 0.05 was considered to be significant, where '' and '*' indicated p<0.001 and p<0.0001, respectively.

Table 4. Performance evaluation of the Lung2Lung framework (with auto-context) across varying degrees of disease severity, as defined by the global initiative for chronic obstructive lung disease (GOLD).

DETAILED DESCRIPTION

Before invention embodiments are disclosed and described, it is to be understood that no limitation to the particular structures, process steps, or materials disclosed herein is intended, but also includes equivalents thereof as would be recognized by those ordinarily skilled in the relevant arts. It should also be understood that terminology employed herein is used for the purpose of describing particular examples only and is not intended to be limiting. The same reference numerals in different drawings represent the same element. Numbers provided in flow charts and processes are provided for clarity in illustrating steps and operations and do not necessarily indicate a particular order or sequence. Unless defined otherwise, all technical and scientific terms used herein have the same meaning as commonly understood by one of ordinary skill in the art to which this disclosure belongs.

1. Introduction

Here we disclose an ensemble-driven, generative, adversarial confidence learning (ACL) framework for directly translating anatomical structures of the lung parenchymato different measures of lung function, thereby eliminating the need for inspiratory-expiratory volume pairs.

2. Background 2.1 Image Registration

Figure 1A:
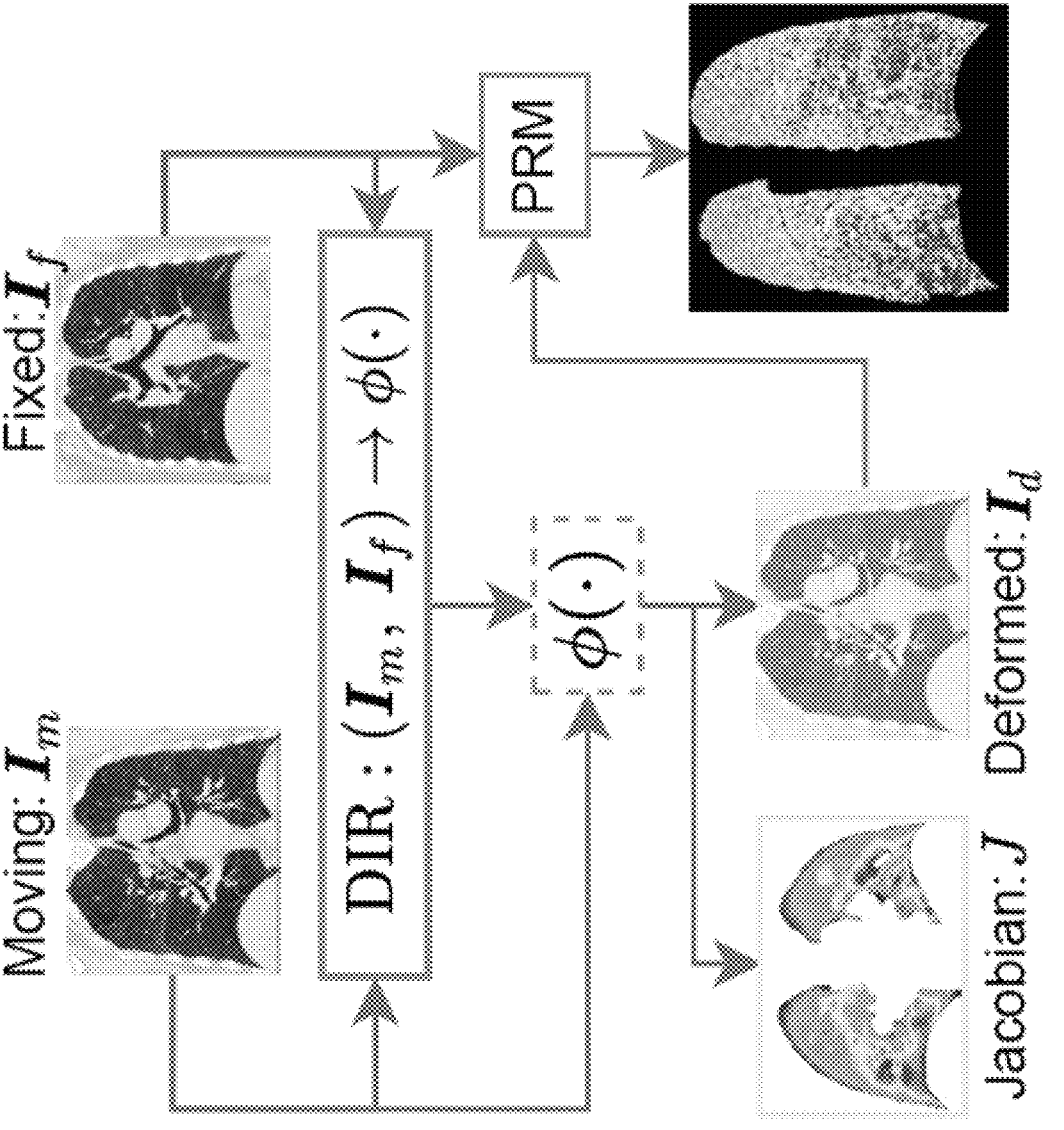
FIG. 1A and FIG. 1B provide a comparison between traditional image registration framework for pulmonary function estimation vs. the proposed method.

Image registration is the process of finding a point-to-point correspondence between two image volumes FIG. 1a. Typically, it works by learning a transformation $\phi(\bullet)$: $\mathbb{R}^3 \to \mathbb{R}^3$ that could transform the coordinates of a moving image $I_m$: $\mathbb{R}_3 \to \mathbb{R}$, to the coordinate system of the fixed image $I_f$: $\mathbb{R}^3 \to \mathbb{R}$. Let (x', y', x') and (x, y, z) be coordinates of the newly deformed image $I_d$ and moving image $I_m$ respectively, then the transformation can be used to map the coordinates as (x', y', x')=$\phi$(x, y, z). The intensity value of $I_d$ at (x', y', x') can thus be determined from the pullback of $I_m$ at (x, y, z):

$$I_d(x', y', x') = I_m(x, y, z) = I_m \circ \phi^{-1}(x', y', x'), \qquad (1)$$

where $I_d = I_m \circ \phi^{-1}$(x, y, z). Conventional DIR methods use a variational framework for determining $\phi(\bullet)$, which can in general, be posed as the following optimization problem:

$$\{\hat{\phi}\} = \underset{\phi}{\operatorname{argmin}} \left\| I_m^{\circ} \varphi - 1 - I_f \right\|_p + \Gamma(\varphi), \qquad (2)$$

where the first term quantifies the intensity differences between the deformed and the fixed image, while $\Gamma(\phi)$ ensures a smooth transformation by regularizing it. FIG. 1a shows a typical image registration pipeline used for computing two commonly used measures of local lung function—the PRM and J.

2.2. Registration-Derived Regional Tissue Expansion

Reinhardt et al. (2007, 2008) used displacement vector field obtained after registering the 3D CT scans acquired at different volumes for estimating local lung expansion (FIG. 1a). Jacobian determinant J of the displacement vector field, simply called Jacobian, was used to quantify regional tissue expansion. For a three-dimensional vector displacement field $\phi(x)=(\phi_1(x), \phi_2(x), \phi_3(x))\in \mathbb{R}^3$ at a point $x\in \mathbb{R}^3$, the Jacobian J is given as:

$$J(\phi(x)) = \begin{vmatrix} \dfrac{\partial\phi(x)_1}{\partial x_1} & \dfrac{\partial\phi(x)_2}{\partial x_1} & \dfrac{\partial\phi(x)_3}{\partial x_1} \\ \dfrac{\partial\phi(x)_1}{\partial x_2} & \dfrac{\partial\phi(x)_2}{\partial x_2} & \dfrac{\partial\phi(x)_{23}}{\partial x_2} \\ \dfrac{\partial\phi(x)_1}{\partial x_3} & \dfrac{\partial\phi(x)_2}{\partial x_3} & \dfrac{\partial\phi(x)_3}{\partial x_3} \end{vmatrix} \qquad (3)$$

The Jacobian J measures expansion at each point $x\in \mathbb{R}^3$ of the deformed volume. A value of J=1 indicates no expansion or contraction, while J>1 indicates local expansion and J<1 indicates local contraction.

2.3. Parametric Response Mapping Measures of Lung Function

Figure 2:
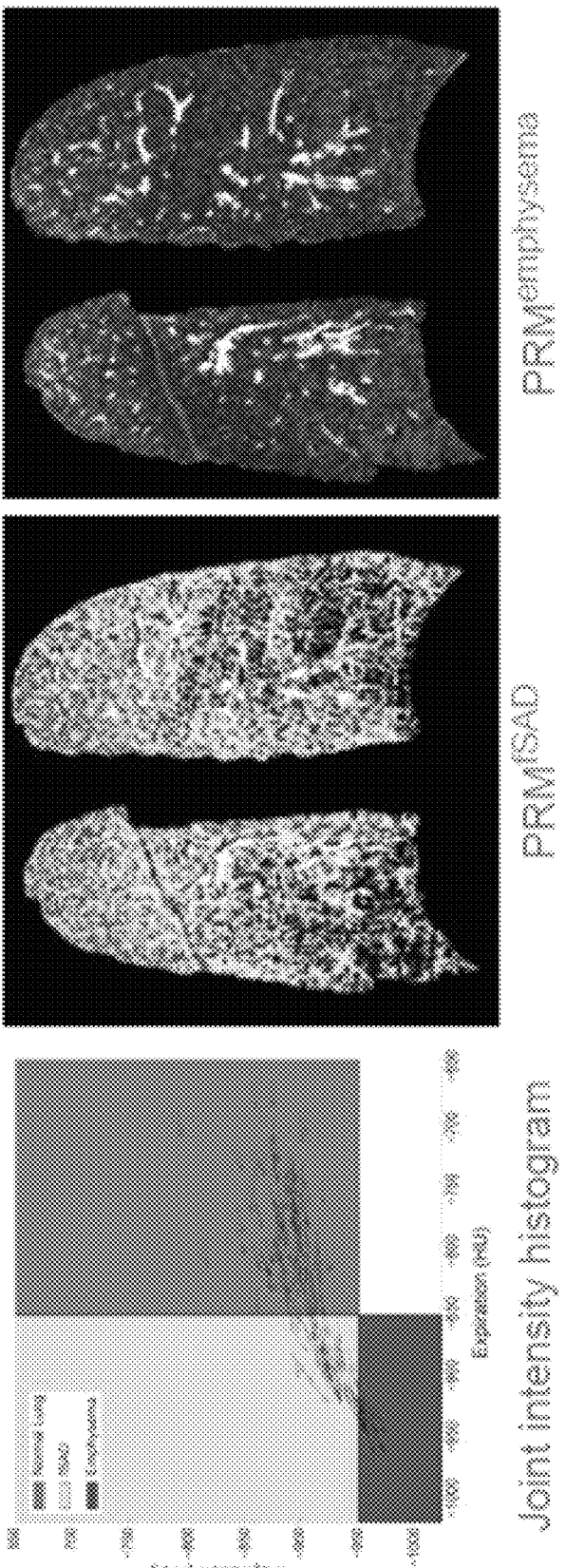
FIG. 2 shows typical examples of PRM.

Galbán et al. (2012) used image registration for matching inspiratory and expiratory CT volume pairs (FIG. 1A). The deformed expiratory and reference inspiratory CT volume pairs were used to construct a joint 2D histogram of inspiratory-expiratory CT intensities (in Hounsfield units (HU)). The histogram was thresholded to compute the PRM from the CT and they identified two thresholds for quantifying emphysema and fSAD regions across the lung—voxel intensities less than −950 HU on an inspiratory scan indicated emphysema, while voxel intensities less than −856 HU on an expiratory scan denoted fSAD. These thresholds were used to derive the spatial distribution of parenchymal tissue damage and fSAD, shown in FIG. 2.

3. Methods

Figure 1B:
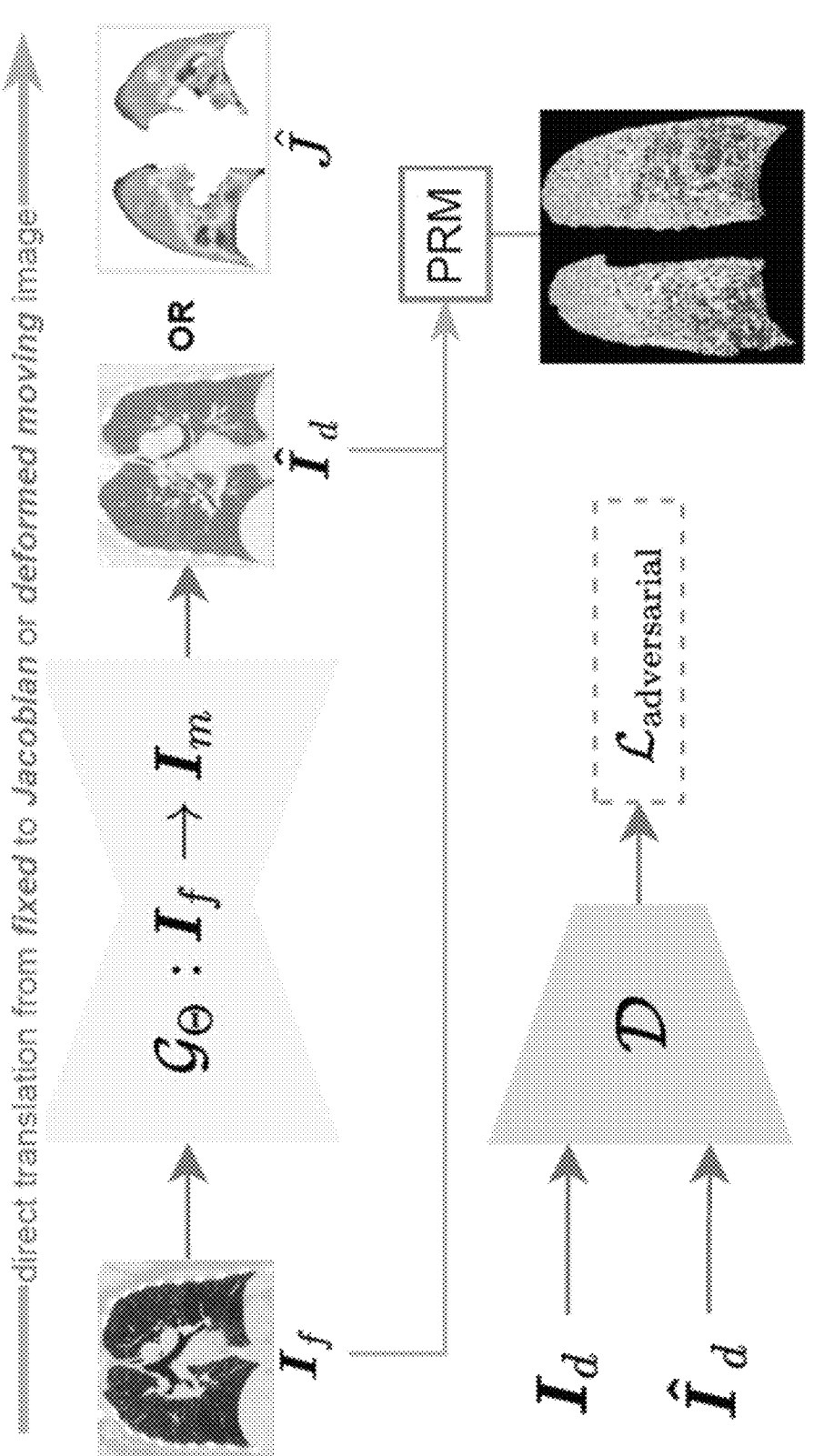

In this section, we present an ensemble-driven adversarial confidence learning framework—which we refer to as EN-LACE—for directly estimating local measures of lung function such as Jacobian and PRM (FIG. 1). Instead of using a typical dual-volume, image-registration framework for computing J or PRMs (FIG. 1a), we propose a generative adversarial learning approach for translating a CT scan at expiration, directly either to an inspiratory scan, (for PRMs) or to a J map, as shown in FIG. 1b. In doing so, we eliminate the need for breath-hold scans at inspiration and expiration for computing the aforementioned measures of local lung function. We develop a single generative modeling architecture that is used for both tasks—estimating J (for local tissue expansion) and inspiratory CT (for deriving PRMs) from expiratory CT volumes. We propose to use an ensemble of pre-trained weak generative models as a prior to an adversarial learning framework for eventually mapping an expiratory CT slice to J or inspiratory CT, shown in FIG. 3.

3.1. Generative Adversarial Networks

GANs are a well-known, unsupervised learning tool for generating perceptually realistic images, and their application for various medical image synthesis tasks is widespread. The learning framework of a GAN consists of two different networks that are trained to compete against each other until they reach Nash's equilibrium (Goodfellow et al. (2014)). The generator $\mathcal{G}$ : z→y tries to capture the target distribution $\mathbb{P}_y$ by mapping a random noise vector z to a target image y~$\mathbb{P}_y$. The images generated by $\mathcal{G}$ are then evaluated by a second model called the discriminator $\mathcal{D}$, simultaneously trained to learn if the samples are real (i.e., sampled from $\mathbb{P}_y$) or generated. Typically, $\mathcal{D}$ is a binary classifier that outputs the probability of a sample (real or generated) being sampled from the target distribution $\mathbb{P}_y$. While $\mathcal{D}$ is optimized to maximize this probability, the generator $\mathcal{G}$ tries to minimize it, a dynamic modeled by the minimax game stated as:

$$\min_{\mathcal{G}} \min_{\mathcal{D}} \mathcal{L}_{GAN}(\mathcal{G}, \mathcal{D}) = \mathbb{E}_y[\log \mathcal{D}(y)] = +\mathbb{E}_z[\log(1 - \mathcal{D}(\mathcal{G}(z)))]. \quad (4)$$

The discriminator D minimizes cross entropy loss which is known to be responsible for vanishing gradients propagated back to the generator, thereby resulting in unstable GAN training. Mao et al. (2017) demonstrated that by simply replacing the negative log-likelihood in Eq. 4 with least squares loss, the problem of vanishing gradients could be mitigated. The objective of least squares GAN (LSGAN) can thus be stated as:

$$\min_{\mathcal{G}} \min_{\mathcal{D}} \mathcal{L}_{LSGAN}(\mathcal{G}, \mathcal{D}) = -\mathbb{E}_y\left[(\mathcal{D}(y) - 1)^2\right] - \mathbb{E}_y\left[(\mathcal{D}(G(z)))^2\right]. \quad (5)$$

In our work, we propose to use the LSGAN framework for improving stability during GAN training.

3.4. Conditional GANs for Image-to-Image Translation

The aforementioned formulation of a minimax objective function is not suitable for mapping an image x to another im-age y. We extend the unsupervised LSGAN to pix2pix—an image-conditional framework for paired image-to-image translation (Isola et al. (2017)). Let $X \subseteq \mathbb{R}^{H \times W \times C}$ and $\mathcal{Y} \subseteq \mathbb{R}^{H \times W \times C}$ be the source and target domains, respectively; and let there be a one to one mapping between the two sets such that the overall dataset can be described as a set of ordered tuples $$D = \{(x_i, y_i)\}_{i=1}^N \in \mathbb{R}^{H \times W \times C}$$

where $x \in X$, $y \in \mathcal{Y}$, and N is the size of dataset. Instead of mapping a random noise vector z to an output image y, the generator $\mathcal{G}: x \rightarrow y$ translates an input image x to the output y, which is then evaluated by a discriminator $\mathcal{D}$. The LSGAN objective in Eq. 5 can be extended to an image-conditional framework (cGAN) as:

$$\mathcal{L}_{cGAN} = -\mathbb{E}_y\left[(\mathcal{D}(x, y) - 1)^2\right] - \mathbb{E}_x\left[\mathcal{D}(\mathcal{G}(zx))^2 \mathcal{D}(\mathcal{G}(z))^2\right], \quad (6)$$

where $\mathcal{G}(x) = \hat{y} \in \mathbb{R}^{H \times W \times C}$ is the generated image, and both $\mathcal{G}$ and $\mathcal{D}$ are conditioned on input image x in Eq. 6. Note that, the vanilla pix2pix GAN used negative log-likelihood framework presented in Eq. 4 which has been replaced by a least squares setting in Eq. 6. In addition to the adversarial feedback provided to generator by discriminator, the pix2pix generator minimizes $L_1$ distance between the target y and generated samples $\hat{y}$, defined as:

$$\mathcal{L}_{L_1} = \mathbb{E}_{x,y}[\|y - \hat{y}\|_1] = \mathbb{E}_{x,y}[\|y - \mathcal{G}(x)\|_1], \quad (7)$$

Regularizing the L1 distance is robust to outliers but tends to encourage sparse representations that are unable to capture subtle details during synthesis. The $L_2$ distance, on the other hand, is sensitive to outliers and produces blurry results. Chen and Koltun (2014) demonstrated the generalized Charbonnier loss to be better than $L_1$ and $L_2$ distances for a challenging task like depth reconstruction. We studied the performance of $L_1$ distance against the Charbonnier loss function, that can be stated as:

$$\mathcal{L}_{Ch}(x, y) = \mathbb{E}_{x,y}[\rho(y - \mathcal{G}(x))] = \mathbb{E}_{x,y}[\rho(y - \hat{y})], \quad (8)$$

where $\rho(t) = \sqrt{t^2 + \epsilon^2}$ and $\epsilon$ is a very small constant set to $10^{-6}$ The overall loss function minimized by $\mathcal{D}$ can be written as:

$$\mathcal{L}_{adv}^{\mathcal{D}}(x, y) = \mathcal{L}_{MSE}(\mathcal{D}(x, y), 1) + \mathcal{L}_{MSE}(\mathcal{D}(x, \mathcal{G}(x)), 0), \quad (9)$$

where $\mathcal{L}_{MSE}$ E is the least squares loss, $\mathcal{D}(x,y)$ is the discriminator output for y compared to a tensor of ones, $\mathbb{1} \in \mathbb{R}^{hH \times wW}$ such that h<Hand w<W. Similarly, $\mathcal{D}(x, \mathcal{G}(x))$ is the discriminator output for synthetic sample $\mathcal{G}$ g(x)=$\hat{y}$ compared to a tensor of zeros, $\mathbb{0} \in \mathbb{R}^{Hh \times Ww}$. This is different from a conventional discriminator, where the output is a single number rather than a tensor, and is called the Patch-GAN discriminator (Isola et al. (2017)). It provides feedback for images patches of size h×w instead of a single score for the entire image. The overall loss minimized by the generator can be expressed as:

$$\mathcal{L}^{\mathcal{G}}(x, y) = \mathcal{L}_{MSE}(\mathcal{D}(x, \mathcal{G}(x)), 1) + \lambda \mathcal{L}_{Ch}(x, y). \quad (10)$$

In this case, the discriminator's adversarial feedback is compared to a tensor of ones $\mathbb{1} \in \mathbb{R}_{hH \times Ww}$, rather than zeros since generator tries to fool the discriminator. We propose to replace batch normalization with instance normalization and show that it significantly improves the performance of our model (Ulyanov et al. (2016)).

3.3. Adversarial Confidence Learning

GANs trained on large datasets with stability encourage perceptually realistic images. While the qualitative results show improvement with stability, the quantitative performance does not improve very often. The loss minimized by discriminator either quantifies feedback for global structure of the image, and hence is unable to capture subtle details within it. Xia et al. (2021) proposed a multi-resolution discriminator for pro-viding feedback on smaller details often ignored by a typical discriminator. The multi-scale discriminator, however, entails a larger memory demand for end-to-end training, depending on the number of resolutions used. Recently, Nie and Shen (2020)proposed an adversarial confidence learning approach for providing pixelwise feedback across the generated image. Similar to this, we propose to use a UNetbased confidence network instead of a conventional discriminator. In addition to capturing the global structure of an image, the voxelwise feedback is designed to ensure local image consistency thereby purported to increase the overall quantitative performance of the adversarial model. Instead of using negative-likelihood (Nie and Shen (2020)), we use a least squares confidence network for improved stability and performance. The proposed discriminator model minimizes a similar objective in Eq. 9, except that the $\mathcal{D}(x, y) = C_y \in \mathbb{R}^{H \times W}$ and D(x, G(x))=$C_{\hat{y}} \in \mathbb{R}^{H \times W}$ are pixelwise adversarial confidence maps for real and generated images, respectively.

3.4. Self-attention for Context-Aware Synthesis

Generative models are local in nature and synthesize image points as a function of their neighborhoods. The convolutional generative models are thus unable to capture the global details within an image. To model long-range dependencies between pixels a self-attention module was proposed to construct the generator of a GAN (SAGAN) (Zhang et al. (2019)). The self-attention module learns a probabilistic map of weights to determine the global contribution of each point within the feature map. This is done by a sequence of transformations applied to the feature map from previous layer $x_{L-1} \in \mathbb{R}^{H \times W \times C}$, where C is the number of channels output by the previous layer. The input is first transformed by two single-strided convolutional operators $f(x_{L-1}) = W_f x_{L-1} \in \mathbb{R}^{H \times W \times \bar{C}}$ and $g(x_{L-1}) = W_g x_{L-1} \in \mathbb{R}^{H \times W \times \bar{C}}$. Next, the transformed features maps are passed through softmax for computing $\beta \in \mathbb{R}^{HW \times HW}$:

$$\beta_{j,i} = \frac{\exp(S_{ij})}{\sum_{i=1}^{HW} \exp(S_{ij})}, \tag{11}$$

where $sS_{ij} = f(x_{L-1})^T g(x_{L-1})$. The attention map $o \in \mathbb{R}^{H \times W \times C}$ is then computed by the following expression:

$$o_j = \sum_{i=1}^{HW} \beta_{j,i} h(x_{L-1}), \tag{12}$$

where $h(x_{L-1}) = W_h x_{L-1}$ is a linear embedding of the same dimension computed by a convolutional operator. The output of the self-attention module is determined by scaling the attention map by a parameter $\gamma$ and adding it to the feature maps from the previous layer $x_{L-1}$, given as:

$$y = o\gamma + x_{L-1} \in \mathbb{R}^{H \times W \times C}. \tag{13}$$

4.2. Ensemble-Driven Confidence Learning (ENLACE)

Figure 3:
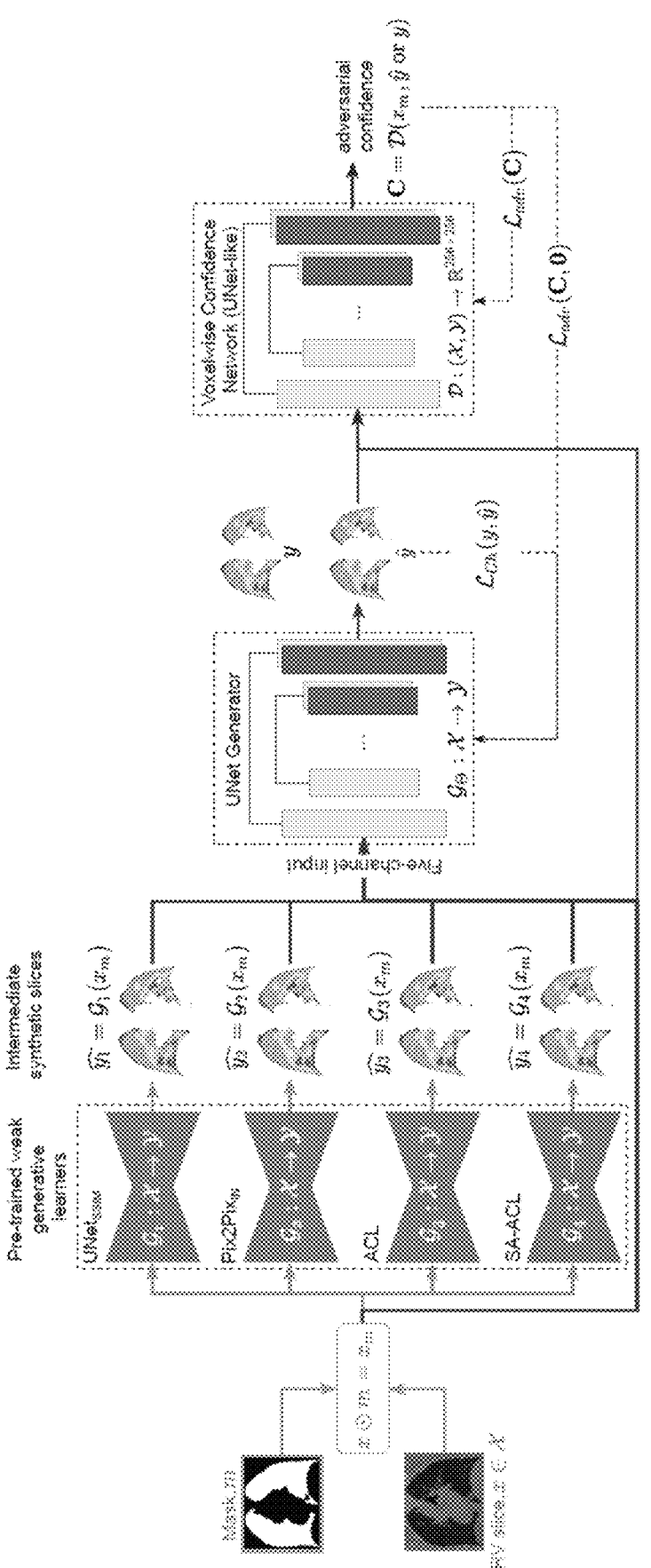
FIG. 3 is an overview of the proposed method.
Figure 4:
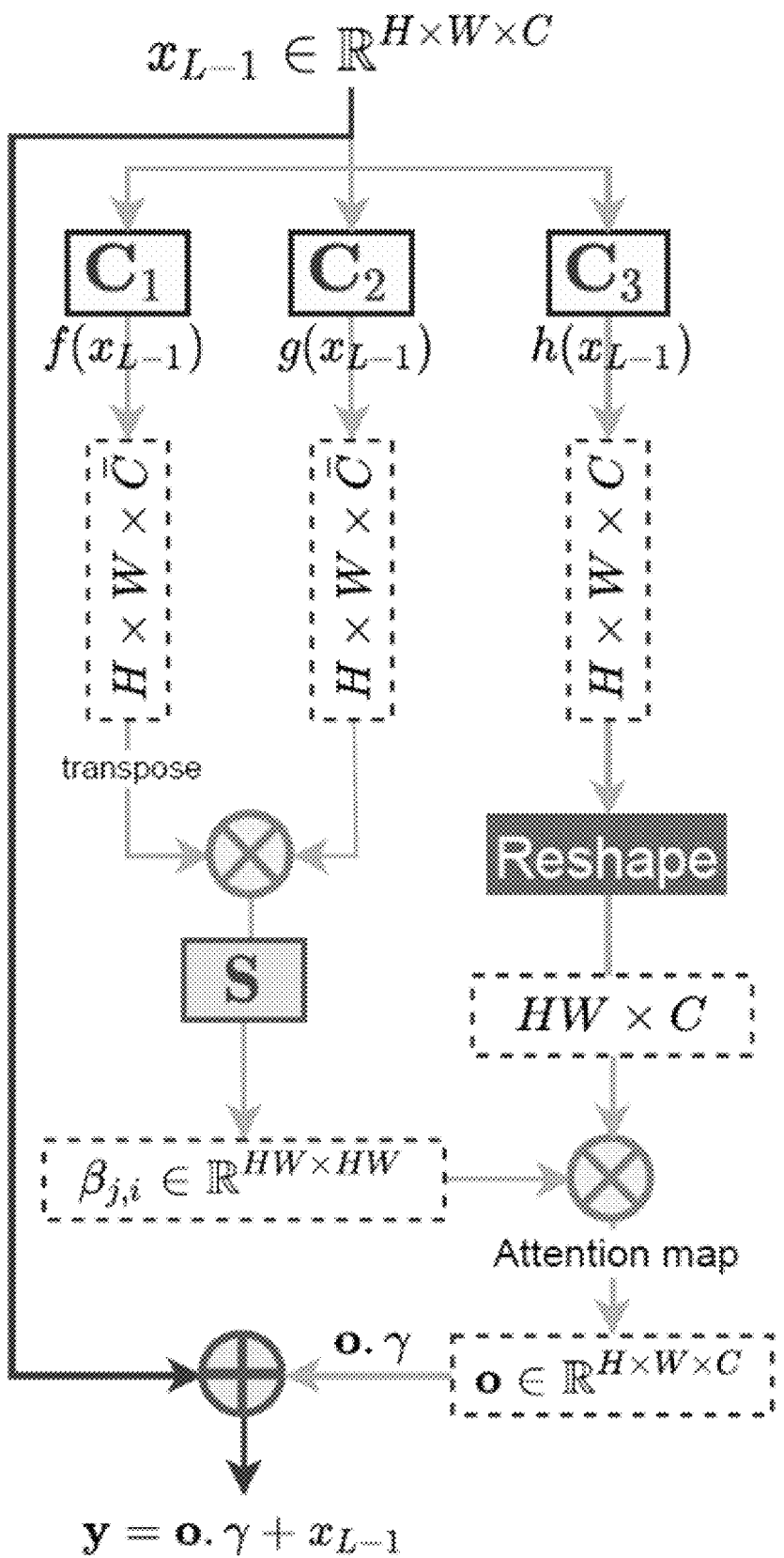
FIG. 4 is a self-attention module.

The proposed strategies including least-squares adversarial feedback, Charbonnier penalty for image intensities, instance normalization for improved style-transfer, adversarial confidence maps, and self-attention are aimed to improve GAN stability during training, enhance perceptual quality of the generated images, and provide quantitative performance gains. Since GANs do not attempt to directly learn the distribution of target samples $\mathbb{P}_y$, they always remain vulnerable to problems such as mode collapse or entirely missing modes. Ensemble methods, such as adaptive boosting were used to alleviate the missing modes problem, and were shown to have better generalization as compared to generative models trained alone (Tolstikhin et al. (2017)). We proposed to train an ensemble GAN driven by an ensemble of pre-trained weak learners, as shown in FIG. 3. The intermediate outputs of the pre-trained generative models act as suitable priors for finally training the ACL-based ensemble model.

3.5.1. Generator and Discriminator Architecture

Figure 5:
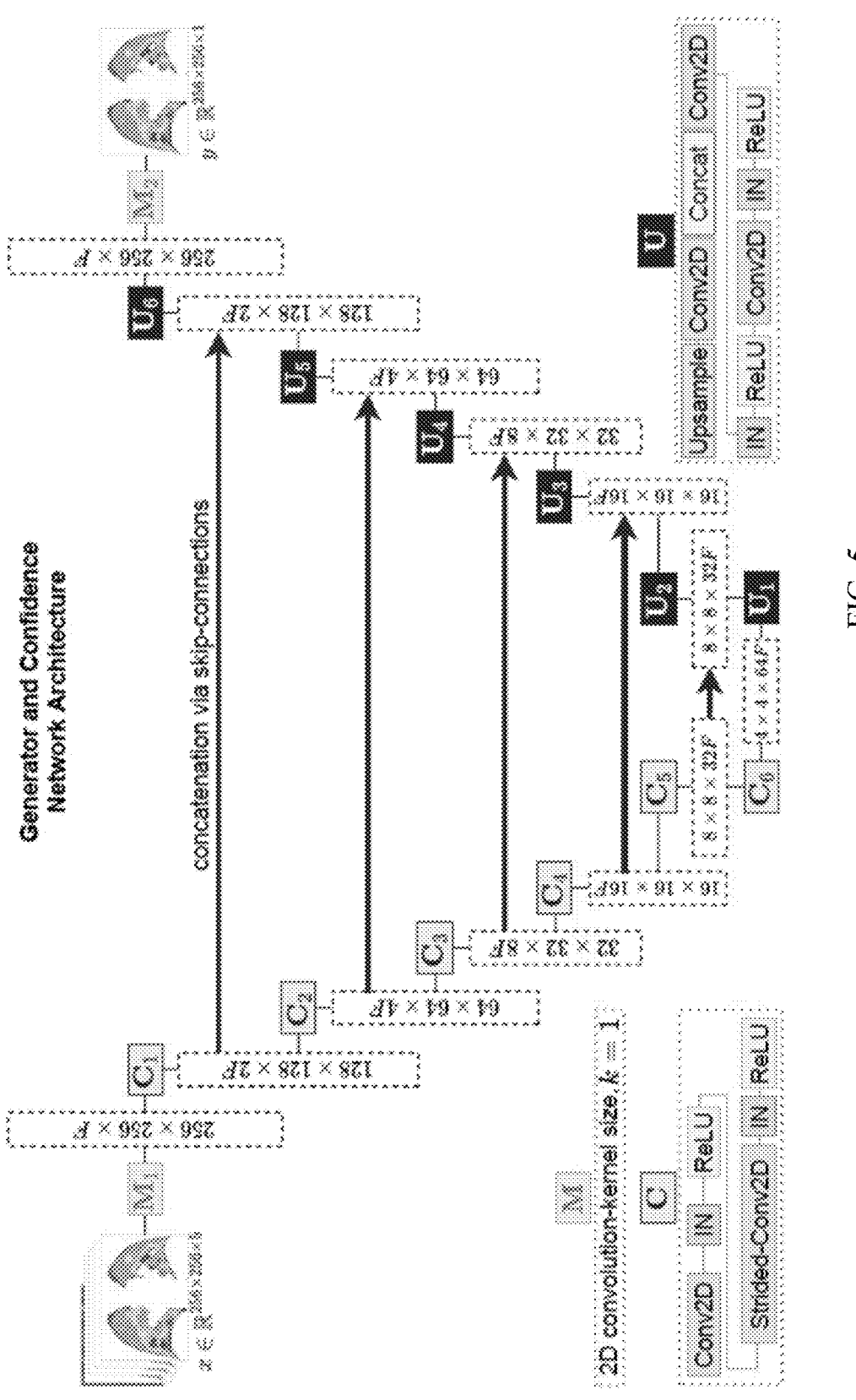
FIG. 5 is a scheme shows the generator architecture.
Figure 6:
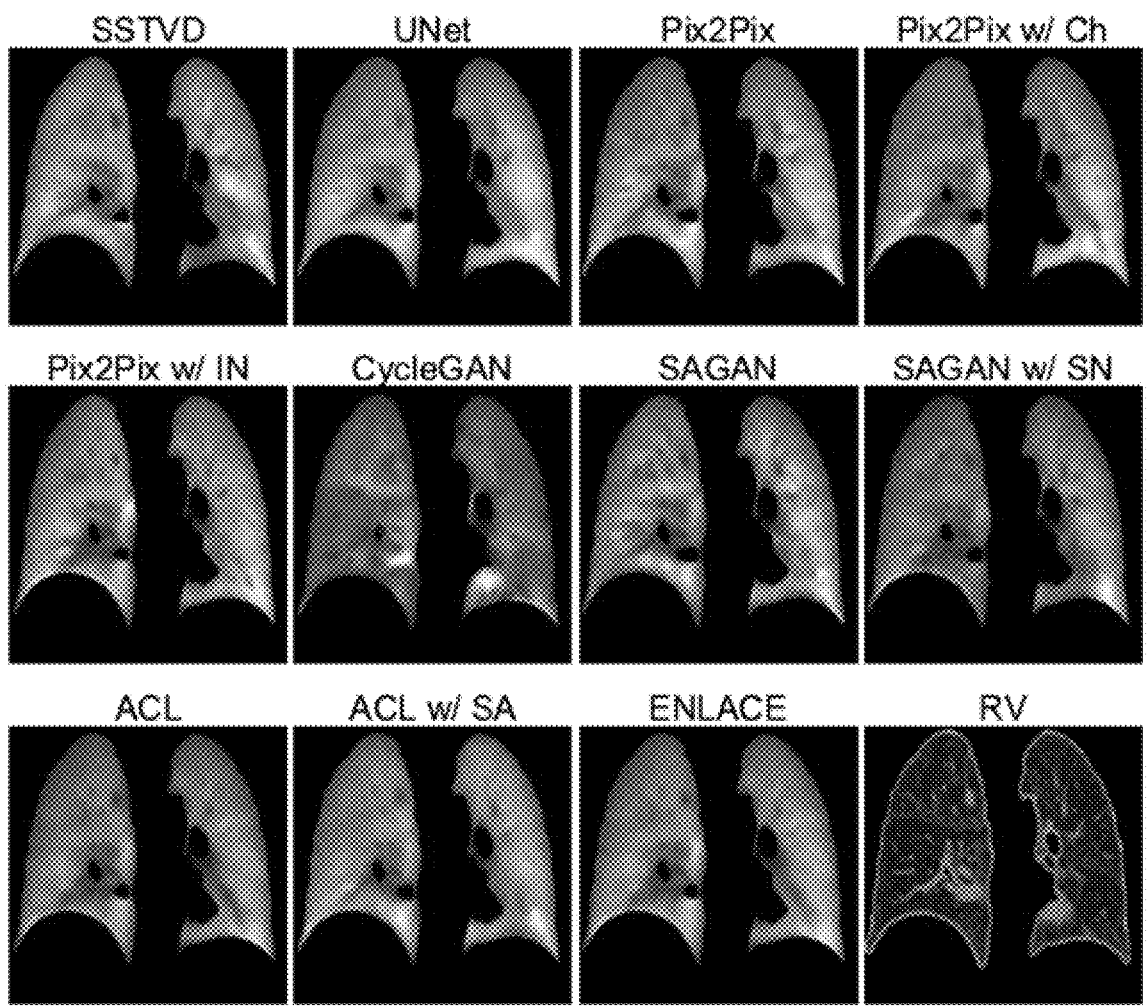
FIG. 6 shows qualitative results for estimating pulmonary function maps from residual volume (RV) CT scan, a comparison across different methods.
Figure 7:
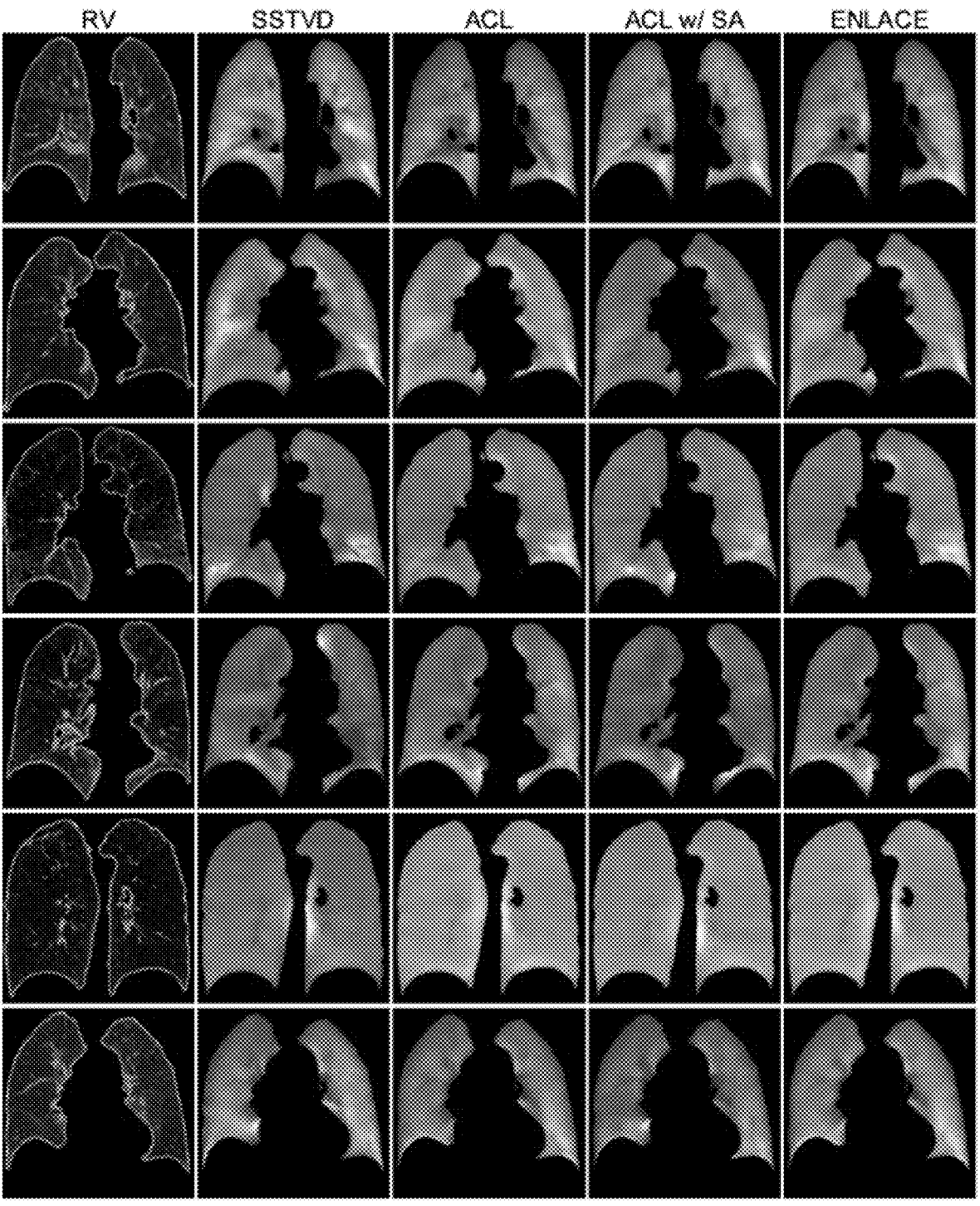
FIG. 7 shows that Jacobian maps generated by best three generative methods across different COPD GOLD stages.
Figure 8:
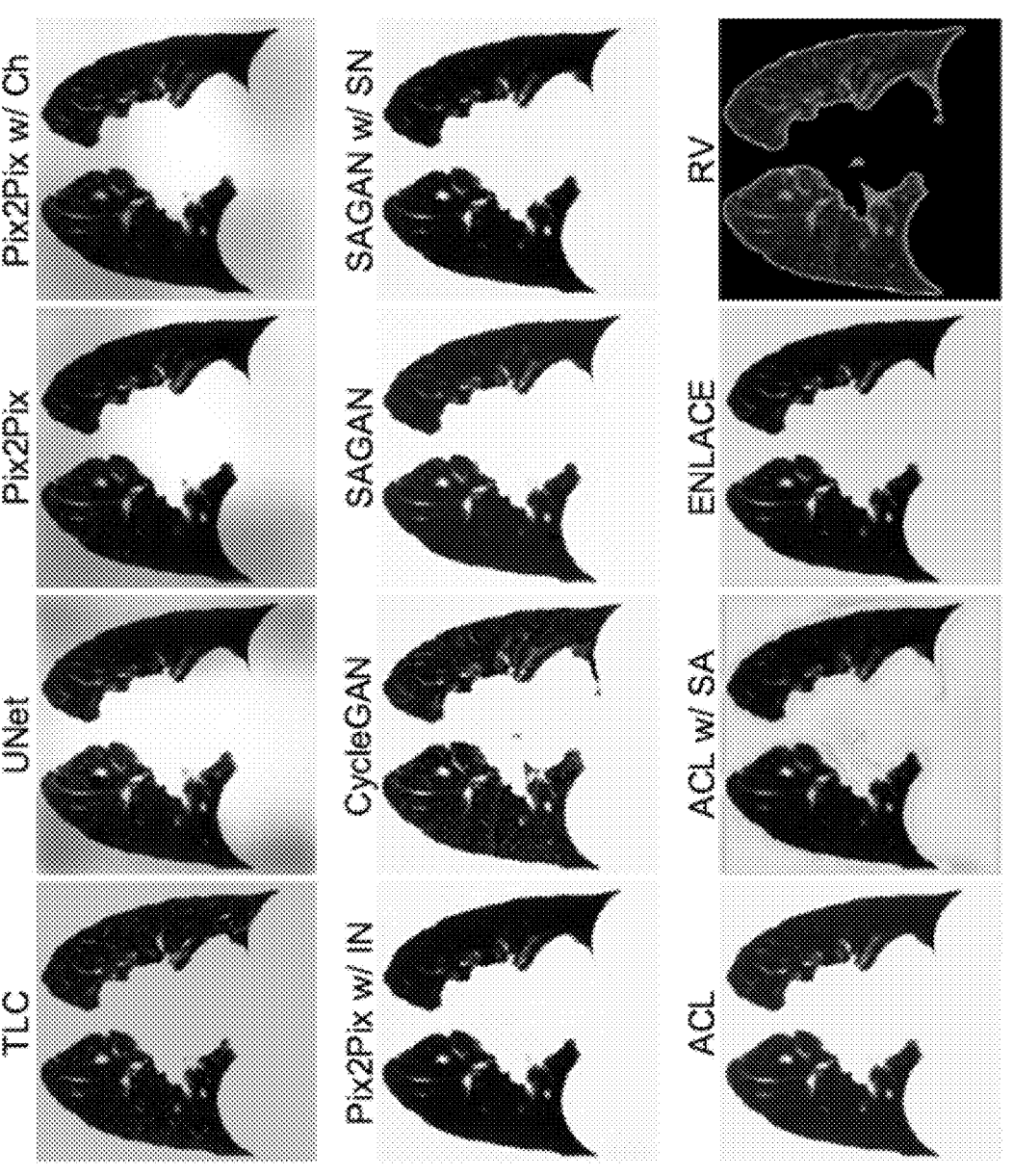
FIG. 8 shows that predicting a total lung capacity (TLC) CT scan from the corresponding RV scan using different generative models.
Figure 9:
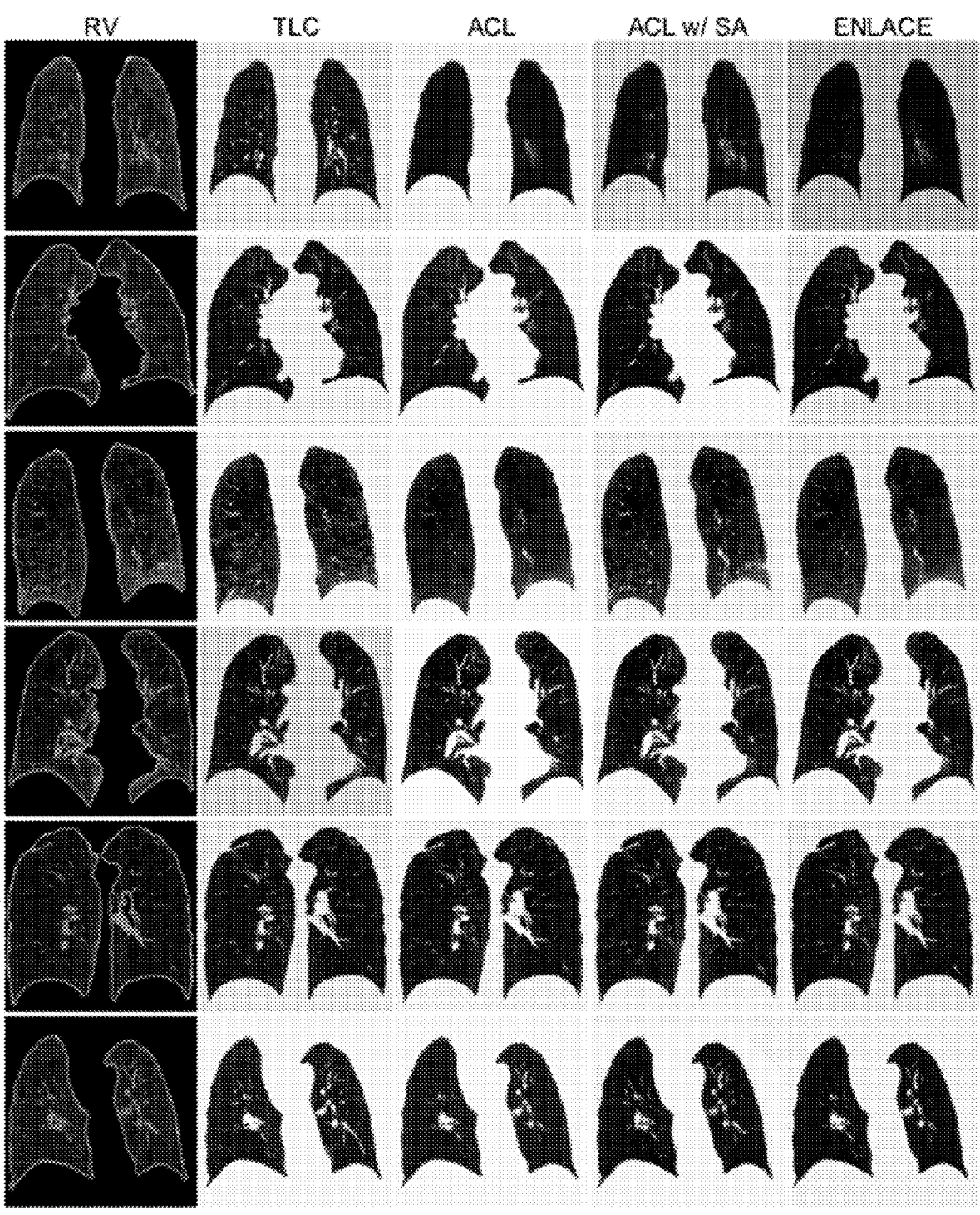
FIG. 9 shows that the TLC CT scans generated by best three generative methods across different COPD GOLD stages.

We propose to use a modified U-Net (Ronneberger et al. (2015)) architecture with skip connections for the generator $\mathcal{G}$. Initially proposed for image segmentation, U-Net architecture has been effectively modified for high-resolution image-to-image translation tasks Isola et al. (2017). FIG. 5 shows the encoder-decoder structure of our network, where each layer from the encoder is symmetrically connected (via skip connection) to a corresponding layer in the decoder. This ensures transfer of subtle lower and higher level image details directly from the encoder layers to the decoder. Each block in the encoder is describe as 2D convolution→instance normalization→ReLU (short for leaky rectified linear unit) Ioffe and Szegedy (2015); Xu et al. (2015); Radford et al. (2015).

4. Experimental Setup

4.1 Dataset

For training and evaluating ENLACE, we utilized the entire SubPopulations and Intermediate Outcome Measures in COPD Study (SPIROMICS) cohort (Couper et al. (2014)). SPIROMICS is a multi-center, prospective cohort study aimed at identifying novel phenotypes related to COPD. The study acquired breath-hold CT scans for every subject at two different volumes i.e., at total lung capacity (TLC) or end-inspiration, and residual volume (RV) or end-expiration. Using these dual-volumes scans, we derived registration-based lung function measures that would serve as targets for training our GANs. The SPIROMICS imaging protocol administered a standardized exposure to CT dosage across scanners in 14 different sites. The slice collimation was set at 0.6 mm, rotation time 0.5 s and pitch to 1.0. Philips B, GE Standard, and Siemens B35 reconstruction kernels were used (Sieren et al. (2016)). The original resolution of the CT scans was approximately $0.6 \times 0.6 \times 0.5$ mm$^3$, and the image size was $512 \times 512$ per slice, with 500 to 600 slices per image (Sieren et al. (2016)). The Global Initiative for Chronic Obstructive Lung Disease (GOLD) recommends four spirometry-guided stages of COPD—GOLD 1 (mild) to GOLD 4 (severe) (Vestbo et al. (2013). In this classification system, asymptomatic smokers are grouped in GOLD 0. To ensure that the generative model is able to capture normal physiological behavior of the lungs, non-smokers were also included for training and evaluating our generative models (Table 1).

4.2. Preprocessing

SPIROMICS offers large, high-resolution TLC and RV volumes with an approximate resolution of $0.6 \times 0.6 \times 0.5$ mm$^3$. Before registration, both the TLC and RV volumes were resampled isotropically to a resolution of $1 \times 1 \times 1$ mm$^3$. To remove outliers arising due to calcification or metal artifacts, CT intensity values were restricted from $-1024$ Hounsfield units (HU) to 1024 HU. The image volumes were then cropped into the bounding box containing the union of the lung regions of the inspiration and expiration. To further reduce the memory demand and training time for our models, a multi-resolution convolutional neural network was used to segment the lung regions (Gerard et al. (2020)). We trained our models using mid-coronal slices from each volume, which were resized to $256 \times 256$ and intensity values were rescaled to the interval $[-1, 1]$. We used a total of 100 mid-coronal slices from each scan to eliminate the slices with mostly air. SPIROMICS yielded a total of 2499 RV and TLC volume pairs, that were divided into a disjoint set of 1760 training and 739 testing subjects (Table 1).

TABLE 1

|  | Training | Testing |
|---|---|---|
| GOLD$_0$ | 537 | 225 |
| GOLD$_0$ | 268 | 113 |
| GOLD$_0$ | 453 | 189 |

TABLE 1-continued

|  | Training | Testing |
| --- | --- | --- |
| GOLD$_0$ | 287 | 122 |
| GOLD$_0$ | 85 | 37 |
| Mom-smokers | 130 | 53 |
| Total | 1760 | 739 |

Correspondingly, a total of 176,000 slices were used for training and 73,900 testing, respectively.

4.3. Local Measures of Lung Function

We used RV slices as inputs to the generative models for estimating two different measures of lung function. The first task was to estimate local tissue expansion by learning a generative model from RV to Jacobian (J). Next, we trained our models for translating an RV image to the corresponding TLC image, which can later be used for estimating other measures of local function such as the PRMs. Before training, the RV and TLC scans were co-registered using a well-known lung CT registration method—the sum-of-squared-tissue-volume-difference or simply, SSTVD (Cao et al. (2010b); Ding et al. (2012); Cao et al. (2010a)). In the next subsection, we detail the cost function optimized iteratively by SSTVD for registering two lung volumes.

4.4. SSTVD

The overall cost of the SSTVD can be divided into two terms—the sum of squares tissue volume difference (SSTVD) similarity cost for matching pulmonary CT intensities (Yin et al. (2009); Gorbunova et al. (2012)); and the sum of squared vesselness measure difference (SSVMD) term for matching lung vessels. To encourage a smooth transformation, the registration deformation field, parameterized by cubic B-splines, was also regularized (Cao et al. (2010b)). The methods seek to preserve mass and accounts for volume change during deformation. The overall variational objective function of SSTVD algorithm is given by:

$$SSTVD(I_f, I_m) = \gamma_1 \frac{1}{|\Omega|} \int_\Omega \left( I_f(x) - (x) \left\| jJ_{\varphi^{-1}} I_m(\varphi^{-1}(x)) \right) \right)^2 dx +=$$
$$\gamma_2 \frac{1}{|\Omega|} \int_\Omega \left( I_{fvm}(x) - I_{mvm}(\varphi^{-1}(x)) \right)^2 dx += \gamma_3 \int_\Omega \|L(u(x))\|^2 dx, \quad (14)$$

where $I_f$ and $I_m$ are the fixed and moving tissue density images, respectively; $I_{fvm}$ and $I_{mvm}$ are the fixed and moving vesselness images, respectively; L is the linear elasticity differential operator of the type $L = (-\alpha\Delta + \gamma)^\beta \mathbb{1}_{n \times n}; \Omega \subset \mathbb{R}^3$ is the domain of $I_f$ and $I_m$; The $|J_{\varphi^{-1}}(x)|$ term is the Jacobian determinant of $\varphi^{-1}$ and used to accommodate intensity changes in the CT images due to changing air content by ensuring the total tissue volume of the lung remains constant; $\varphi^{-1}(x)$ is the transformation from the fixed to the moving coordinate system; $u(x) = \varphi^{-1}(x)$ is the displacement field; and $\gamma_1$, $\gamma_2$ and $\gamma_3$ are weights that control the relative importance of each term in the cost function.

4.5. Model Evaluation

To ensure robust model evaluation, we propose to use four different quantitative metrics. We computed the peak signal to noise ratio in decibels (dBs) between the target y and the generated image $\hat{y}$ as:

$$PSNR(y, \hat{y}) = 10\log_{10} \frac{\max_{\hat{y}}^2}{\frac{1}{N} \sum_{i=0}^N (y, \hat{y})^2}, \quad (15)$$

where $$\max_{\hat{y}}^2$$

is the maximum possible value of image intensities. To quantify the structural consistency between the target and generated samples, we used the well-known structural similarity (SSIM) index (Wang et al. (2004)), expressed as:

$$SSIM(y, \hat{y}) = \frac{(2\mu_y\mu_{\hat{y}} + c_1)(2\sigma_{y\hat{y}} + c_2)}{(\mu_y^2 + \mu_{\hat{y}}^2 + c_1) + (\sigma_y^2 + \sigma_{\hat{y}}^2 + c_2)}, \quad (16)$$

where y and $\hat{y}$ indicate real and fake 3D volumes, respectively. Here, $\mu$'s denote means and $\sigma$'s denote standard deviations. Furthermore, we used Spearman's correlation co-efficient (rs) and mean absolute error (MAE) to assess quantitative differences between y and $\hat{y}$. An additional evaluation metric, the Dice similarity co-efficient (DSChigh), was used for assessing the overlap between the high-functioning regions of the lung, as indicated by J maps generated by SSTVD and the proposed framework. The high-functioning regions were defined to have intensities greater than the 75th percentile of the overall J im-age. Let $y_{high}$ and $\hat{y}_{high}$ be the high-function regions of the target and generated J images respectively, then DSChigh is given as:

$$DSC(y_{high}, \hat{y}_{high}) = \frac{2|y_{high} \cap \hat{y}_{high}|}{|y_{high} + \hat{y}_{high}|}, \quad (17)$$

Lastly, to evaluate the clinical significance of generated samples, we propose to perform comparison of medians across each COPD GOLD stage using the Kruskal Wallis H-test (Wallace (1959)).

5. Summary

Regional measures of lung function used for assessing chronic obstructive pulmonary disease (COPD) are typically computed by registering chest computed tomography (CT) scans acquired at different volumes, typically end-inspiration and end-expiration volumes. Since this process inherently requires CT scans at different volumes, it is not possible to estimate the local measures of lung function for patients where multiple volume scans are unavailable or are impossible to acquire. Such patients include later stage COPD subjects with reduced lung function, subjects with cancer, and patients requiring a lung transplant. Another disadvantage of acquiring multiple CT scans is the exposure to radiation dosage which is a risk factor for cancer. We propose a neural network-based generative modeling system that can directly convert a single CT scan (acquired at expiration or inspiration) directly to local measures of lung function, some of the most prominent and clinically relevant of which include, the local tissue expansion measure (Jacobian) and parametric response mappings (PRM). Our approach requires a single CT to compute these measures and can be scaled to larger cohorts where subjects have CT scans acquired at single volumes.

Example: Context-Aware Volumetric Style Transfer
for High-Resolution Cross-Volume Computed
Tomography I. Introduction CHEST computed tomography (CT) is commonly used to diagnose and assess lung disease (Lardinois et al. (2003)), (Lynch et al. (2015)). Advancements in CT hardware have resulted in large volumes that capture anatomical details at a high resolution. Computed tomography, at multiple lung volumes, facilitates clinical decision making by offering complementary information about local anatomical structure as well as function. Moreover, deformable image registration, typically of the end-inspiratory and end-expiratory CT volumes, is used to derive various surrogates for regional lung function ((Chenevert et al. (2009)); (Reinhardt et al. (2008)); (Han et al. (2012)); (Bodduluri et al. (2017))). Such multi-volume measures have improved our understanding of pulmonary abnormalities such as lung cancer (Chenevert et al. (2009)) and chronic obstructive pulmonary disease (COPD) ((Reinhardt et al. (2008)); (Han et al. (2012)); (Bodduluri et al. (2017))). For instance, parametric response mapping (PRM) was used to identify local patterns of emphysema and functional small airways disease (FSAD) from co-registered, inspiratory-expiratory chest CT volumes (Han et al. (2012)). PRM has since gathered widespread clinical attention as it has been used to detect and characterize COPD and was demonstrated to be associated with hyper-polarized gas magnetic resonance imaging (MRI)—a functional imaging modality (Capaldi et al. (2016)). While multiple volumes improve clinical assessment, acquiring them takes more time, increases radiation dosage, overall cost, and is not routinely recommended in various clinical settings. Moreover, advanced-stage COPD or cancer patients may be unable to achieve reliable end-inspiratory or expiratory CT volumes. These problems limit the utility of multi-volume approaches for analyzing lung disease. Cross-volume image synthesis could serve as a useful tool towards mitigating this challenge.

Recently, generative modeling has emerged as a useful tool for various image-to-image translation tasks ((Kingma et al. (2013)); (Goodfellow et al. (2014)); (Kingma et al. (2014))). The most prominent within this paradigm, are the generative adversarial networks (GANs) (Goodfellow et al. (2014)), that have been shown to perform remarkably well for various medical image processing tasks such as denoising ((Yang et al. (2018)); (Bera et al. (2021))), super-resolution ((You et al. (2019)); (You et al. (2022)); (Lyu et al. (2020))), data augmentation ((Shin et al. (2018)); (Frid-Adar et al. (2018))) and image-to-image translation (Wolterink et al. (2017)). The GAN framework, which typically consists of two convolutional neural networks (CNNs) competing against each other, can be differentiated by the number of spatial dimensions it attempts to model i.e., planar (2D) vs. volumetric (3D) approaches. Most of the preliminary work done towards medical image-to-image translation was constituted by 2D GAN frameworks that operated on slices instead of volumes. For instance, Yang et al. proposed to jointly minimize adversarial and perceptual loss functions for denoising low-dose CT slices from paired high-dose samples (Yang et al. (2018)). An image conditional GAN was trained in a supervised fashion to convert T1-weighted MR slices to synthetic CT images (Emani et al. (2018)). Zhou et al. developed a feature fusion approach for cross-modal MR image synthesis (Zhou et al. (2020)). They trained three different network backbones using paired 2D slices for fusing representations from different modalities.

The multiple-backbone architecture demanded larger memory and the framework was hence constrained to 2D slices (Zhou et al. (2020)). Lyu et al. proposed an ensemble learning approach for MR super-resolution. They improved model performance by using upsampled images as priors for eventually training a GAN (Lyu et al. 2020). Wolterink et al. proposed to use a CycleGAN (Zhu et al. (2017)) for unpaired MR to CT slice translation. This modeling framework relaxed the assumption of requiring paired training data and utilized two generative models to ensure cycle-consistency between domains (Wolterink et al. (2017)). The lack of supervised training in unpaired approaches often leads to structural inconsistencies between real and synthetic images. Recently, Yang et al. tried to address this by exploiting common structural attributes between two modalities (Yang et al. (2020)). All aforementioned approaches generate 2D slices which appear discontinuous when stacked together into a volume. Moreover, the slice-based methods are unable to explicitly learn largescale 3D texture patterns which strictly reduces the clinical utility of the synthetic images. The unpaired approaches that rely on multiple generative models incur large GPU memory for training and are increasingly difficult to scale at volumetric levels.

Volumetric (3D) generative frameworks address several limitations presented by the slice-based (2D) methods ((Shin et al. (2018)); (Nie et al. (2017-2018)); (Yu et al. (2019)); (Yu et al. 2020)); (Uzunova et al. (2020))). Nie et al. trained a 3D GAN on MR image patches to generate corresponding CT patches. They further used auto-context (Tu et al. (2009)), a cascade of 3D GANs, to iteratively refine CT patch synthesis by conditioning each successive GAN on outputs from the previous model (Nie et al. (2017-2018)). The networks operated on small image patches (32×32×32) and the overall volume size generated using the trained model was limited to 153×193×50. The framework additionally proposed to minimize the gradient difference loss to encourage structural consistency between real and synthetic samples (Nie et al. (2017-2018)). Unlike results from 2D GANs, the synthetic CT volumes were consistent across all three spatial dimensions. Shin et al. also proposed a 3D GAN for data augmentation but had to downsample their image volumes to 128×128×54 due to limited GPU memory available for training (Shin et al. (2017)). Recently, another patch-based 3D approach, the edge-aware GANs, leveraged edge detection to better capture structural features for multi-modality MR image synthesis (Zhou et al. (2019)). The trained model was demonstrated to generate an overall volume of size 240×240×155. A multi-resolution cascade of GANs was proposed to alleviate the memory requirements for synthesizing high-resolution 3D volumes (Uzunova et al. (2020)). Similar to Nie et al., this approach used contextual information from a lower resolution model to train a cascade of patch-based higher resolution models.

Volumetric generative models are trained either on smaller image patches or down sampled volumes due to limited GPU memory. Training GANs on patches yields sub-optimal synthesis results due to lack of global context and limited neighborhoods processed by the fully convolutional generators. This is why most of the aforementioned approaches refined their results either by cascading or additionally regularizing their models with structural constraints ((Nie et al. (2018)); (Uzunova et al. (2020))). While most of these methods focused on structural constraints, they did not explicitly model the neural style and texture transfer (NST) across modalities. For our task of converting CT from one volume to another, NST is pertinent to model subtle textural details of the lung tissue at different volumes. NST approaches mainly rely on perceptual similarity metrics computed on projections obtained from large, pre-trained object-detection (Tu et al. (2009)); (Gatys et al. (2016)); (Johnson et al. (2016)); (Zhang et al. (2018))). The lack of pre-trained 3D models for computing high-dimensional projections that encourage better perceptual consistency between real and synthesized images limits the use of NST at a volumetric level. Also, most of the NST approaches require exemplars for stylization that are not available for medical image-to-image translation. Another important limitation presented by most of the GAN studies is a lack of model validation against clinical end-points; a component which was completely missing across all the studies discussed above. Despite some very evident limitations highlighted above, volumetric GAN-based approaches still offer large, untapped potential for cross-volume CT image synthesis.

In this study, we hypothesized that image-conditional GANs can be used to translate CT from end-inspiratory volume to end-expiratory volume. This led us to investigate the role of generative models for cross volume CT synthesis, concurrently addressing the challenges presented above. We propose Lung2Lung—a context-aware, style transfer framework—for translating high-resolution CT volumes from inspiration to expiration. The Lung2Lung framework consists of a multi-view perceptual image similarity module that has been developed specifically for volumetric NST. We show that Lung2Lung framework, trained on image subvolumes, is able to generate high-resolution CT volumes up to a size of 320×320×320—significantly larger than the volumes generated by most of the 3D GANs mentioned above. The major contributions of our work can be summarized as follows.

To our knowledge, this is the first study that investigates the role of generative models for cross-volume computed tomography.

We proposed a fully convolutional 3D GAN framework that addresses the slicewise discontinuity presented by 2D GAN approaches.

To better model texture synthesis and style transfer across volumes, we introduce a multi-view perceptual similarity module.

We extend auto-context (AC), originally developed for image segmentation, for dense regression task of cross-volume synthesis.

We compare the performance of Lung2Lung with various state-of-the-art 2D and 3D image-to-image translation methods.

Unlike most other generative modeling studies, we demonstrate the effectiveness of our model using a large multi-center cohort of almost 1500 participants with a varying degree of disease severity.

In addition to routine quantitative evaluation metrics, we demonstrate that synthetic images, derived using Lung2Lung, can be used to reliably compute several clinical end-points such as PRM and air-trapping.

II. Background

Generative adversarial networks (or GANs) are a class of generative models that implicitly model the data distribution by learning a mapping $\mathcal{G} : z \rightarrow x$ from a random noise vector z to a given image x sampled from the distribution (Goodfellow et al. (2014)). Unlike other generative models, the GAN framework consists of two different networks that are trained to compete against each other until they reach Nash's equilibrium (Goodfellow et al. (2014)). This game-theoretic training approach has been successfully used to generate perceptually realistic images for various tasks.

Isola et al. extended the original GAN framework to image conditional GAN (cGAN) that is able to learn a generator $\mathcal{G} : z \rightarrow y$, from an image x in domain X to another image y in domain Y[34]. The synthetic samples $\hat{y}=\mathcal{G}$ (x), generated by G are then evaluated by a second model called the discriminator D, which is simultaneously trained to learn if the samples are real or fake. Typically, D is a binary classifier that outputs the probability of a sample being derived from the target (or data) distribution. While D is optimized to maximize this probability, the generator G tries to minimize it, a dynamic modeled by the minimax game stated as:

$$\mathcal{L}_{cGAN} = \mathbb{E}_{x_i y}[\log D(x, \ y)] += \mathbb{E}_{x_i y}[\log(1 - D(x, \mathcal{G}(x)))], \qquad (18)$$

where $\mathcal{G}$ is trained to minimize (18) such that $\{\mathcal{G}^*\}= min_\mathcal{G} \max_D \mathcal{L}_{cGAN}$. Isola et al. suggested to additionally minimize the pixelwise distance ($\ell_1$ or $\ell_2$) between the real y and generated samples $\hat{y}$ (Isola et al. (2017)). The minimax objective in (18) can be extended to express the overall generator $\mathcal{G}$ loss function as.

$$\mathcal{L}_c(x, \ y) = \underbrace{\mathcal{L}_{BCE}(D(x, \mathcal{G}(x), 1)}_{cross\ entropy\ adversarial\ loss} + \underbrace{\lambda\mathbb{E}\left[\|y - \mathcal{G}(x)\|_{\ell_1}\right]}_{\ell_1 - distance}, \qquad (19)$$

where the first term in (19) refers to binary cross-entropy (BCE) loss minimized by G, and the second term constitutes $\ell_1$–distance between the real y and generated $\hat{y}=\mathcal{G}$ (x) samples. The aforementioned framework is called Pix2Pix and has been shown to be very effective for various 2D image-to-image translation tasks (Isola et al. (2017)).

III. Lung2Lung

Figure 10:
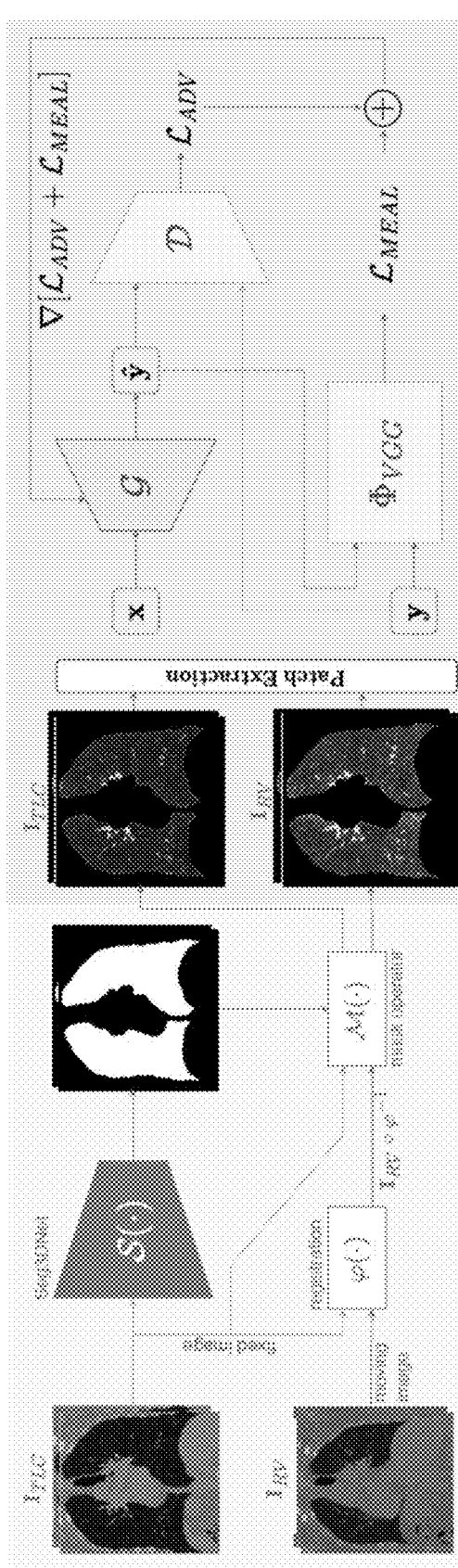
FIG. 10 illustrates overview of the framework sometimes referred to throughout as Lung2Lung. Lung segmentations of CT volumes at inspiration $\mathbf{I}_{TLC}$ and expiration $\mathbf{I}_{RV}$ were computed using Seg3DNet [8], followed by co-registration using a deformable image registration model. A generator G and D was then trained on patches x and y from TLC and RV volumes, respectively. Notice, in addition to $L_{ADV}$, gradients from the multiview perceptual similarity module $\nabla$ $\mathcal{L}_{MEAL}$ were also back-propagated to the generator.

Here, we introduce Lung2Lung—a context-aware, neural style transfer framework for synthesis of high-resolution 3D CT volumes at end-expiration or residual volumes (RV) $\mathbf{I}_{RV}$ from the corresponding end-inspiratory volume at total lung capacity (TLC) $\mathbf{I}_{TLC}$, shown in FIG. 10. The general training framework is preceded by image-registration and lung segmentation (see FIG. 10). We used a tissue intensity and vessel structure constrained, deformable image registration method to match $\mathbf{I}_{RV}$ (moving image) to the fixed image $\mathbf{I}_{TLC}$ ((Yin et al. (2009)); (Gorbunova et al. (2012))). Lung segmentations of pre-registered RV and TLC volumes were obtained using a multi-resolution CNN, the Seg3DNet (Gerard et al. (2020)). We then trained an image conditional least squares GAN model on image patches extracted from $\mathbf{I}_{RV}$ and $\mathbf{I}_{TLC}$. Below, we detail each component of the Lung2Lung framework.

A. Conditional Least Squares GAN

We formulate the cross-volume synthesis as image-to-image translation of a patch $x \in \mathbb{R}^{C \times H \times W \times D}$ from domain of TLC volumes to a patch $y \in \mathbb{R}^{1 \times H \times W \times D}$ within the domain of RV scans. The cross entropy-based adversarial feedback in (18) is known to be responsible for vanishing gradients that result in highly unstable GAN training. We use the least squares GAN (LSGAN) framework proposed by Mao et al. (Mao et al. (2017)) to stabilize GAN training. Given a dataset $$Q = \{(x_i, \ y_i)\}_{i=1}^N$$

where x, y$\in$ $\mathbb{R}^{C \times H \times W \times D}$, we train our framework using the following LSGAN objective:

$$\mathcal{L}_{LSGAN} = -\mathbb{E}_{x,y}\left[(D(x, y) - 1)^2\right] - \mathbb{E}_x\left[D(x, \mathcal{G}(x))^2\right]. \tag{20}$$

We additionally add a pixelwise $\ell_1$–distance term to get the following conditional least squares objective for the generator:

$$\mathcal{L}_{\mathcal{G}}(x, y) = \underbrace{\mathcal{L}_{MSE}(D(x, \mathcal{G}(x), 1)}_{\text{least squares adversarial loss}} + \underbrace{\lambda \mathbb{E}\left[\|y - \mathcal{G}(x)\|_{\ell_1}\right]}_{\ell_1 - \text{distance}}, \tag{21}$$

where the first term in (21) now denotes the least squares adversarial loss minimized by the generator.

B. Meal: Multiview Perceptual Similarity

Figure 12:
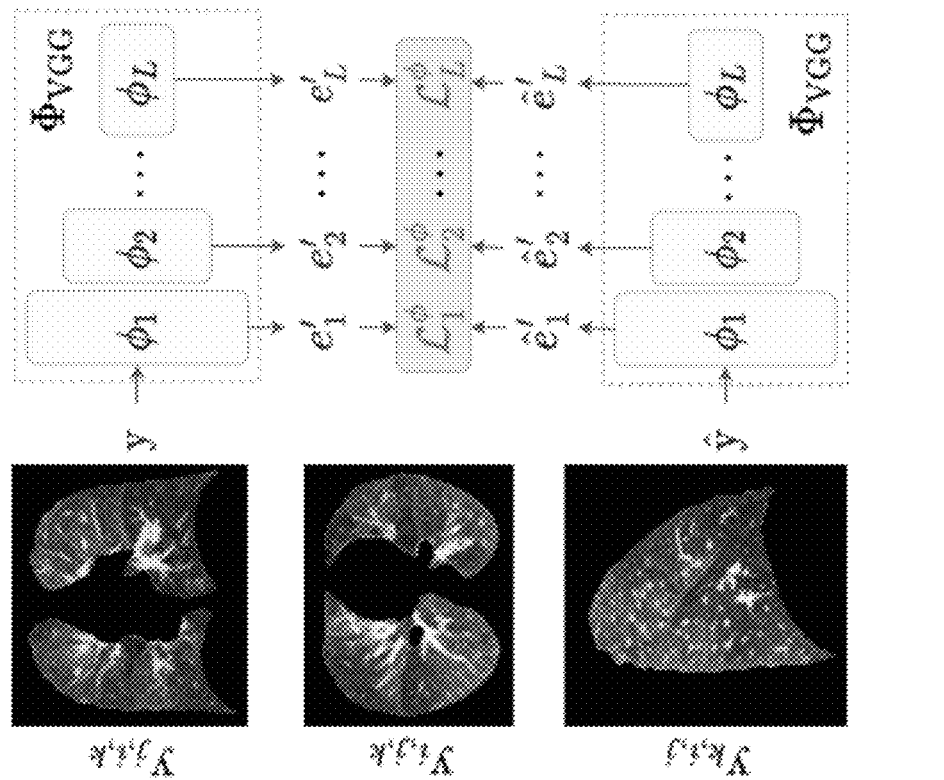
FIG. 12 shows multiview perceptual similarity (MEAL). A pre-trained VGG-19 is used to embed one of the three 2D views at a time into a higher-dimensional space. The normalized embeddings $$\varepsilon_p = \{e'_1, e'_2, \dots, e'_L\}$$

Neural style transfer approaches rely on high-dimensional projections of images from large pre-trained CNNs, trained for high-level tasks such as image classification and object detection. The distance between these internal activations is used to quantify perceptual similarity between two samples (Johnson et al. (2016)). In our work, we propose to extend a well-known perceptual similarity metric—learned perceptual image patch similarity (LPIPS)—to multiple views for general applicability to volumetric style transfer, as shown in FIG. 12 (Johnson et al. (2016)). To compute LPIPS between two slices p and $\hat{p} \in \mathbb{R}^{C \times H \times W}$, high-dimensional embeddings were extracted from a pretrained VGG (see FIG. 12). These embeddings were then unit normalized along the channel dimension to get feature stacks $$\mathcal{E}_p = \{e'_1, e'_2, \ldots, e'_L\} \text{ and } \hat{\mathcal{E}}_{\hat{p}} = \{e'_1, e'_2, \ldots, e'_L\}$$

corresponding to each patch. The overall LPIPS loss is then calculated by first scaling the $\ell_2$–distance between embeddings $\varepsilon$ and $\hat{\varepsilon}$ along the channel dimensions by $w \in \mathbb{R}^C$ followed by spatial and layer-wise averaging, expressed as:

$$\mathcal{L}_{LPIPS}(p, \hat{p}) = \sum_{l=1}^{L} \frac{1}{H_l W_l} \sum_{H,W} \|w \odot (e'_l - \hat{e}'_l)\|_{\ell_2}^2. \tag{22}$$

We extend the slice-based objective in (22) to multiple views of a medical image volume. For real y and synthetic patches $\hat{y} = \mathcal{G}(x)$ patches, where each y, $\hat{y} \in \mathbb{R}^{C \times H \times W \times D}$ we transposed each volume to compute LPIPS across all three dimensions—axial, coronal and sagittal (shown in FIG. 12). The multiview perceptual similarity (MEAL) between two volumes was thus defined as:

$$\mathcal{L}_{MEAL}(y, \hat{y}) = \underbrace{\mathcal{L}(y_{i,j,k}, \hat{y}_{i,j,k})}_{\text{axial}} + \underbrace{\mathcal{L}(y_{j,k,i}, \hat{y}_{j,k,i})}_{\text{coronal}} + \underbrace{\mathcal{L}(y_{k,i,j}, \hat{y}_{k,i,j})}_{\text{sagittal}}, \tag{23}$$

Where $\mathcal{L}(\bullet, \bullet)$ denoted $\mathcal{L}_{LPIPS}(\bullet, \bullet)$ in (23) and each term corresponded to a different view of the volume. This simple extension enabled style transfer at a volumetric level, also illustrated in FIG. 12. The overall cost function minimized by the generator for the Lung2Lung framework is:

$$\mathcal{L}_{\mathcal{G}}(x, y) = \tag{24}$$

$$\underbrace{\mathcal{L}_{MSE}(D(x, \mathcal{G}(x), 1)}_{\text{least squares adversarial loss}} + \underbrace{\lambda_1 \mathcal{L}_{l_1}(y, \mathcal{G}(x))}_{l_1 - \text{distance}} + \underbrace{\lambda_2 \mathcal{L}_{MEAL}(y, \mathcal{G}(x))}_{\substack{\text{multiview perceptual} \\ \text{similarity}}}.$$

C. Auto-Context for Dense Regression

Patch-based generative frameworks often suffer from a lack of global contextual information that is useful for image synthesis. To alleviate this problem for patch-based image segmentation methods, Tu and Bai (Tu and Bai et al. (2009) proposed to train multiple segmentation models with each successive model being conditioned on the output from its precursor, a framework they called the auto-context (AC). We utilized AC for regression by re-conditioning a second Lung2Lung model on outputs from a similar pre-trained model (see FIG. 11). Let $$Q^{(0)} = \left\{\left(x_i^{(0)}, y_i^{(0)}\right)\right\}_{i=1}^{N}$$

be the training data for initial Lung2Lung model. Using AC, we trained a subsequent refinement model using the re-conditioned dataset defined as $$Q^{(1)} = \left\{\left(x_i^{(0)}, \hat{y}_i^{(0)}, y_i^{(0)}\right)\right\}_{i=1}^{N}.$$

In general, the $n^{th}$ re-conditioning can be formulated $$Q^{(n)} = \left\{\left(x_i^{(0)}, \hat{y}_i^{(n-2)}, y_i^{(0)}\right)\right\}_{i=1}^{N}.$$

Figure 11:
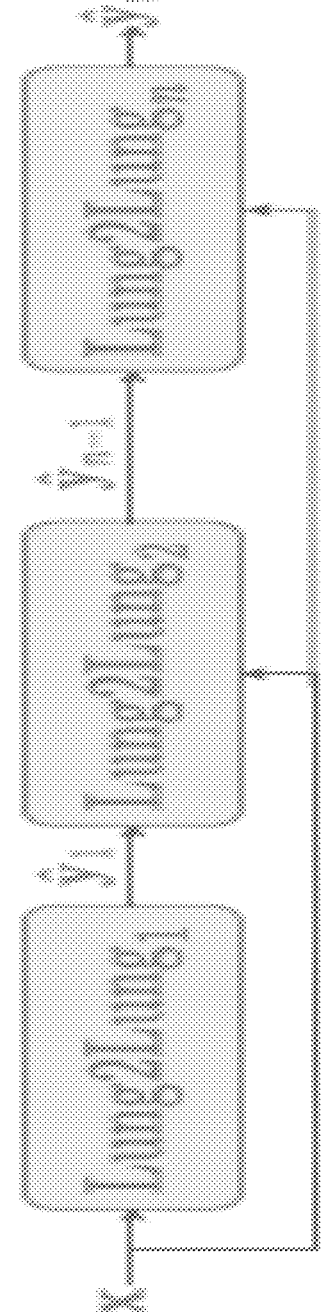
FIG. 11 shows the auto-context framework for dense regression where multiple Lung2Lung frameworks are trained, and each subsequent model is conditioned on the initial input x as well the output from its precursor, until a refined output $\hat{y}_n$ is obtained.

Notice, that each successive model was conditioned on estimates $\hat{y}^{(0)}$ from the previously trained model. Similar Lung2Lung framework was used during each training iteration, as shown in FIG. 11.

D. Generator and Discriminator Architecture

We used the UNet architecture as our generator backbone (Ronneberger et al. (2015)). Initially proposed for image segmentation, UNet has been effectively modified for high-resolution image-to image translation tasks (Isola et al, (2017)). FIG. 13 shows the encoder-decoder structure of our network, where each layer from the encoder is symmetrically connected (via skip connection) to the corresponding layer in the decoder. This ensures transfer of lower and higher level structural details directly from the encoder layers to the decoder. The input to the generator architecture is a patch of size 128×128×128 with C channels. We set C=1 for initially training the Lung2Lung model. During the second refinement stage using auto-context, the input to the generator consisted of two channels—TLC patch and RV patch estimate from the previous model. The output of the generator is a single-channel patch of size 128×128×128. The structure of each encoder block C and decoder block U, along with the kernel size k and stride length s, has been detailed in FIG. 13. All encoder-decoder blocks used 3D convolutions. The size of spatial dimensions after being operated upon by each encoder-decoder block has also been shown in FIG. 13. We also used to two 1×1×1 convolution layers (M1 and M2) for adjusting the feature map sizes at the input and output of the model.

We used a Markovian PatchGAN discriminator in this work (Isola et al, (2017)). Instead of providing adversarial feedback over the entire image, the PatchGAN discriminator attempts to classify image patches of size s, where s is smaller than the overall spatial dimension of the input tensor. Four downsampling blocks (C's shown in FIG. 13), identical to the generator, were used to define the discriminator architecture. For input tensor of size 128×128×128, we set the patch size s=8. Such a patch-based discriminator models the entire image as a Markov random field and helps capture high-resolution details present in smaller patches. For optimizing the generator and discriminator parameters, we used Adam optimizer with imbalanced learning rates 0.0002 and 0.00005, respectively. The hyperparameters $\lambda_1$ and $\lambda_2$ were set to 100 for all experiments. All models were implemented using the open source framework PyTorch (Paszke et al, (2019)) and were trained on a single NVIDIA RTX8000 GPU with a batch size of 4.

IV. Experimental Details

A. Dataset and Preprocessing

For training and evaluating our models, we utilized data from the SubPopulations and Intermediate Outcome Measures in COPD Study (SPIROMICS) cohort [40]. SPIROMICS is a multi-center, prospective cohort study that acquired breathhold CT scans for every participant at two different volumes—total lung capacity (TLC) and residual volume (RV). The original resolution of the chest CT scans was approximately 0.6×0.6×0.5 mm3, and the image size was 512×512 per slice, with 500 to 600 slices per volume [41]. SPIROMICS acquired chest scans across a varying degree of disease severity, defined by the Global Initiative for Chronic Obstructive Lung Disease (GOLD) (Vestbo et al, (2013)). GOLD 1 to GOLD 4 indicated mild to severe COPD, while asymptomatic smokers were grouped in GOLD 0. A small subset of normal individuals who never smoked (NS) was also included for analysis (see Table 2). Before training, CT at IRV was deformed into the space of TLC images ITLC by a mass preserving deformable image registration method ((Yin et al, (2009)); (Gorbunova et al, (2012))). Image volumes at TLC and RV were then resampled isotropically to a resolution of 1×1×1 mm³. To remove outliers arising due to calcification or metal artifacts, intensity values were clipped to the interval [−1024, 1024] Hounsfield units (HU). The image volumes were then cropped to the bounding box containing the union of the lung regions of the inspiration and expiration. A multi-resolution convolutional neural network was used to segment the lung regions (Gerard et al. (2020)). We further normalized the image intensities between −1 and 1 before using them for training. The disjoint training and testing sets had 1055 and 512 subjects, respectively that spanned across varying degree of disease severity, indicated by Table 2.

TABLE 2

|  | Training | Testing |
|---|---|---|
| Individuals who never smoked (NS) | 154 | 59 |
| GOLD 0 | 200 | 100 |
| GOLD 1 | 200 | 99 |
| GOLD 2 | 200 | 100 |
| GOLD 3 | 200 | 100 |
| GOLD 4 | 133 | 54 |
| Total | 1055 | 512 |

B. Model Evaluation

We evaluated our models using several quantitative metrics. To assess voxelwise $\mathcal{G}$ differences between real y and synthetic $\hat{y}=\mathcal{G}_\theta(x)$ volumes, we used peak signal to noise ratio (PSNR) in decibels (dB), mean absolute error (MAE) in Hounsfield units (HU), and normalized mean squared error (NMSE). All metrics were computed within the lung region defined by mask. PSNR between y and ŷ was defined as:

$$PSNR(y, \hat{y}) = 20\log_{10}\frac{\max\{y\}}{\|y - \hat{y}\|_{\ell_2}}, \quad (25)$$

where max {y} is the maximum possible value of image intensities. Similarly, NMSE was defined as:

$$NMSE(y, \hat{y}) = \frac{\|y - \hat{y}\|_{\ell_2}^2}{\|y\|_{\ell_2}^2}. \quad (26)$$

To further assess voxelwise consistency, Spearman's correlation co-efficient (rs) between image intensities within the lung region was also used. Overall perceptual similarity between real and synthetic volumes was quantified by the structural similarity index (SSIM) (Wang et al. (2015)), defined as:

$$SSIM(y, \hat{y}) = \frac{(2\mu_y\mu_{\hat{y}} + c_1)(2\sigma_{y\hat{y}} + c_2)}{(\mu_y^2 + \mu_{\hat{y}}^2 + c_1) + (\sigma_y^2 + \sigma_{\hat{y}}^2 + c_2)}, \quad (27)$$

where y and ŷ indicated real and fake 3D volumes, respectively. Here, μ's denote means and σ's denote standard deviations. To further assess agreement between the means of real and synthetically generated images, we conducted Bland-Altman analysis]. We also evaluated sample (Giavarina et al. (2015)) quality by segmenting pulmonary fissures, which are a major anatomical component involved in lobar sliding and overall tissue expansion. In doing so, we sought to evaluate if synthetic volumes captured the fissures reliably. Fissure segmentation was performed using FissureNet, a state-of-the-art lung fissure segmentation method (Gerard et al. (2018)).

C. Clinical Validation

Most of the studies involved with the development of generative models tend to ignore clinical validation of the synthetic samples generated by their models. We sought to rigorously evaluate the clinical reliability of our samples by computing air trapping and parametric response mapping (PRM)-based emphysema and functional small airways disease (FSAD). These biomarkers, which require an expiratory volume, have shown to be associated various disease outcomes in COPD.

D. Comparison with State-of-the-Art

We compared performance of Lung2Lung with two state of-the-art 2D GAN frameworks—Pix2Pix (Isola et al. (2017)) and Yang et al. (Yang et al. (2018)) Pix2Pix framework forms the basis for most of the generative modeling approaches in medical imaging, while the work by Yang et al. (Yang et al. (2018)) was the only study that investigated perceptual loss functions for 2D images denoising. We also compared the performance of Lung2Lung with a commonly used volumetric image synthesis framework Pix2Pix3D, the 3D counterpart of Pix2Pix (Isola et al, (2017)). Lastly, an ablation study investigating the impact of MEAL and auto-context was conducted.

V. Results

We show volumetric synthesis results across multiple views in FIG. 14. All 3D models, including Pix2Pix3D, Lung2Lung and Lung2Lung$_{AC}$, generated spatially consistent results. On the contrary, the 2D GAN models (Pix2Pix and Yang et al. (Yang et al. (2018))) were trained using coronal slices that appeared discontinuous across axial and sagittal views (red regions in FIG. 14). Also, the Pix2Pix3D generated blurred images with several regions missing important details (see yellow regions in FIG. 14). The Lung2Lung framework, which incorporated multiview perceptual similarity (MEAL), performed significantly better than all other models with PSNR 24.28 dB and SSIM of 0.9018. Adding AC further improved PSNR from 24.28 dB to 24.42 dB (p<0.0001), MAE from 90.81 HU to 89.01 HU (p<0.0001), and Spearman's correlation from 0.596 to 0.602 (p<0.0001). Wilcoxon's signed ranked test indicated a statistically significant difference in performance between Lung2LungAC and all other models. Also note that the volumetric methods performed better than the slice-based methods, as shown in Table 3. Quantitative performance of Lung2LungAC across varying disease severity, ranging from GOLD 0 to GOLD 1, is also shown in Table 4.

We also conducted a regression analysis between the means of real and synthetically generated RV scans $$I_{RV}^{mean} \text{ and } \hat{I}_{RV}^{mean},$$

respectively (see FIG. 15). The means showed good agreement with an overall coefficient of determination $r^2$=0.637 and a regression slope m=0.536. A concurrent Bland-Altman analysis, shown in FIG. 15, showed small variability in error between the means of real and synthetic RV scans. A qualitative performance evaluation of Lung2LungAC across varying COPD severity demonstrated that the model performed well across all GOLD stages and was able to consistently capture intricate vessel structures, highlighted in yellow (see FIG. 16).

We conducted model validation against some well-known imaging biomarkers, derived from RV scans, used to charwhen computed using the real and synthetic RV scans (see FIG. 17). Synthetic RV images generated by Lung2Lung yielded similar air-trapping and FSAD percentages as compared to real RV scans (Wilcoxon's p>0.05). Lung2Lung$_{AC}$ slightly underestimated air-trapping and FSAD but Pix2Pix3D was not able to capture the patterns reliably, comparison illustrated in FIG. 17. In FIG. 19, we also show the impact of MEAL on axial slices in comparison to Pix2Pix$_{3D}$, which clearly underestimated air-trapping to be 13.10%. Lung2Lung estimated 25.46% air-trapping for the same subject which was very close to the ground truth value of 27.41%.

VI. Discussion and Conclusion

Multiple volume surrogates of lung function have gained widespread clinical attention over the past two decades and are commonly used for characterizing the local functional abnormalities in COPD (Han et al. (2005)). While these measures enable better understanding of disease mechanisms, they require CT at different volumes which are not available or recommended in most clinical settings. In this work, we hypothesized that CT at end-inspiration contained sufficient structural information that could be used to predict the associated end-expiratory CT volume. To that end, we proposed a context-aware, neural style transfer framework for translating inspiratory CT to the paired expiratory volume. Image-to-image translation for large 3D volumes entailed several challenges. Foremost, was the large GPU memory required to handle increasingly large CT volumes. To mitigate

TABLE 3

| | PSNR (dB) | SSIM | MAE (HU) | $r^S$ | NMSE (%) |
|---|---|---|---|---|---|
| Pix2Pix | 22.42 ± 1.395** | 0.8243 ± 0.0375*** | 110.14 ± 38.32*** | 0.547 ± 0.094*** | 4.935 ± 3.409*** |
| Yang et al. [12] | 24.17 ± 2.325** | 0.8484 ± 0.0422*** | 90.55 ± 43.19*** | 0.605 ± 0.1081 | 3.659 ± 2.866*** |
| Pix2Pix$_{3D}$ | 24.05 ± 1.95*** | 0.8991 ± 0.0314*** | 93.56 ± 32.13*** | 0.585 ± 0.109*** | 3.629 ± 2.854** |
| LUNG2LUNG | 24.28 ± 2.60*** | 0.9018 ± 0.0350*** | 90.81 ± 35.83*** | 0.596 ± 0.122*** | 3.700 ± 3.300*** |
| LUNG2LUNG w/auto-context | 24.42 ± 2.56 | 0.9021 ± 0.0346 | 89.01 ± 35.37 | 0.602 ± 0.118 | 3.622 ± 3.221 |

TABLE 4

| | PSNR (dB) | SSIM | MAE (HU) | $r^S$ | NMSE (%) |
|---|---|---|---|---|---|
| Individuals who never smoked (NS) | 22.36 ± 1.71 | 0.8968 ± 0.0341 | 114.86 ± 34.94 | 0.482 ± 0.076 | 6.180 ± 2.898 |
| GOLD 0 | 23.30 ± 1.92 | 0.9013 ± 0.0319 | 102.90 ± 32.66 | 0.543 ± 0.092 | 4.975 + 3.967 |
| GOLD 1 | 23.30 ± 2.39 | 0.8854 ± 0.0374 | 101.09 ± 38.34 | 0.559 ± 0.102 | 4.504 ± 3.712 |
| GOLD 2 | 24.37 ± 1.97 | 0.8983 ± 0.0346 | 87.09 ± 35.46 | 0.606 ± 0.095 | 3.125 ± 2.040 |
| GOLD 3 | 26.03 ± 2.03 | 0.9145 ± 0.0289 | 69.04 ± 28.72 | 0.690 ± 0.093 | 1.790 ± 1.052 |
| GOLD 4 | 27.72 ± 1.77 | 0.9241 ± 0.0235 | 57.27 ± 24.08 | 0.746 ± 0.066 | 1.135 ± 0.834 | acterize COPD. These included CT density-based air-trapping (Newman et al. (1994)) and image registration-based PRM characterization of functional small airways disease (FSAD) (Han et al. (2005)). Percent air-trapping was defined as the fraction of voxels below −856 HU within the lung region. For computing FSAD, joint histograms of coregistered TLC-RV image pairs were used. FSAD was defined to be the fraction of voxels between −950 HU and −810 HU in TLC and between −1000 HU and −857 HU in an RV scan. We assessed differences in percent air-trapping and FSAD overall GPU memory demand, most of the existing generative adversarial learning methods are trained on 2D slices. This, however, leads to discontinuous transitions across slices, which seriously limits the radiological utility of these images. Moreover, 2D models are not able to capture three-dimensional structures that might by important for overall image structure. We observed a decreased performance, in general, from 2D models when compared to 3D models (see Table 3). We trained our models on 3D subvolumes or patches continuous in three dimensions. Patch-based networks are often limited by the size of receptive field and may not be able to model global patterns within an image volume. We tried to address this problem by devising several measures. First, we used relatively larger patch sizes of the order 128×128×128. To further increase the overall receptive field, we used multiple convolution layers in encoder and decoder blocks.

A shortcoming of most volumetric generative models was that they did not attempt to model the inherent style and texture patterns during image translation. Volumetric style-transfer was particularly limited due to a lack of 3D models that could be used for generating deep representations. Secondly, most style transfer approaches rely on stylization exemplars that are used to model the textures of an image. For our task, modeling texture within the expiratory CT was pertinent since most clinical measures depend largely on the local tissue texture. We proposed a multiview perceptual similarity (MEAL) to model image textures in 3D. MEAL used a pre-trained VGG-19 backbone to extract deep representations of 3D volumes across different views—axial, coronal, and sagittal. This was designed to ensure perceptual consistency across all dimensions of the model. Adding MEAL to the model, in case of Lung2Lung, lead to a 0.23 dB increase in PSNR, when compared to the Pix2Pix3D, as shown in Table 3. To further improve the quantitative performance of our model, we used auto-context (AC) that improved the overall quantitative performance of the model (see Table 3). An important part of our work was constituted by the clinical validation of our model. Lung2LungAC performed well across varying COPD severity. (see Table 4). We also highlighted some intricate vessel structures captured successfully by Lung2LungAC across different GOLD stages (see FIG. 16). When FSAD and air-trapping was computed using real and synthetic RV scans, Lung2Lung captured a similar distribution of these biomarkers when compared to ground-truth (see FIG. 17). A similar visual comparison was presented in FIG. 19. It is common in clinical practice to acquire lung images only at inspiration, and yet it is becoming evident that an early sign of numerous lung diseases is seen on the expiratory image manifesting as air trapping or FSAD. Our method will allow for the retrospective assessment of patient scans to assess if pathologies were proceeded by FSAD, providing critical insights into disease processes. Additionally, the assessment of FSAD is dependent upon a patient making an appropriate effort to expel as much air from the lungs as possible. Furthermore, this difficult maneuver must be repeatable so as to allow for the tracking of disease progression. Lung2Lung eliminates the need for the patient to achieve a breath hold at this low lung volume, thus allowing for the more accurate tracing of longitudinal changes. Our method will allow for the automated reporting of functional abnormalities across a wide variety of lung diseases providing the potential for expanded insights into early pathologies associated with transplant rejection, prediction of rapid progression of emphysema or fibrosis, and more. These new insights will provide improved decisions regarding treatment approaches. Moreover, our method allows for retrospective evaluation where multiple lung volumes have not been imaged and prospectively where patient cooperation limits the repeatability of an inspiratory/expiratory image pair.

Options Variations and Alternatives

In FIG. 20, a computed tomography (CT) imaging system 10 is shown which includes a gantry 12. The gantry 12 may include an x-ray source that projects x-rays toward a detector and/or collimator. The projected x-rays may pass through a patient (not shown) disposed upon the table 14. FIG. 21 is a block diagram illustrating one example of a control system for the imaging system 10 shown. The control system may include a computer with one or more processors 20. A memory or storage media 30 is shown which may contain instructions for performing various processors. The storage media is operatively connected to the computer with one or more processors 20. A table controller 22, x-ray controller 24, and gantry motor controller 26 are also operatively connected to the computer with one or more processors 20.

In operation during a scan of the patient, in order to acquire x-ray projection data, the gantry 12 may rotate around a center of rotation. Digitized x-ray projection data is used to produce a reconstructed image. In some embodiments the computer with one or more processors 20 may be used to execute instructions stored in the memory or storage media 30 to use the reconstructed image as input into a generative neural network model. Alternatively, the reconstructed image may be stored and then later communicating to another computing device with one or more processors which is programmed to apply the generative neural network model.

FIG. 22 illustrates an overview of one example of a method. The method may be performed by instructions executed on one or more processors. In step 100, the instructions provide for acquiring a first image of a patient. The image may be acquired in any number of ways. Where the method is performed by a CT imaging system or other imaging system, the image may have just been acquired from a patient. In other instances, the image may be stored in a database of imagery and retrieved from the database or otherwise acquired. It is also to be understood that the image is not necessarily a CT image as other types of imaging technologies may be used to create the image. As previously described the CT image may be a pulmonary image which shows lungs at a first volume such as at inspiration, at expiration, or other volume.

In step 102, a generative neural network model is applied to the first image of the patient in order to generate a second image of the patient. The generative neural network model may be of the type shown and described above or may be a variation or alternative thereto. It is contemplated that the generative neural network model may be constructed through the training methods shown and described above or modifications thereto, including without limitation, modifications in the pre-trained weak generative learners, modifications in the generator used, and modifications in the confidence network. Where the first image is a pulmonary image which shows lungs at a first volume, the second image may be an image which shows the lungs at a second volume, the second volume different from the first volume. When the lungs are shown at different volumes this is also an example of the images occurring at different points in time within a respiratory cycle. It is also contemplated that the second image may show the lungs at a more remote point in time prior to or subsequent to the first image. In addition, the second image may be a Jacobian image.

In step 104, once the second image is generated, an analysis may be performed using the first image and the second image. The type of analysis performed may depend upon the type of image, the biological tissue being imaged, or other parameters. The analysis may be of the same type performed where multiple images are acquired in the convention manner through separate acquiring each image with an imaging system.

It should further be understood that the generative neural network model or a plurality of generative neural network models may be used to generate additional images from the first image. Thus, for example, based on a single image by applying a generative neural network with different parameters one may obtain different second, third, or additional images. Or alternatively, a single image may be used as input into two different generative neural network models to generate different second and third images. Where an analysis is to be performed, any number of generated images may be used. For example, images may be generated for a plurality of different lung volumes or images may be generated for a plurality of different points in time relative to the first image.

Although various examples show and describe prediction of regional lung function from a single CT scan, it is to be understood that numerous other options, variations, and alternatives are contemplated. For example, the methods and system provided in the present disclosure may be extended to other clinically relevant image synthesis tasks, including translation of a CT scan at a single inspiratory or expiratory volume to the corresponding functional image such as a hyperpolarized gas magnetic resonance image (MRI), or to the corresponding positron emission tomography (PET) scan. This is potentially feasible since it has been shown that there are texture features within CT images which can identify benign vs malignant images. Pulmonary functional images are technically difficult and expensive to acquire in a clinical setting because they require inhalation of a noble gas (in case of hyperpolarized gas MRI or CT) or a radioactive tracer (in case of a PET scan).

Similarly, the methods and systems described in the present disclosure may be used in characterizing temporal changes in a CT by translating scans at a given time point to a time point in the future or past. This may be used to help predict visual changes in lung tissues as a disease progresses over time, thereby enabling better temporal profiling of higher-risk subjects.

It is common in clinical practice to acquire lung images only at inspiration, and yet it is becoming evident that an early sign of numerous lung diseases is seen on the expiratory image manifesting as air trapping or "Functional Small Airways Disease" (fSAD). This invention will allow for the retrospective assessment of patient scans to assess if pathologies were proceeded by fSAD, providing critical insights into disease processes. Additionally, the assessment of fSAD is dependent upon a patient making an appropriate effort to expel as much air from the lungs as possible. Furthermore, this difficult maneuver must be repeatable so as to allow for the tracking of disease progression. The methods and systems of the present disclosure eliminate the need for the patient to achieve a breath hold at this low lung volume, thus allowing for the more accurate tracing of longitudinal changes. The method disclosed here will allow for the automated reporting of functional abnormalities across a wide variety of lung diseases providing the potential for expanded insights into early pathologies associated with transplant rejection, prediction of rapid progression of emphysema or fibrosis, and more. These new insights will provide improved decisions regarding treatment approaches. On the research side, the invention allows for retrospective evaluation where multiple lung volumes have not been imaged and prospectively where patient cooperation limits the repeatability of an inspiratory/expiratory image pair. The limitation of scanning to a single lung volume holds the potential of reducing radiation dose to a patient, allowing for the study of a patient more often, potentially catching important changes in lung function earlier.

Thus, it is to be further understood that existing data sets may be leveraged using the methods and systems of the present disclosure. It is to be further understood that in addition to use in evaluating lung images, the methods and systems described herein may be used in other biomedical applications. For example, they may be used in imaging of other organs. It is contemplated that single scans may be translated to a point in the past or the future to show changes due to disease, aging, or other factors or conditions.

Although specific ensembles are shown and described, the present invention contemplates various options and alternatives. For example, although an ensemble of pre-trained weak generative learners is shown, it is contemplated that this ensemble may include additional learners or a subset of additional learners. It is to be further understood that different generators may be used, and different confidence networks or other types of evaluators may be used.

The methods described herein or aspects thereof may be incorporated into software in the form of instructions stored on a non-transitory computer or machine readable medium.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Certain embodiments may be described herein as implementing mathematical methodologies including logic or a number of components, modules, or mechanisms. Modules may constitute either software modules (e.g., code embodied on a machine-readable medium or in a transmission signal) or hardware modules. A hardware module is tangible unit capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. As used herein, "hardware-implemented module" refers to a hardware module. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules. Where the term "processor" is used, it is to be understood that it encompasses one or more processors whether located together or remote from one another.

Similarly, the methods described herein may be at least partially processor-implemented. For example, at least some of the operations of a method may be performed by one or processors or processor-implemented hardware modules. The performance of certain of the operations may be distributed among the one or more processors, not only residing within a single machine, but deployed across a number of machines. In some example embodiments, the processor or processors may be located in a single location (e.g., within a hospital, clinic, or medical office environment), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., application program interfaces (APIs).)

The performance of certain of the operations may be distributed among the one or more processors, not only residing within a single machine, but deployed across a number of machines. In some example embodiments, the one or more processors or processor-implemented modules may be located in a single geographic location (e.g., within a hospital, an office environment, or a server farm). In other example embodiments, the one or more processors or processor-implemented modules may be distributed across a number of geographic locations.

Some portions of this specification are presented in terms of algorithms or symbolic representations of operations on data stored as bits or binary digital signals within a machine memory (e.g., a computer memory). These algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities. Typically, but not necessarily, such quantities may take the form of electrical, magnetic, or optical signals capable of being stored, accessed, transferred, combined, compared, or otherwise manipulated by a machine. It is convenient at times, principally for reasons of common usage, to refer to such signals using words such as "data," "content," "bits," "values," "elements," "symbols," "characters," "terms," "numbers," "numerals," or the like. These words, however, are merely convenient labels and are to be associated with appropriate physical quantities.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the disclosure. This description should be read to include one or at least one and the singular also includes the plural unless it is obvious that it is meant otherwise.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Reference throughout this specification to "an example" means that a particular feature, structure, or characteristic described in connection with the example is included in at least one embodiment. Thus, appearances of the phrases "in an example" in various places throughout this specification are not necessarily all referring to the same embodiment.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function or "step for [perform]ing [a function] . . . ", it is intended that such elements are to be interpreted under 35 U.S.C. 112§ (f). However, for any claims containing elements designated in any other manner, it is intended that such elements are not to be interpreted under 35 U.S.C. § 112(f).

The invention is not to be limited to the particular embodiments described herein. In particular, the invention contemplates numerous variations including in types of functional imaging technologies used and in the specific algorithms applied. The foregoing description has been presented for purposes of illustration and description. It is not intended to be an exhaustive list or limit any of the invention to the precise forms disclosed. It is contemplated that other alternatives or exemplary aspects are considered included in the invention. The description is merely examples of embodiments, processes, or methods of the invention. It is understood that any other modifications, substitutions, and/or additions can be made, which are within the intended spirit and scope of the invention.

REFERENCES

The following references are hereby incorporated by reference as if set forth herein.
1. Bach, P. B., Mirkin, J. N., Oliver, T. K., Azzoli, C. G., Berry, D. A., Brawley, O. W., Byers, T., Colditz, G. A., Gould, M. K., Jett, J. R., et al., 2012. Benefits and harms of ct screening for lung cancer: a systematic review. Jama 307, 2418-2429.
2. Belloli, E. A., Degtiar, I., Wang, X., Yanik, G. A., Stuckey, L. J., Verleden, S. E., Kazerooni, E. A., Ross, B. D., Murray, S., Galbán, C. J., et al., 2017. Parametric response mapping as an imaging biomarker in lung transplant recipients. American journal of respiratory and critical care medicine 195, 942-952.
3. Bhatt, S. P., Bodduluri, S., Newell, J. D., Hoffman. E. A., Sieren, J. C., Han, M. K., Dransfield, M. T., Reinhardt, J. M., Investigators, C., et al., 2016. CT-derived biomechanical metrics improve agreement between spirometry and emphysema. Academic Radiology 23, 1255-1263.
4. Bodduluri, S., Bhatt, S. P., Hoffman, E. A., Newell, J. D., Martinez, C. H., Dransfield, M. T., Han, M. K., Reinhardt, J. M., 2017. Biomechanical CT metrics are associated with patient outcomes in COPD. Thorax 72, 409-414.
5. Bodduluri, S., Newell Jr, J. D., Hoffman, E. A., Reinhardt, J. M., 2013. Registration-based lung mechanical analysis of chronic obstructive pulmonary disease (COPD) using a supervised machine learning framework. Academic Radiology 20, 527-536
6. Boes, J. L., Hoff, B. A., Bule, M., Johnson, T. D., Rehemtulla, A., Chamberlain, R., Hoffman, E. A., Kazerooni, E. A., Martinez, F. J., Han, M. K., et al., 2015. Parametric response mapping monitors temporal changes on lung ct scans in the subpopulations and intermediate outcome measures in copd study (spiromics). Academic radiology 22, 186-194.
7. Boudewijn, I. M., Postma, D. S., Telenga, E. D., Ten Hacken, N. H., Timens, W., Oudkerk, M., Ross, B. D., Galbán, C. J., van den Berge, M., 2015. Effects of ageing and smoking on pulmonary computed tomography scans using parametric response mapping. European Respiratory Journal 46, 1193-1196.
8. Cao, K., Ding, K., Christensen, G. E., Reinhardt, J. M., 2010a. Tissue volume and vesselness measure preserving nonrigid registration of lung ct images, in: Medical Imaging 2010: Image Processing, International Society for Op-tics and Photonics. p. 762309.
9. Cao, K., Du, K., Ding, K., Reinhardt, J. M., Christensen, G. E., 2010b. Regularized nonrigid registration of lung CT images by preserving tissue volume and vesselness measure. Grand Challenges in Medical Image Analysis, 43-54.
10. Capaldi, D. P., Zha, N., Guo, F., Pike, D., McCormack, D. G., Kirby, M., Par-raga, G., 2016. Pulmonary imaging biomarkers of gas trapping and emphysema in copd: 3he mr imaging and ct parametric response maps. Radiology 279, 597-608.
11. Celli, B. R., Wedzicha, J. A., 2019. Update on clinical aspects of chronic obstructive pulmonary disease. New England Journal of Medicine 381, 1257-1266.
12. Chen, Q., Koltun, V., 2014. Fast mrf optimization with application to depth reconstruction, in: Proceedings of the IEEE conference on computer vision and pattern recognition, pp. 3914-3921.
13. Chen, Y., Shi, F., Christodoulou, A. G., Xie, Y., Zhou, Z., Li, D., 2018. Efficient and accurate MRI super-resolution using a generative adversarial net-work and 3D multi-level densely connected network, in: International Conference on Medical Image Computing and Computer-Assisted Intervention, Springer. pp. 91-99.
14. Couper, D., LaVange, L. M., Han, M., Barr, R. G., Bleecker, E., Hoffman, E. A., Kanner, R., Kleerup, E., Martinez, F. J., Woodruff, P. G., et al., 2014. Design of the SubPopulations and Intermediate Outcomes in COPD Study (SPIROMICS). Thorax 69, 492-495.
15. Ding, K., Cao, K., Fuld, M. K., Du, K., Christensen, G. E., Hoffman, E. A., Reinhardt, J. M., 2012. Comparison of image registration based measures of regional lung ventilation from dynamic spiral ct with xe-ct. Medical physics 39, 5084-5098.

16. Emami, H., Dong, M., Nejad-Davarani, S. P., Glide-Hurst, C. K., 2018. Generating synthetic CTs from magnetic resonance images using generative adversarial networks. Medical Physics 45, 3627-3636.

17. Galbán, C. J., Chenevert, T. L., Meyer, C. R., Tsien, C., Lawrence, T. S., Hamstra, D. A., Junck, L., Sundgren, P. C., Johnson, T. D., Ross, D. J., et al., 2009. The parametric response map is an imaging biomarker for early cancer treatment outcome. Nature medicine 15, 572-576.

18. Galba'n, C. J., Han, M. K., Boes, J. L., Chughtai, K. A., Meyer, C. R., Johnson, T. D., Galba'n, S., Rehemtulla, A., Kazerooni, E. A., Martinez, F. J., et al., 2012. Computed tomography-based biomarker provides unique signature for diagnosis of COPD phenotypes and disease progression. Nature Medicine 18, 1711.

19. Gerard, S. E., Herrmann, J., Kaczka, D. W., Musch, G., Fernandez-Bustamante, A., Reinhardt, J. M., 2020. Multi-resolution convolutional neural networks for fully automated segmentation of acutely injured lungs in multiple species. Medical Image Analysis 60, 101592.

20. Goodfellow, I., Pouget-Abadie, J., Mirza, M., Xu, B., Warde-Farley, D., Ozair, S., Courville, A., Bengio, Y., 2014. Generative adversarial networks, in: Advances in Neural Information Processing Systems, pp. 2672-2680.

21. Gorbunova, V., Sporring, J., Lo, P., Loeve, M., Tiddens, H. A., Nielsen, M., Dirksen, A., de Bruijne, M., 2012. Mass preserving image registration for lung ct. Medical image analysis 16, 786-795.

22. Ho, T. T., Kim, T., Kim, W. J., Lee, C. H., Chae, K. J., Bak, S. H., Kwon, S. O., Jin, G. Y., Park, E. K., Choi, S., 2021. A 3d-cnn model with ct-based parametric response mapping for classifying copd subjects. Scientific Reports 11, 1-12.

23. Ioffe, S., Szegedy, C., 2015. Batch normalization: Accelerating deep network training by reducing internal covariate shift. arXiv preprint arXiv:1502.03167.

24. Isola, P., Zhu, J. Y., Zhou, T., Efros, A. A., 2017. Image-to-image translation with conditional adversarial networks, in: Proceedings of the IEEE Conference on Computer Vision and Pattern Recognition, pp. 1125-1134.

25. Jin, D., Xu, Z., Tang, Y., Harrison, A. P., Mollura, D. J., 2018. CT-realistic lung nodule simulation from 3D conditional generative adversarial networks for robust lung segmentation, in: International Conference on Medical Image Computing and Computer-Assisted Intervention, Springer. pp. 732-740.

26. Jing, Y., Yang, Y., Feng, Z., Ye, J., Yu, Y., Song, M., 2019. Neural style transfer: A review. IEEE Transactions on Visualization and Computer Graphics.

27. Kingma, D. P., Mohamed, S., Rezende, D. J., Welling, M., 2014. Semi-supervised learning with deep generative models, in: Advances in Neural Information Processing Systems, pp. 3581-3589.

28. Kingma, D. P., Welling, M., 2013. Auto-encoding variational bayes. arXiv preprint arXiv:1312.6114.

29. Labaki, W. W., Gu, T., Murray, S., Hatt, C. R., Galba'n, C. J., Ross, B. D., Martinez, C. H., Curtis, J. L., Hoffman, E. A., Pompe, E., et al., 2019. Voxel-wise longitudinal parametric response mapping analysis of chest computed tomography in smokers. Academic radiology 26, 217-223.

30. Ledig, C., Theis, L., Husza'r, F., Caballero, J., Cunningham, A., Acosta, A., Aitken, A., Tejani, A., Totz, J., Wang, Z., et al., 2017. Photo-realistic single image super-resolution using a generative adversarial network, in: Proceedings of the IEEE Conference on Computer Vision and Pattern Recognition, pp. 4681-4690.

31. Lyu, Q., Shan, H., Wang, G., 2020. MRI super-resolution with ensemble learning and complementary priors. IEEE Transactions on Computational Imaging 6, 615-624.

32. Mahapatra, D., Antony, B., Sedai, S., Garnavi, R., 2018. Deformable medical image registration using generative adversarial networks, in: 2018 IEEE 15th International Symposium on Biomedical Imaging (ISBI 2018), IEEE. pp. 1449-1453.

33. Mao, X., Li, Q., Xie, H., Lau, R. Y., Wang, Z., Paul Smolley, S., 2017. Least squares generative adversarial networks, in: Proceedings of the IEEE international conference on computer vision, pp. 2794-2802.

34. Maselli, D. J., Yen, A., Wang, W., Okajima, Y., Dolliver, W. R., Mercugliano, C., Anzueto, A., Restrepo, M. I., Aksamit, T. R., Basavaraj, A., et al., 2021. Small airway disease and emphysema are associated with future exacerbations in smokers with ct-derived bronchiectasis and copd: Results from the copd gene cohort. Radiology, 204052.

35. Milz, S., Rudiger, T., Suss, S., 2018. Aerial GANeration: Towards realistic data augmentation using conditional GANs, in: Proceedings of the European Conference on Computer Vision (ECCV), pp. 1-14.

36. Nie, D., Shen, D., 2020. Adversarial confidence learning for medical image segmentation and synthesis. International Journal of Computer Vision 128.

37. Nie, D., Trullo, R., Lian, J., Petitjean, C., Ruan, S., Wang, Q., Shen, D., 2017. Medical image synthesis with context-aware generative adversarial networks, in: International Conference on Medical Image Computing and Computer-Assisted Intervention, Springer. pp. 417-425.

38. Pompe, E., van Rikxoort, E. M., Schmidt, M., Rühaak, J., Estrella, L. G., Vliegenthart, R., Oudkerk, M., de Koning, H. J., van Ginneken, B., de Jong, P. A., et al., 2015. Parametric response mapping adds value to current computed tomography biomarkers in diagnosing chronic obstructive pulmonary disease. American journal of respiratory and critical care medicine 191, 1084-1086.

39. Radford, A., Metz, L., Chintala, S., 2015. Unsupervised representation learning with deep convolutional generative adversarial networks. arXiv preprint arXiv: 1511.06434.

40. Ran, M., Hu, J., Chen, Y., Chen, H., Sun, H., Zhou, J., Zhang, Y., 2019. Denoising of 3D magnetic resonance images using a residual encoder-decoder wasserstein generative adversarial network. Medical Image Analysis 55, 165-180.

41. Regan, E. A., Hokanson, J. E., Murphy, J. R., Make, B., Lynch, D. A., Beaty, T. H., Curran-Everett, D., Silverman, E. K., Crapo, J. D., 2011. Genetic epidemiology of COPD (COPDGene) study design. COPD: Journal of Chronic Obstructive Pulmonary Disease 7, 32-43.

42. Reinhardt, J. M., Christensen, G. E., Hoffman, E. A., Ding, K., Cao, K., 2007. Registration-derived estimates of local lung expansion as surrogates for regional ventilation, in: Biennial International Conference on Information Processing in Medical Imaging, Springer. pp. 763-774.

43. Reinhardt, J. M., Ding, K., Cao, K., Christensen, G. E., Hoffman, E. A., Bodas, S. V., 2008. Registration-based estimates of local lung tissue expansion compared to xenon CT measures of specific ventilation. Medical Image Analysis 12, 752-763.

44. Ronneberger, O., Fischer, P., Brox, T., 2015. U-Net: Convolutional networks for biomedical image segmentation, in: International Conference on Medical Image Computing and Computer-Assisted Intervention, Springer. pp. 234-241.

45. Shan, H., Zhang, Y., Yang, Q., Kruger, U., Kalra, M. K., Sun, L., Cong, W., Wang, G., 2018. 3-D convolutional encoder-decoder network for low-dose CT via transfer learning from a 2-D trained network. IEEE Transactions on Medical Imaging 37, 1522-1534.

46. Shin, H. C., Tenenholtz, N. A., Rogers, J. K., Schwarz, C. G., Senjem, M. L., Gunter, J. L., Andriole, K. P., Michalski, M., 2018. Medical image synthesis for data augmentation and anonymization using generative adversarial networks, in: International Workshop on Simulation and Synthesis in Medical Imaging, Springer. pp. 1-11.

47. Siddiquee, M. M. R., Zhou, Z., Tajbakhsh, N., Feng, R., Gotway, M. B., Bengio, Y., Liang, J., 2019. Learning fixed points in generative adversarial networks: From image-to-image translation to disease detection and localization, in: Proceedings of the IEEE International Conference on Computer Vision, pp. 191-200.

48. Sieren, J. P., Newell Jr, J. D., Barr, R. G., Bleecker, E. R., Burnette, N., Carretta, E. E., Couper, D., Goldin, J., Guo, J., Han, M. K., et al., 2016. Spiromics protocol for multicenter quantitative computed tomography to phenotype the lungs. American journal of respiratory and critical care medicine 194, 794-806.

49. Smith, B. M., Austin, J. H., Newell Jr, J. D., D'Souza, B. M., Rozenshtein, A., Hoffman, E. A., Ahmed, F., Barr, R. G., 2014. Pulmonary emphysema subtypes on computed tomography. the MESA COPD study. The American Journal of Medicine 127, 94-e7.

50. Smith-Bindman, R., Lipson, J., Marcus, R., Kim, K. P., Mahesh, M., Gould, R., De Gonzalez, A. B., Miglioretti, D. L., 2009. Radiation dose associated with common computed tomography examinations and the associated lifetime attributable risk of cancer. Archives of internal medicine 169, 2078-2086.

51. Tanner, C., Ozdemir, F., Profanter, R., Vishnevsky, V., Konukoglu, E., Goksel, O., 2018. Generative adversarial networks for MR-CT deformable image registration. arXiv preprint arXiv:1807.07349.

52. Tolstikhin, I., Gelly, S., Bousquet, O., Simon-Gabriel, C. J., Schölkopf, B., 2017. Adagan: Boosting generative models. arXiv preprint arXiv:1701.02386.

53. Ulyanov, D., Vedaldi, A., Lempitsky, V., 2016. Instance normalization: The missing ingredient for fast stylization. arXiv preprint arXiv:1607.08022.

54. Vestbo, J., Hurd, S. S., Agust'i, A. G., Jones, P. W., Vogelmeier, C., Anzueto, A., Barnes, P. J., Fabbri, L. M., Martinez, F. J., Nishimura, M., et al., 2013. Global strategy for the diagnosis, management, and prevention of chronic obstructive pulmonary disease: GOLD executive summary. American Journal of Respiratory and Critical Care Medicine 187, 347-365.

55. Vincent, P., Larochelle, H., Lajoie, I., Bengio, Y., Manzagol, P. A., Bottou, L., 2010. Stacked denoising autoencoders: Learning useful representations in a deep network with a local denoising criterion. Journal of Machine Learning Research 11.

56. Wallace, D. L., 1959. Simplified beta-approximations to the Kruskal-Wallis H test. Journal of the American Statistical Association 54, 225-230.

57. Wang, Z., Bovik, A. C., Sheikh, H. R., Simoncelli, E. P., 2004. Image quality assessment: from error visibility to structural similarity. IEEE Transactions on Image Processing 13, 600-612.

58. Wolterink, J. M., Dinkla, A. M., Savenije, M. H., Seevinck, P. R., van den Berg, C. A., Isgum, I., 2017. Deep MR to CT synthesis using unpaired data, in: International Workshop on Simulation and Synthesis in Medical Imaging, Springer. pp. 14-23.

59. Xia, Y., Ravikumar, N., Greenwood, J. P., Neubauer, S., Petersen, S. E., Frangi, A. F., 2021. Super-resolution of cardiac mr cine imaging using conditional gans and unsupervised transfer learning. Medical Image Analysis 71, 102037.

60. Xu, B., Wang, N., Chen, T., Li, M., 2015. Empirical evaluation of rectified activations in convolutional network. arXiv preprint arXiv:1505.00853.

61. Yang, Q., Yan, P., Zhang, Y., Yu, H., Shi, Y., Mou, X., Kalra, M. K., Zhang, Y., Sun, L., Wang, G., 2018. Low-dose CT image denoising using a generative adversarial network with Wasserstein distance and perceptual loss. IEEE Transactions on Medical Imaging 37, 1348-1357.

62. Yi, X., Babyn, P., 2018. Sharpness-aware low-dose CT denoising using conditional generative adversarial network. Journal of Digital Imaging 31, 655-669.

63. Yin, Y., Hoffman, E. A., Lin, C. L., 2009. Mass preserving nonrigid registration of ct lung images using cubic b-spline. Medical physics 36, 4213-4222.

64. You, C., Li, G., Zhang, Y., Zhang, X., Shan, H., Li, M., Ju, S., Zhao, Z., Zhang, Z., Cong, W., et al., 2019. CT super-resolution gan constrained by the identical, residual, and cycle learning ensemble (GAN-CIRCLE). IEEE Transactions on Medical Imaging 39, 188-203.

65. Yu, B., Zhou, L., Wang, L., Fripp, J., Bourgeat, P., 2018. 3D cGAN based cross-modality MR image synthesis for brain tumor segmentation, in: 2018 IEEE 15th International Symposium on Biomedical Imaging (ISBI 2018), IEEE. pp. 626-630.

66. Zhang, H., Goodfellow, I., Metaxas, D., Odena, A., 2019. Self-attention generative adversarial networks, in: International conference on machine learning, PMLR. pp. 7354-7363.

67. Zhang, Y., Miao, S., Mansi, T., Liao, R., 2018. Task driven generative modeling for unsupervised domain adaptation: Application to X-ray image segmentation, in: International Conference on Medical Image Computing and Computer-Assisted Intervention, Springer. pp. 599-607.

68. Zhang, Y., Yang, L., Chen, J., Fredericksen, M., Hughes, D. P., Chen, D. Z., 2017. Deep adversarial networks for biomedical image segmentation utilizing unannotated images, in: International Conference on Medical Image Computing and Computer-Assisted Intervention, Springer. pp. 408-416.

69. Zhu, J. Y., Park, T., Isola, P., Efros, A. A., 2017. Unpaired image-to-image translation using cycle-consistent adversarial networks, in: Proceedings of the IEEE International Conference on Computer Vision, pp. 2223-2232.

70. D. Lardinois, W. Weder, T. F. Hany, E. M. Kamel, S. Korom, B. Seifert, G. K. von Schulthess, and H. C. Steinert, "Staging of non-small-cell lung cancer with integrated positron-emission tomography and computed tomography," New England Journal of Medicine, vol. 348, no. 25, pp. 2500-2507, 2003.

71. D. A. Lynch, J. H. Austin, J. C. Hogg, P. A. Grenier, H.-U. Kauczor, A. A. Bankier, R. G. Barr, T. V. Colby, J. R. Galvin, P. A. Gevenois, et al., "CT-definable subtypes of chronic obstructive pulmonary disease: a statement of the Fleischner Society," Radiology, vol. 277, no. 1, pp. 192-205, 2015.

72. S. Bera and P. K. Biswas, "Noise conscious training of non local neural network powered by self attentive spectral normalized markovian patch GAN for low dose CT denoising," IEEE Transactions on Medical Imaging, vol. 40, no. 12, pp. 3663-3673, 2021.

73. S. You, B. Lei, S. Wang, C. K. Chui, A. C. Cheung, Y. Liu, M. Gan, G. Wu, and Y. Shen, "Fine perceptive GANs for brain MR image super-resolution in wavelet domain," IEEE Transactions on Neural Networks and Learning Systems, 2022.

74. M. Frid-Adar, I. Diamant, E. Klang, M. Amitai, J. Goldberger, and H. Greenspan, "GAN-based synthetic medical image augmentation for increased CNN performance in liver lesion classification," Neurocomputing, vol. 321, pp. 321-331, 2018.

75. D. Nie, R. Trullo, J. Lian, L. Wang, C. Petitjean, S. Ruan, Q. Wang, and D. Shen, "Medical image synthesis with deep convolutional adversarial networks," IEEE Transactions on Biomedical Engineering, vol. 65, no. 12, pp. 2720-2730, 2018.

76. B. Yu, L. Zhou, L. Wang, Y. Shi, J. Fripp, and P. Bourgeat, "Ea-GANs: Edge-aware generative adversarial networks for cross-modality MR image synthesis," IEEE Transactions on Medical Imaging, vol. 38, no. 7, pp. 1750-1762, 2019.

77. H. Yang, J. Sun, A. Carass, C. Zhao, J. Lee, J. L. Prince, and Z. Xu, "Unsupervised MR-to-CT synthesis using structure-constrained CycleGAN," IEEE Transactions on Medical Imaging, vol. 39, no. 12, pp. 4249-4261, 2020.

78. B. Yu, L. Zhou, L. Wang, Y. Shi, J. Fripp, and P. Bourgeat, "Sample-adaptive GANs: linking global and local mappings for cross-modality MR image synthesis," IEEE Transactions on Medical Imaging, vol. 39, no. 7, pp. 2339-2350, 2020.

79. T. Zhou, H. Fu, G. Chen, J. Shen, and L. Shao, "Hi-Net: Hybrid-fusion network for multi-modal MR image synthesis," IEEE Transactions on Medical Imaging, vol. 39, no. 9, pp. 2772-2781, 2020.

80. S. U. Dar, M. Yurt, L. Karacan, A. Erdem, E. Erdem, and T. C, ukur, "Image synthesis in multi-contrast MRI with conditional generative adversarial networks," IEEE Transactions on Medical Imaging, vol. 38, no. 10, pp. 2375-2388, 2019.

81. H. Uzunova, J. Ehrhardt, and H. Handels, "Memory-efficient GAN-based domain translation of high resolution 3D medical images," Computerized Medical Imaging and Graphics, vol. 86, p. 101801, 2020.

82. Z. Tu and X. Bai, "Auto-context and its application to high-level vision tasks and 3D brain image segmentation," IEEE Transactions on Pattern Analysis and Machine Intelligence, vol. 32, no. 10, pp. 1744-1757, 2009.

83. L. A. Gatys, A. S. Ecker, and M. Bethge, "Image style transfer using convolutional neural networks," in Proceedings of the IEEE Conference on Computer Vision and Pattern Recognition, pp. 2414-2423, 2016.

84. J. Johnson, A. Alahi, and L. Fei-Fei, "Perceptual losses for real-time style transfer and super-resolution," in European Conference on Computer Vision, pp. 694-711, Springer, 2016.

85. R. Zhang, P. Isola, A. A. Efros, E. Shechtman, and O. Wang, "The unreasonable effectiveness of deep features as a perceptual metric," in Proceedings of the IEEE Conference on Computer Vision and Pattern Recognition, pp. 586-595, 2018.

86. O. Ronneberger, P. Fischer, and T. Brox, "U-Net: Convolutional networks for biomedical image segmentation," in International Conference on Medical Image Computing and Computer-Assisted Intervention, pp. 234-241, Springer, 2015.

87. A. Paszke, S. Gross, F. Massa, A. Lerer, J. Bradbury, G. Chanan, T. Killeen, Z. Lin, N. Gimelshein, L. Antiga, et al., "Pytorch: An imperative style, high-performance deep learning library," Advances in Neural Information Processing Systems, vol. 32, 2019.

88. D. Couper, L. M. LaVange, M. Han, R. G. Barr, E. Bleecker, E. A. Hoffman, R. Kanner, E. Kleerup, F. J. Martinez, P. G. Woodruff, et al, "Design of the SubPopulations and Intermediate Outcomes in COPD Study (SPIROMICS)," Thorax, vol. 69, no. 5, pp. 492-495, 2014.

89. D. Giavarina, "Understanding Bland Altman analysis," Biochemia Med-ica, vol. 25, no. 2, pp. 141-151, 2015.

90. S. E. Gerard, T. J. Patton, G. E. Christensen, J. E. Bayouth, and J. M. Reinhardt, "FissureNet: A deep learning approach for pulmonary fissure detection in CT images," IEEE Transactions on Medical Imaging, vol. 38, no. 1, pp. 156-166, 2018.

91. K. B. Newman, D. A. Lynch, L. S. Newman, D. Ellegood, and J. D. Newell Jr, "Quantitative computed tomography detects air trapping due to asthma," Chest, vol. 106, no. 1, pp. 105-109, 1994.

What is claimed is:

1. A machine implemented method comprising:
acquiring at a processor a first three-dimensional image of a patient by performing a CT scan of an anatomical structure of a patient, the anatomical structure in a first state or condition;
applying at the processor a context-aware volumetric style transfer framework configured to process volumetric data as a unified three-dimensional tensor to the first three-dimensional image of the patient to generate a second image, wherein the context-aware volumetric style transfer framework comprises a generative adversarial neural network;
wherein the generative adversarial neural network comprises a generator network and a discriminator network, wherein the generator network and the discriminator network are configured to process volumetric data and generate the second image from the first three-dimensional image;
wherein the generative adversarial neural network further comprises a multi-view perceptual similarity module configured to provide perceptual consistency across axial, coronal, and sagittal planes of the volumetric image data.

2. The machine implemented method of claim 1 further comprising performing, at the processor, an analysis using the first image and the second image.

3. The machine implemented method of claim 1 wherein the first image is a first pulmonary image and wherein the second image is a second pulmonary image.

4. The machine implemented method of claim 3 wherein the first pulmonary image shows lungs at a first volume and wherein the second pulmonary image shows the lungs at a second volume, the first volume different from the second volume.

5. The machine implemented method of claim 4 wherein the first pulmonary image is a scan of the lungs at expiration and wherein the second pulmonary image is an inspiratory image of the lungs.

6. The machine implemented method of claim 4 wherein the first pulmonary image is an inspiratory scan of lungs and wherein the second pulmonary image is of the lungs at expiration.

7. The machine implemented method of claim 1 wherein the first image is associated with a first point in time and wherein the second image is associated with a second point in time, the first point in time different from the second point in time.

8. The method of claim 1 wherein the second image is a synthetic three dimensional image which represents the anatomical structure of the patient in a second state or condition, the second state or condition different from the first state or condition.

9. The method of claim 1 wherein the multi-view perceptual similarity module comprises a convolutional neural network trained using a perceptual-loss function applied to projections of the volumetric data across the axial, coronal, and sagittal planes, the network being configured to quantify feature-space similarity between corresponding anatomical regions across said planes to enforce visual coherence during image generation.

10. A system comprising:
a processor;
a non-transitory machine readable medium;
a plurality of instructions stored on the non-transitory machine readable medium which upon execution by the processor cause the processor to: evaluate a single three-dimensional functional image to directly estimate pulmonary function, the single functional image acquired by one of computed tomography (CT), hyperpolarized gas magnetic resonance imaging (MRI), positron emission tomography (PET), and single photon emission computed tomography (SPECT);
wherein the single functional image is evaluated by applying an ensemble-driven adversarial confidence learning framework configured to process volumetric data using a generator network, a discriminator network, and an ensemble confidence module that fuses outputs of a plurality of generator sub-networks according to adversarially learned confidence weights to the single functional image to directly generate a functional analysis image representing at least one measure of regional lung function, wherein the functional analysis image is generated from the single functional without performing image registration or motion estimation between multiple respiratory states;

wherein the at least one measure of regional lung function comprises at least one of: a Jacobian determinant map for measuring local tissue expansion, a parametric response map for quantifying emphysema, and a map of functional small airways disease.

11. The system of claim 10 wherein the plurality of instructions apply the generative neural network model to produce a generated image and wherein the single CT scan image and the generated image are used to directly estimate the pulmonary function.

12. The system of claim 11 wherein the single CT scan image and the generated image are of the lungs at different volumes.

13. The system of claim 10 wherein the generative neural network model is a generative adversarial network (GANs) model.

14. The system of claim 13 wherein the GANs model is trained used an ensemble of pre-trained weak generative learners.

15. The system of claim 10 wherein the pulmonary function comprises regional lung deformation.

16. A system comprising:
a processor;
a non-transitory machine readable medium;
a plurality of instructions stored on the non-transitory machine readable medium which upon execution by the processor cause the processor to:
acquire an image;
apply a context-aware volumetric style transfer framework configured to process the image as volumetric data represented as a three-dimensional tensor, wherein the context-aware volumetric style transfer framework comprises:
a generative neural network model configured to process the image as volumetric data; and
a multi-view perceptual similarity module configured to process the volumetric data to provide consistency across axial, coronal, and sagittal planes of the volumetric data.

17. The system of claim 16 wherein the multi-view perceptual similarity module comprises a convolutional neural network trained to compute perceptual-loss features across axial, coronal, and sagittal projections of the volumetric data.

* * * * *